(12) United States Patent
Kim et al.

(10) Patent No.: US 12,048,239 B2
(45) Date of Patent: Jul. 23, 2024

(54) COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Byungku Kim, Suwon-si (KR); Kipo Jang, Suwon-si (KR); Dong Min Kang, Suwon-si (KR); Jiyun Kwon, Suwon-si (KR); Namheon Lee, Suwon-si (KR); Sung-Hyun Jung, Suwon-si (KR); Hayun Song, Suwon-si (KR); Bo won Choi, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 552 days.

(21) Appl. No.: 17/227,715

(22) Filed: Apr. 12, 2021

(65) Prior Publication Data

US 2021/0328144 A1    Oct. 21, 2021

(30) Foreign Application Priority Data

Apr. 20, 2020 (KR) .................. 10-2020-0047580

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C07D 405/04* (2013.01);
(Continued)

(58) Field of Classification Search
CPC ............... H10K 85/633; H10K 85/615; H10K 85/654; H10K 85/6574; H10K 50/11;
(Continued)

(56) References Cited

U.S. PATENT DOCUMENTS 5,061,569 A    10/1991  Vanslyke et al.
2010/0025669 A1    2/2010  Hwang et al.
(Continued)

FOREIGN PATENT DOCUMENTS

CN    101638377 A    2/2010
CN    102356060 A    2/2012
(Continued)

OTHER PUBLICATIONS

Kang, Yu Jin, Si Hyun Han, and Jun Yeob Lee. "Lifetime enhancement of blue thermally activated delayed fluorescent devices by separated carrier channels using dibenzofuran-triazine type hosts." Journal of industrial and engineering chemistry 62 (2018): 258-264. (Year: 2018).*

(Continued)

*Primary Examiner* — Dawn L Garrett
(74) *Attorney, Agent, or Firm* — Lee IP Law, P.C.

(57) ABSTRACT

A composition for an organic optoelectronic device, an organic optoelectronic device, and a display device, the
(Continued)

composition including a first compound represented by Chemical Formula 1 and a second compound represented by a combination of Chemical Formula 2 and Chemical Formula 3:

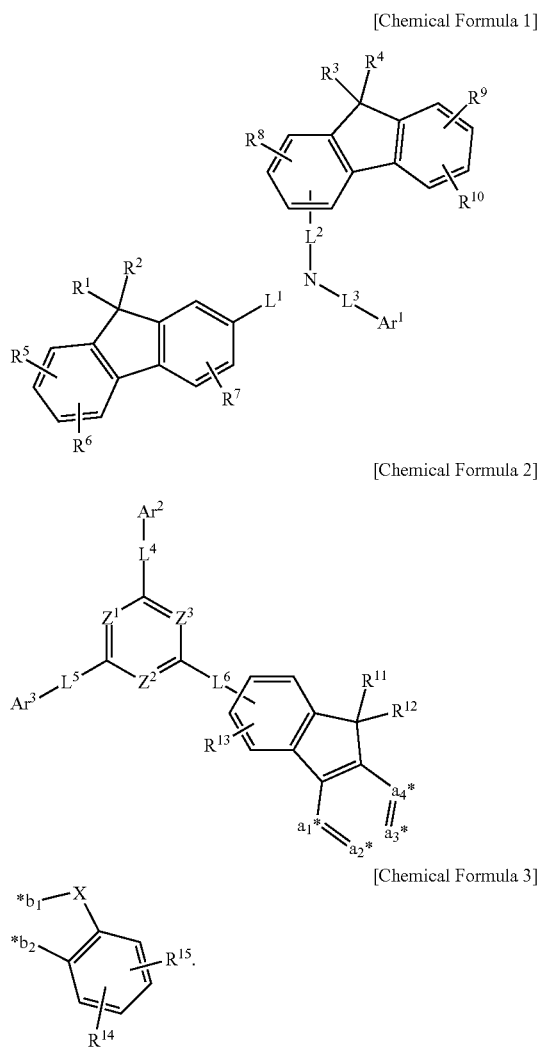

14 Claims, 1 Drawing Sheet

(51) Int. Cl.
 *C07D 405/04* (2006.01)
 *C09K 11/06* (2006.01)
 *H10K 50/11* (2023.01)
 *H10K 101/00* (2023.01)
 *H10K 101/10* (2023.01)

(52) U.S. Cl.
 CPC ............ *C09K 11/06* (2013.01); *H10K 85/615* (2023.02); *H10K 85/654* (2023.02); *H10K 85/6574* (2023.02); *C07C 2603/18* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 85/626* (2023.02); *H10K 2101/10* (2023.02); *H10K 2101/90* (2023.02)

(58) Field of Classification Search
 CPC ............ H10K 85/626; H10K 2101/10; H10K 2101/90; H10K 85/6576; H10K 50/12; H10K 85/622; C07C 211/61; C07C 2603/18; C07D 405/04; C09K 11/06; C09K 2211/1007; C09K 2211/1011; C09K 2211/1014; C09K 2211/1018
 See application file for complete search history.

(56) References Cited

U.S. PATENT DOCUMENTS

| | | | |
|---|---|---|---|
| 2012/0012832 | A1 | 1/2012 | Yabunouchi et al. |
| 2015/0207075 | A1 | 6/2015 | Mujica-Fernaud et al. |
| 2016/0133851 | A1* | 5/2016 | Jo .................. C07D 405/04 |
| | | | 252/500 |
| 2017/0317285 | A1* | 11/2017 | Mujica-Fernaud .... H05B 33/20 |
| 2019/0185460 | A1 | 6/2019 | Kim et al. |

FOREIGN PATENT DOCUMENTS

| | | |
|---|---|---|
| CN | 104488359 A | 4/2015 |
| CN | 105473684 A | 4/2016 |
| CN | 108623481 A | 10/2018 |
| CN | 106946859 B | 3/2019 |
| CN | 109427985 A | 3/2019 |
| CN | 109942557 A | 6/2019 |
| CN | 110903276 A | 3/2020 |
| JP | 1993-009471 A | 1/1993 |
| JP | 1995-126615 A | 5/1995 |
| JP | 1998-095973 A | 4/1998 |
| JP | 3065125 B2 | 7/2000 |
| JP | 2004-063277 A | 2/2004 |
| JP | 3838766 B2 | 10/2006 |
| JP | 2010-222268 A | 10/2010 |
| JP | 4788078 B2 | 10/2011 |
| JP | 6137898 B2 | 5/2017 |
| JP | 6149247 B1 | 6/2017 |
| KR | 10-1537499 B1 | 7/2015 |
| KR | 10-2015-0098706 A | 8/2015 |
| KR | 10-2016-0046075 A | 4/2016 |
| KR | 10-2017-0051762 A | 5/2017 |
| KR | 10-2017-0088601 A | 8/2017 |
| KR | 10-2017-0111802 A | 10/2017 |
| KR | 10-2017-0136391 A | 12/2017 |
| KR | 10-2017-0136916 A | 12/2017 |
| KR | 10-2018-0043726 A | 4/2018 |
| KR | 10-2018-0053121 A | 5/2018 |
| KR | 10-1883591 B1 | 7/2018 |
| KR | 10-2019-0005522 A | 1/2019 |
| KR | 10-2019-0007892 A | 1/2019 |
| KR | 10-2019-0047631 A | 5/2019 |
| KR | 10-2019-0079343 A | 7/2019 |
| KR | 10-2019-0085659 A | 7/2019 |
| KR | 10-2019-0131468 A | 11/2019 |
| WO | WO 1995/009147 A1 | 4/1995 |
| WO | WO 2007/072952 A1 | 6/2007 |
| WO | WO 2010/106806 A1 | 9/2010 |
| WO | WO 2012/015265 A1 | 2/2012 |
| WO | WO 2013/118846 A1 | 8/2013 |
| WO | WO 2013/135352 A1 | 9/2013 |
| WO | WO 2014/015935 A2 | 1/2014 |
| WO | WO 2014/015937 A1 | 1/2014 |
| WO | WO 2014/015938 A1 | 1/2014 |
| WO | WO 2015/053403 A1 | 4/2015 |
| WO | WO 2015/082056 A1 | 6/2015 |
| WO | WO 2015/084114 A1 | 6/2015 |
| WO | WO 2018-034517 A1 | 2/2018 |

OTHER PUBLICATIONS

Chinese Office action dated Feb. 28, 2024.

* cited by examiner

[FIG. 1]
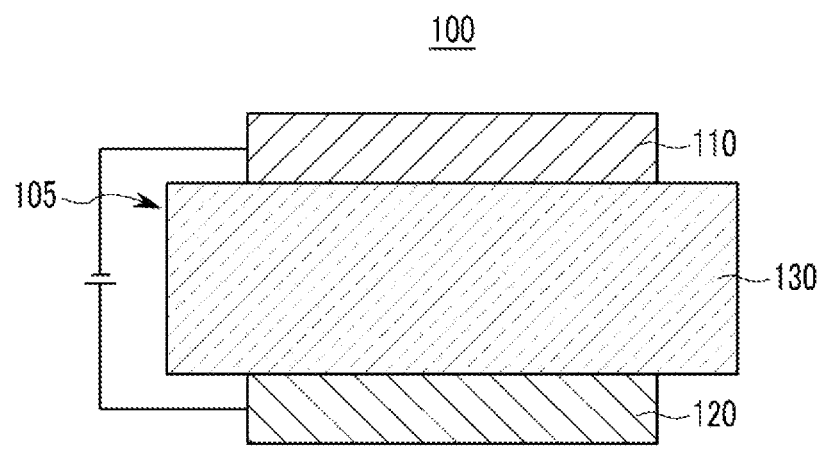
[FIG. 2]
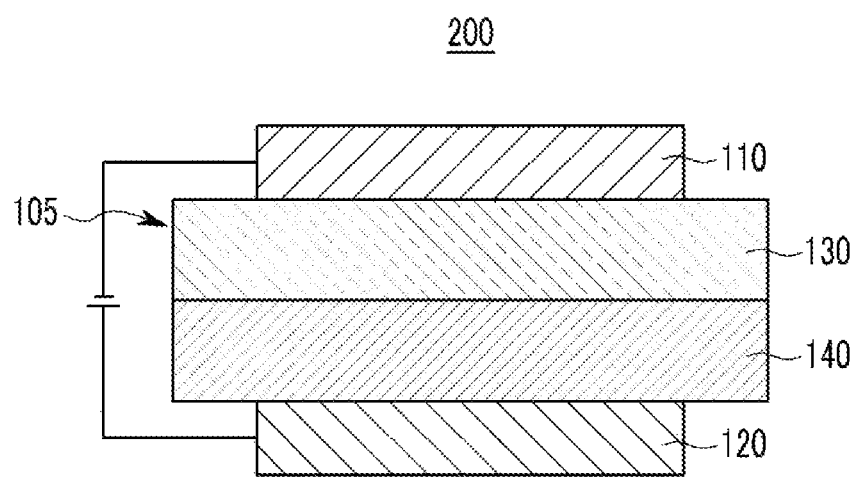

COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

Korean Patent Application No. 10-2020-0047580, filed on Apr. 20, 2020, in the Korean Intellectual Property Office, and entitled: "Composition for Organic Optoelectronic Device, Organic Optoelectronic Device and Display Device," is incorporated by reference herein in its entirety.

BACKGROUND

1. Field

Embodiments relate to a composition for an organic optoelectronic device, an organic optoelectronic device, and a display device.

2. Description of the Related Art

An organic optoelectronic device (organic optoelectronic diode) is a device capable of converting electrical energy and optical energy to each other.

Organic optoelectronic devices may be divided into two types according to a principle of operation. One type includes a photoelectric device that generates electrical energy by separating excitons formed by light energy into electrons and holes, and transferring the electrons and holes to different electrodes, respectively and another type includes light emitting device that generates light energy from electrical energy by supplying voltage or current to the electrodes.

Examples of the organic optoelectronic device may include an organic photoelectric device, an organic light emitting diode, an organic solar cell, and an organic photo conductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a composition for an organic optoelectronic device, the composition including a first compound represented by Chemical Formula 1 and a second compound represented by a combination of Chemical Formula 2 and Chemical Formula 3:

[Chemical Formula 1]

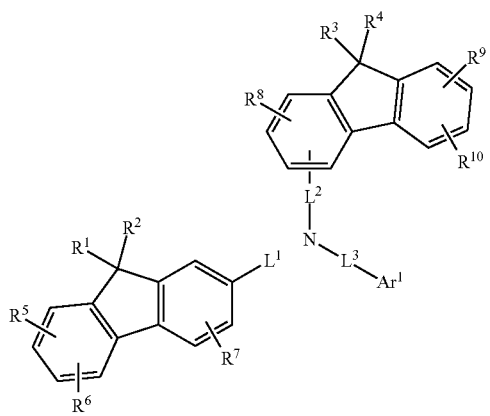

wherein, in Chemical Formula 1, $Ar^1$ is a substituted or unsubstituted C6 to C30 aryl group, a substituted or unsubstituted C2 to C30 heteroaryl group, or a combination thereof, $L^1$ to $L^3$ are each independently a single bond or a substituted or unsubstituted C6 to C30 arylene group, $R^1$ to $R^4$ are each independently a substituted or unsubstituted C1 to C30 alkyl group, a substituted or unsubstituted C6 to C30 aryl group, or a combination thereof, $R^5$ to $R^{10}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof,

[Chemical Formula 2]

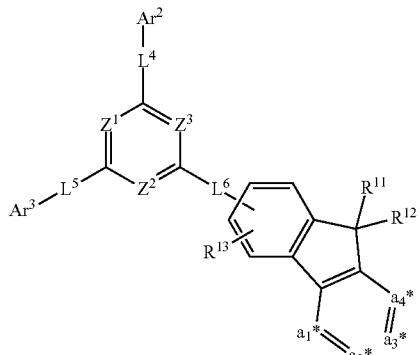

[Chemical Formula 3]

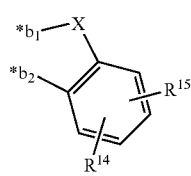

wherein, in Chemical Formula 2 and Chemical Formula 3, a1* to a4* of Chemical Formula 2 are each independently a linking carbon or $CR^a$, provided that a1* and a2*; a2* and a3*; or a3* and a4* of Chemical Formula 2 are linking carbons linked at *b1 and b2 of Chemical Formula 3, $Z^1$ to $Z^3$ are each independently N or $CR^b$, at least one of $Z^1$ to $Z^3$ is N, X is O, S, or $CR^cCR^d$, $Ar^2$ and $Ar^3$ are each independently a substituted or unsubstituted C6 to C30 aryl group, a substituted or unsubstituted C2 to C30 heteroaryl group, or a combination thereof, $L^4$ to $L^6$ are each independently a single bond or a substituted or unsubstituted C6 to C30 arylene group, $R^c$, $R^d$, $R^{11}$, and $R^{12}$ are each independently a substituted or unsubstituted C1 to C30 alkyl group, a substituted or unsubstituted C6 to C30 aryl group, or a combination thereof, and $R^a$, $R^b$, and $R^{13}$ to $R^{15}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

The first compound may be represented by one of Chemical Formula 1-1 to Chemical Formula 1-4:

[Chemical Formula 1-1]

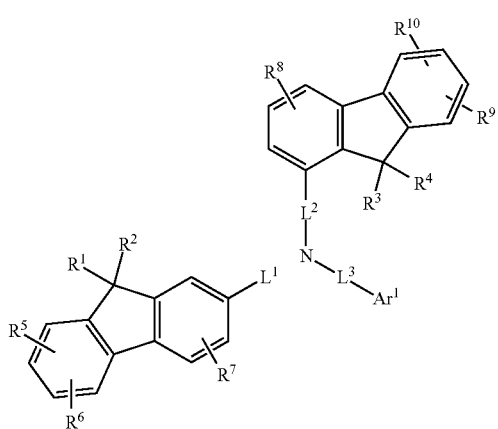

[Chemical Formula 1-2]

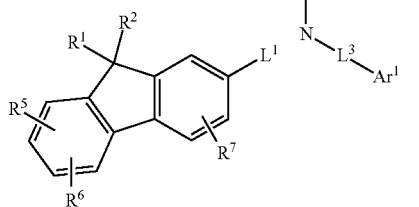

[Chemical Formula 1-3]

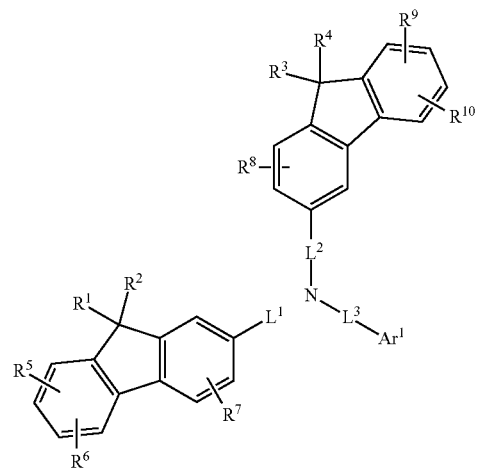

[Chemical Formula 1-4]

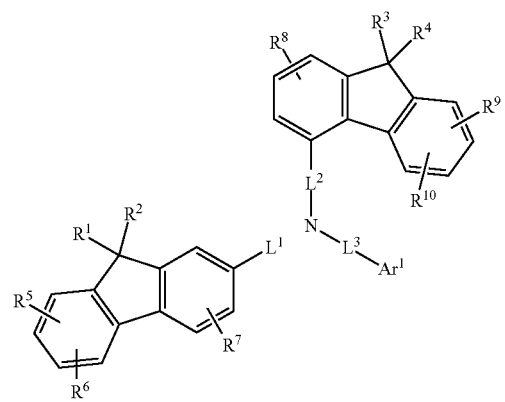

wherein, in Chemical Formulae 1-1 to 1-4, $Ar^1$, $L^1$ to $L^3$, and $R^1$ to $R^{10}$ may be defined the same as those of Chemical Formula 1.

$Ar^1$ in Chemical Formula 1 may be a substituted or unsubstituted phenyl group, a substituted or unsubstituted biphenyl group, or a substituted or unsubstituted naphthyl group.

$Ar^1$ in Chemical Formula 1 may be a substituent of the following Group I:

[Group I]

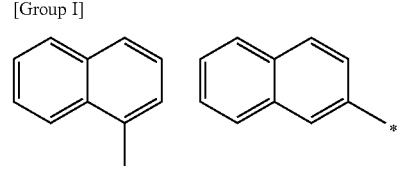

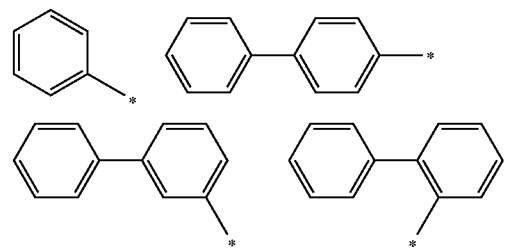

-continued

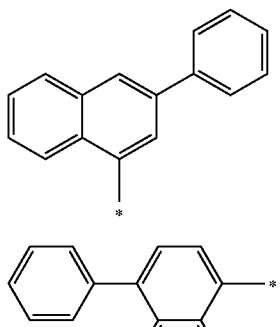

wherein, in Group I, * is a linking point.

The second compound may be represented by Chemical Formula 2A or Chemical Formula 2F:

[Chemical Formula 2A]

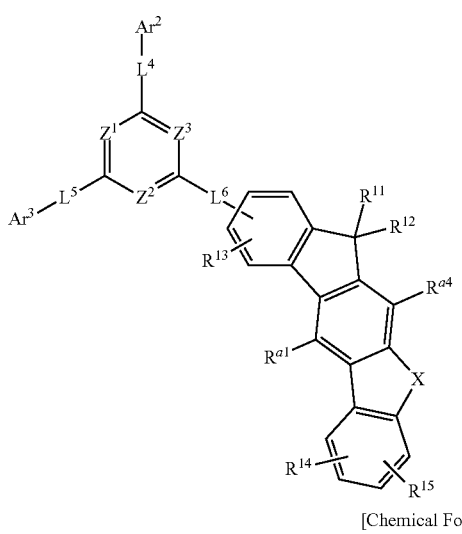

[Chemical Formula 2F]

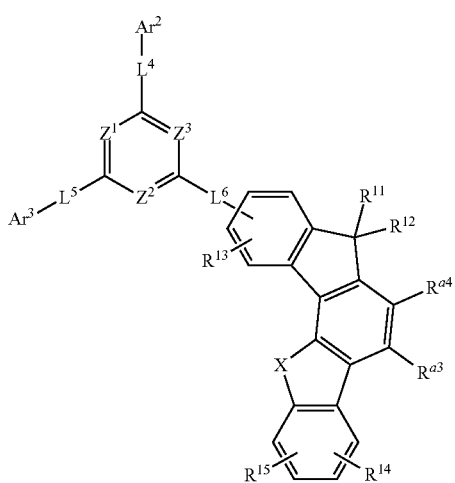

wherein, in Chemical Formula 2A and Chemical Formula 2F, $Z^1$ to $Z^3$, X, $Ar^2$, $Ar^3$, $L^4$ to $L^6$, and $R^{11}$ to $R^{15}$ may be defined the same as those of Chemical Formulae 2 and 3, $R^{a1}$ to $R^{a4}$ may be defined the same as $R^a$ of Chemical Formulae 2 and 3.

The second compound may be represented by Chemical Formula 2A-2, Chemical Formula 2F-2, or Chemical Formula 2F-4:

[Chemical Formula 2A-2]

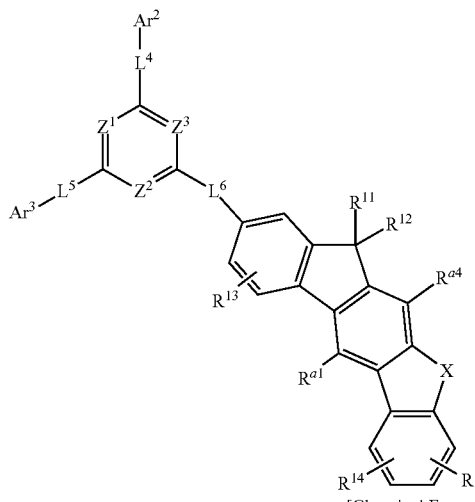

[Chemical Formula 2F-2]

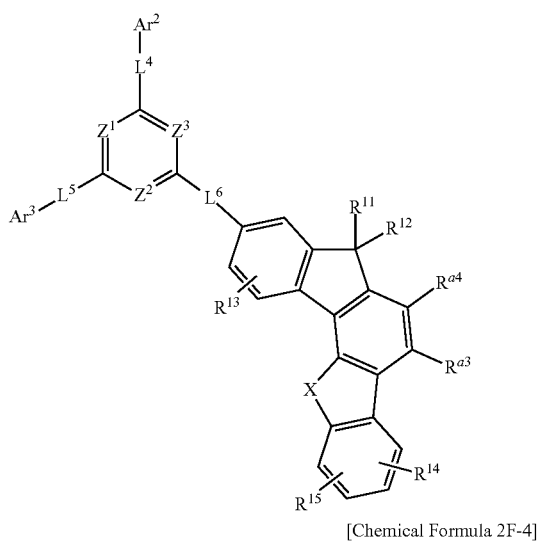

[Chemical Formula 2F-4]

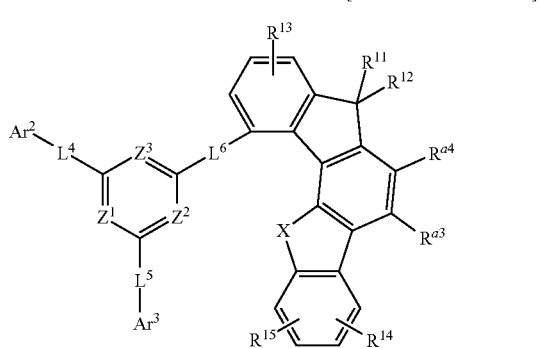

wherein, in Chemical Formula 2A-2, Chemical Formula 2F-2, and Chemical Formula 2F-4, $Z^1$ to $Z^3$, X, $Ar^2$, $Ar^3$, $L^4$ to $L^6$, $R^{11}$ to $R^{15}$ and $R^{a1}$ to $R^{a4}$ may be defined the same as those of Chemical Formula 2A and Chemical Formula 2F.

$Ar^2$ and $Ar^3$ of Chemical Formula 2 may be each independently a substituted or unsubstituted phenyl group, a substituted or unsubstituted biphenyl group, a substituted or unsubstituted naphthyl group, a substituted or unsubstituted triphenylene group, a substituted or unsubstituted fluorenyl group, a substituted or unsubstituted benzofluorenyl group, a substituted or unsubstituted dibenzofuranyl group, or a substituted or unsubstituted dibenzothiophenyl group.

The first compound may be represented by Chemical Formula 1-3a, and the second compound may be represented by Chemical Formula 2A-2, Chemical Formula 2F-2, or Chemical Formula 2F-4:

[Chemical Formula 1-3a]

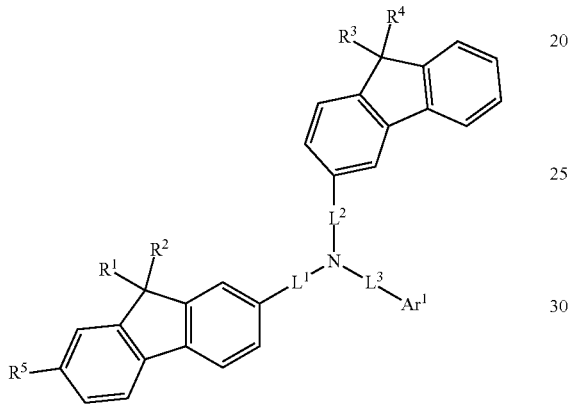

wherein, in Chemical Formula 1-3a, $Ar^1$ may be a substituted or unsubstituted C6 to C30 aryl group, a substituted or unsubstituted C2 to C30 heteroaryl group, or a combination thereof, $R^1$ to $R^4$ may be each independently a substituted or unsubstituted methyl group or a substituted or unsubstituted phenyl group, $R^5$ may be hydrogen or a substituted or unsubstituted phenyl group, and $L^1$ to $L^3$ may be each independently a single bond or a substituted or unsubstituted phenylene group;

[Chemical Formula 2A-2]

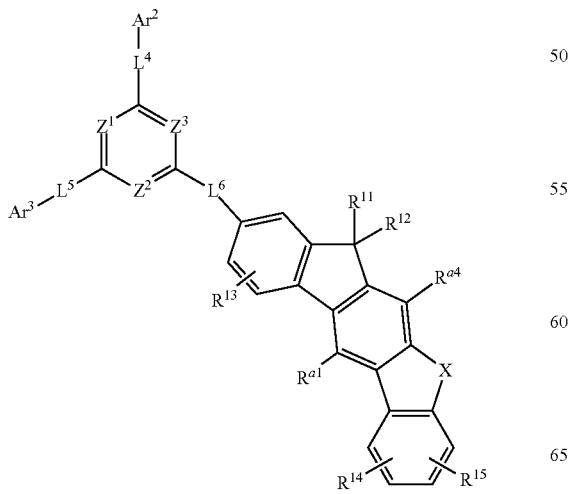

[Chemical Formula 2F-2]

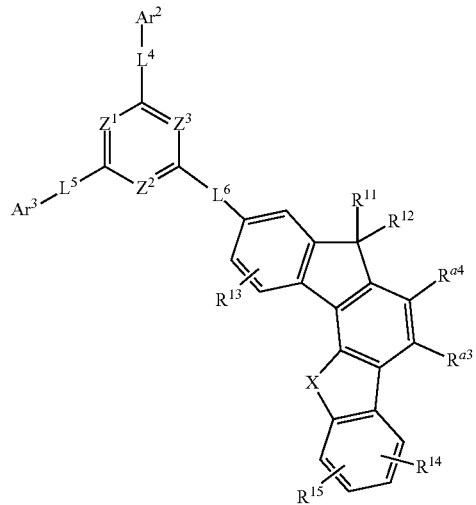

[Chemical Formula 2F-4]

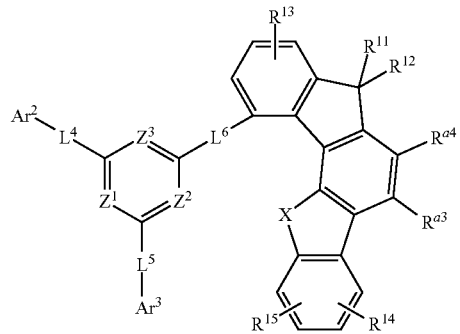

wherein, in Chemical Formula 2A-2, Chemical Formula 2F-2, and Chemical Formula 2F-4, X may be O, S, or $CR^cCR^d$, $Ar^2$ and $Ar^3$ may be each independently a substituted or unsubstituted phenyl group, a substituted or unsubstituted naphthyl group, or a substituted or unsubstituted fluorenyl group, R, $R^d$, $R^{11}$, and $R^{12}$ may be each independently a substituted or unsubstituted methyl group or a substituted or unsubstituted phenyl group, $L^4$ to $L^6$ may be each independently a single bond or a substituted or unsubstituted phenylene group, and $R^{a3}$, $R^{a4}$, and $R^{13}$ to $R^{15}$ may be hydrogen.

The first compound may be a compound of the following Group 1:
[Group 1]
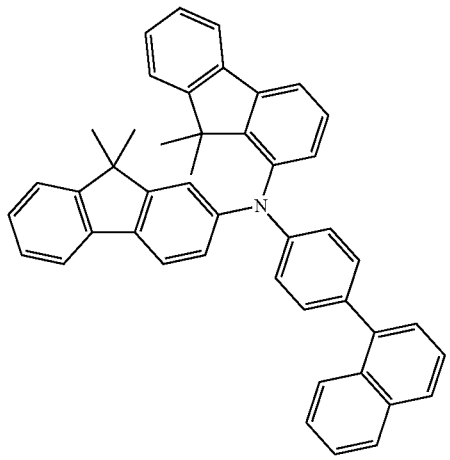
1
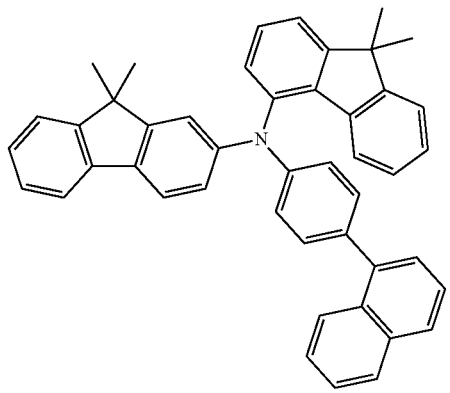
4
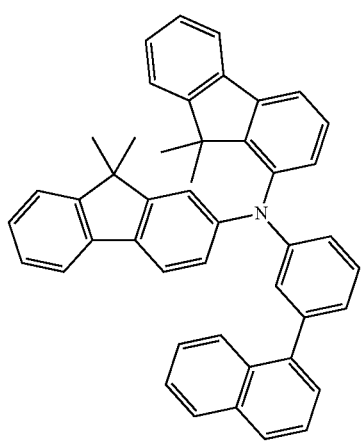
5
2
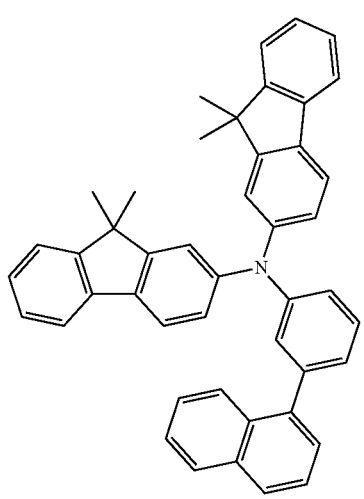
6
3

-continued
7
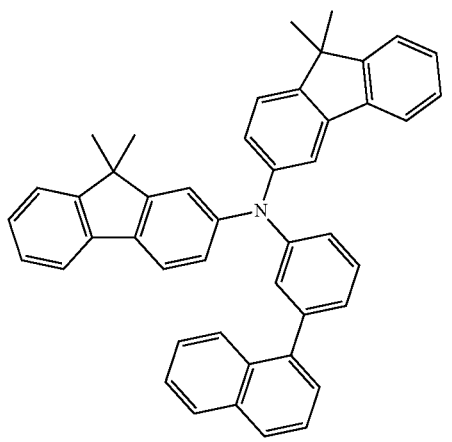
8
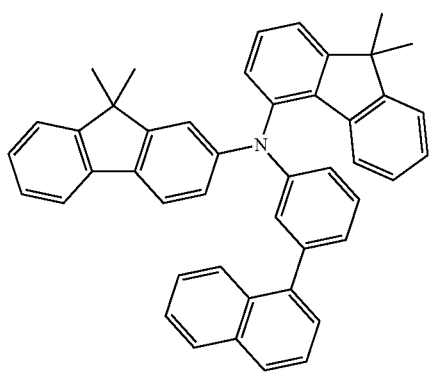
9
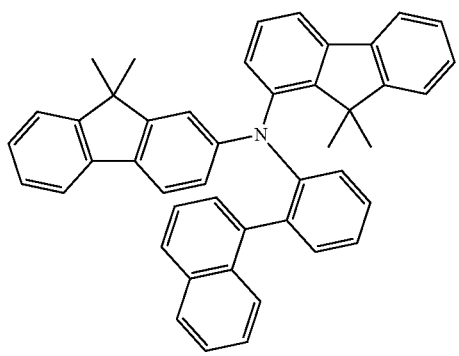
10
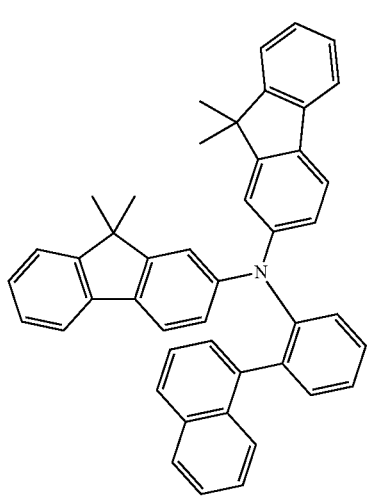
-continued
11
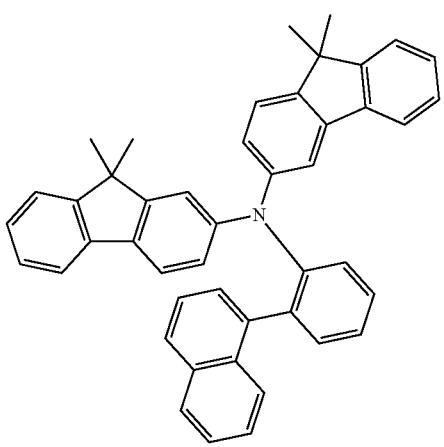
12
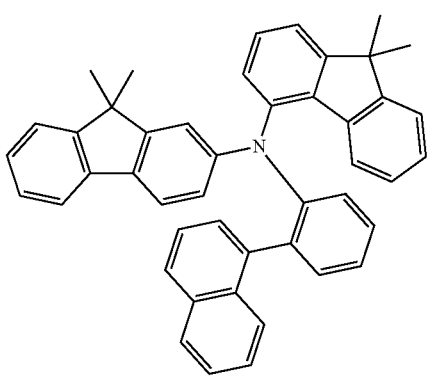
13
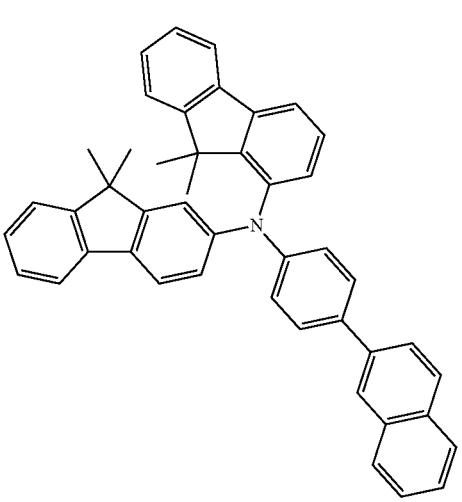

14
-continued
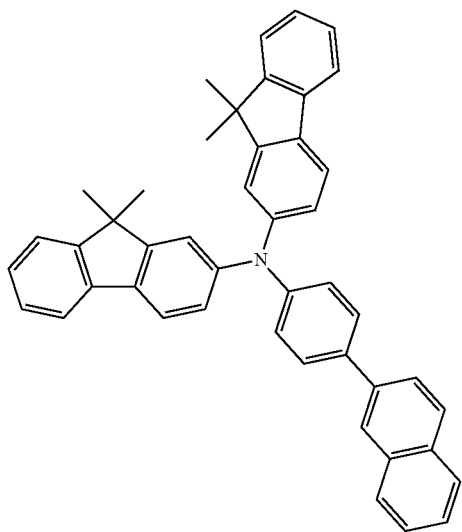
14
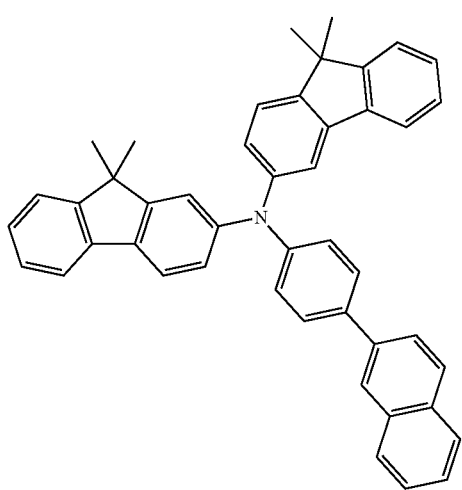
15
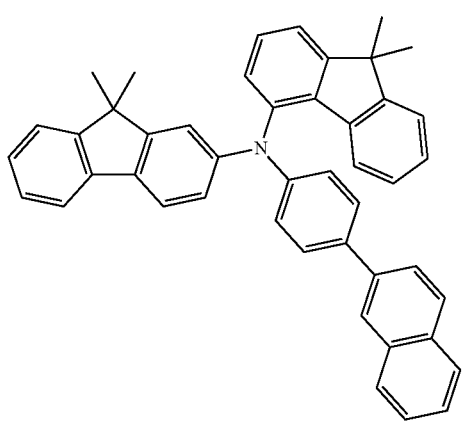
16
-continued
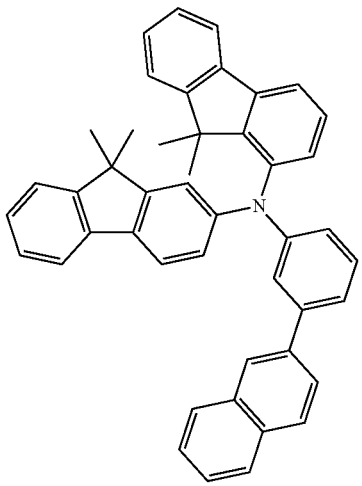
17
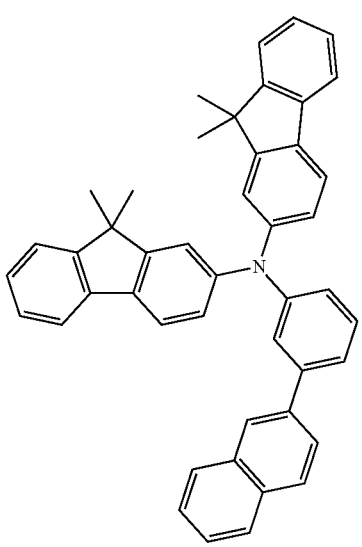
18
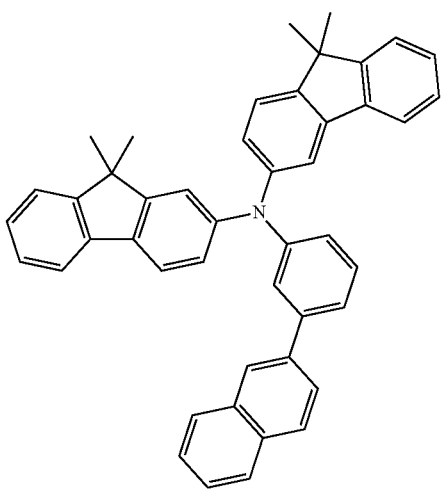
19

20
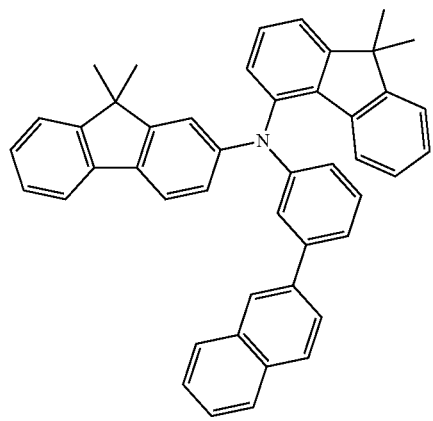
21
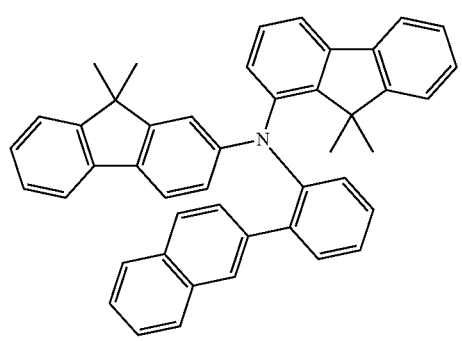
22
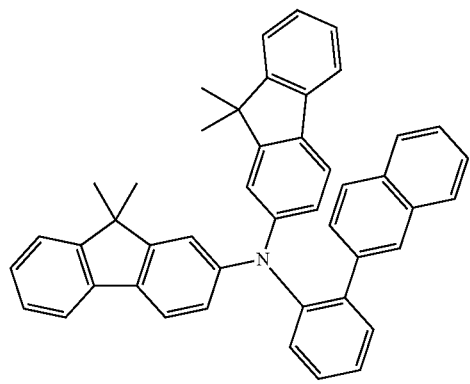
23
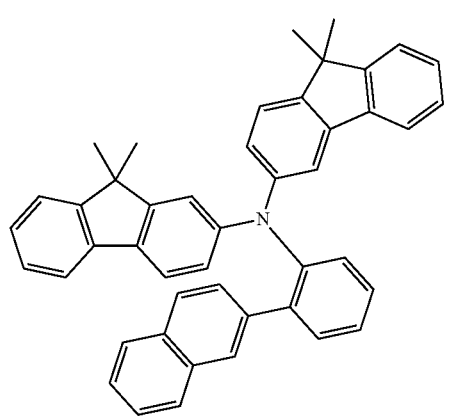
24
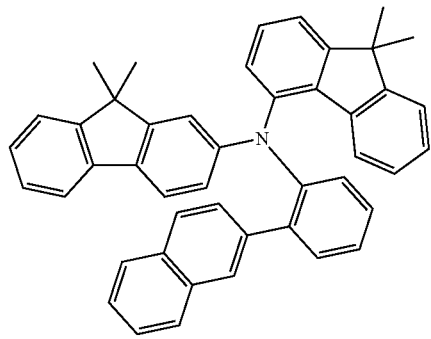
25
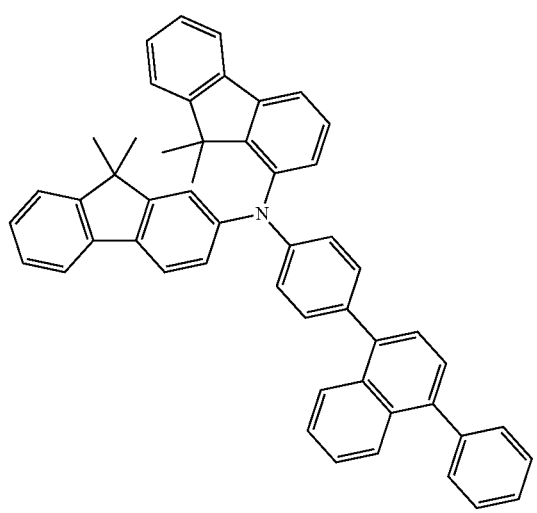
26
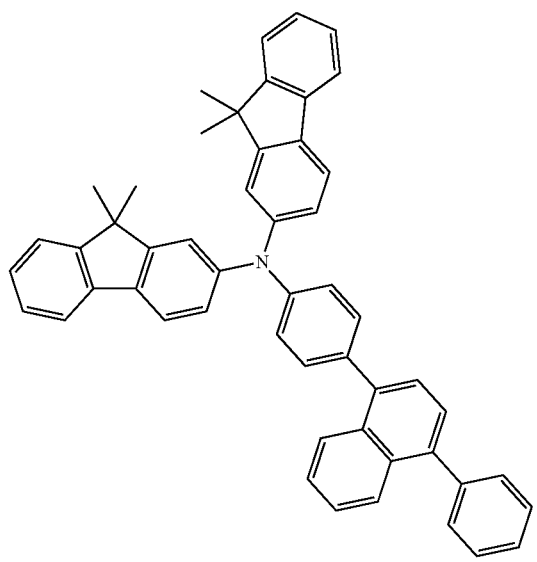

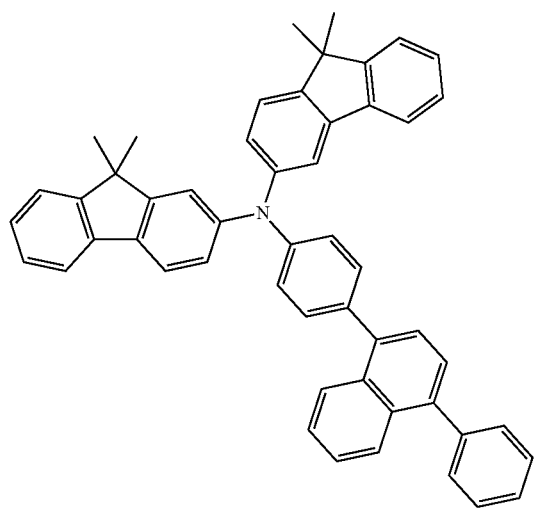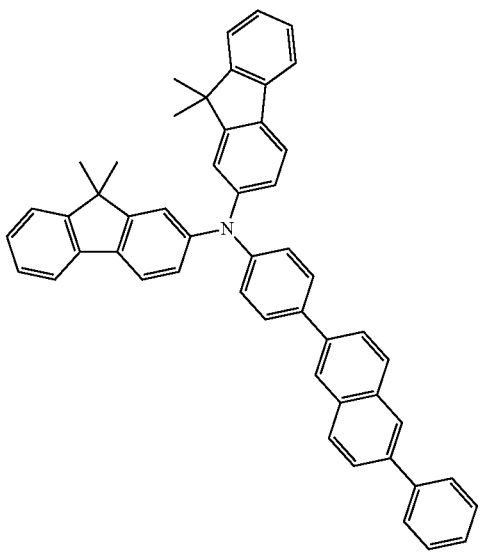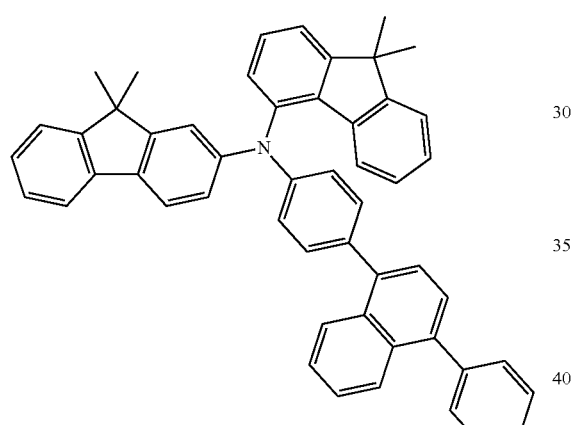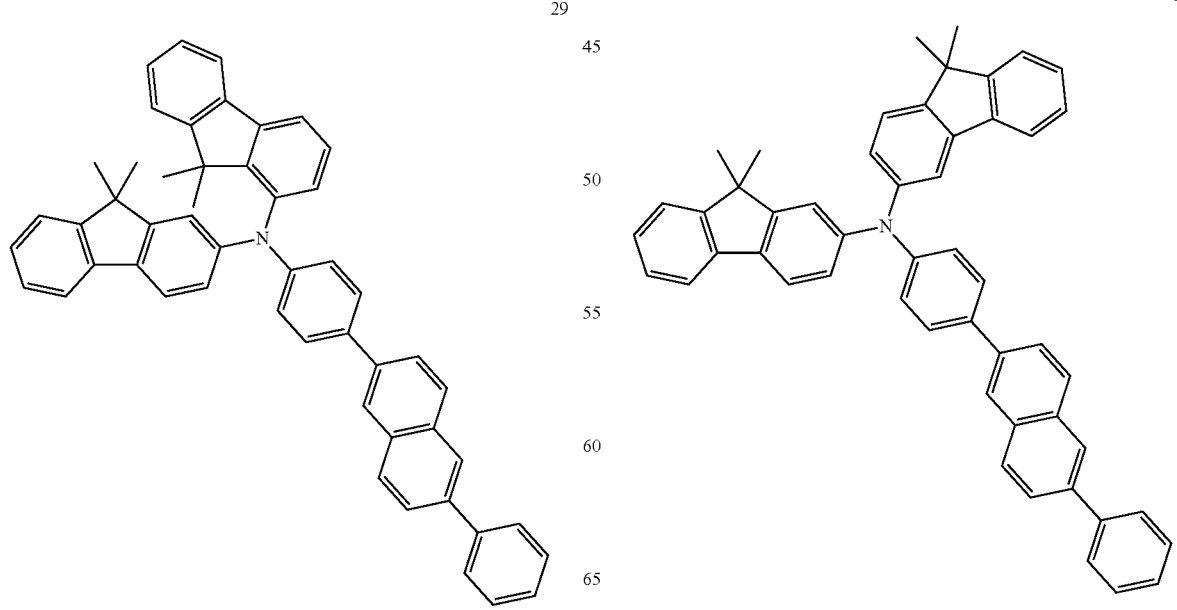

32
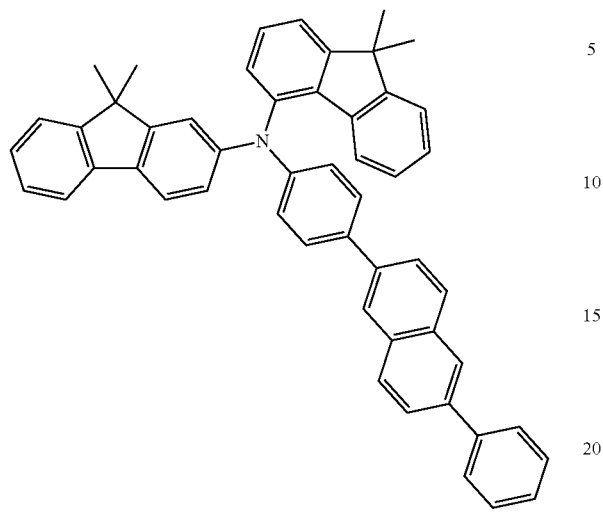
35
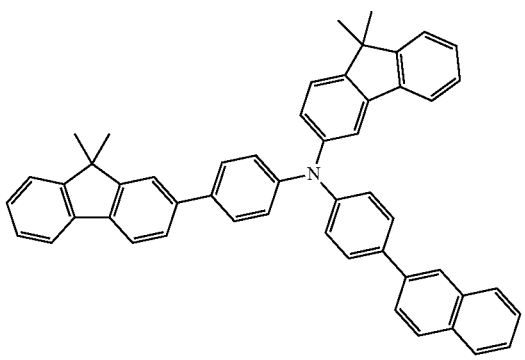
33
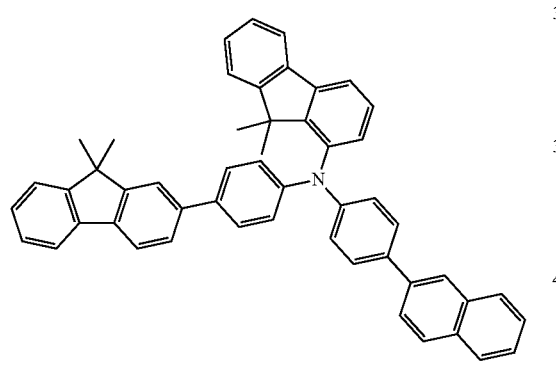
36
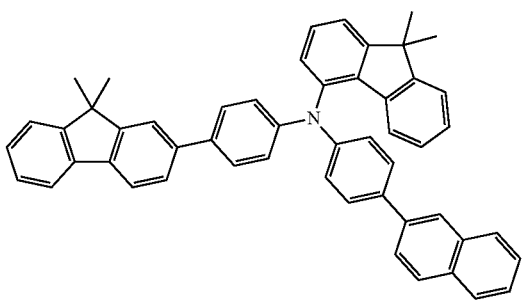
34
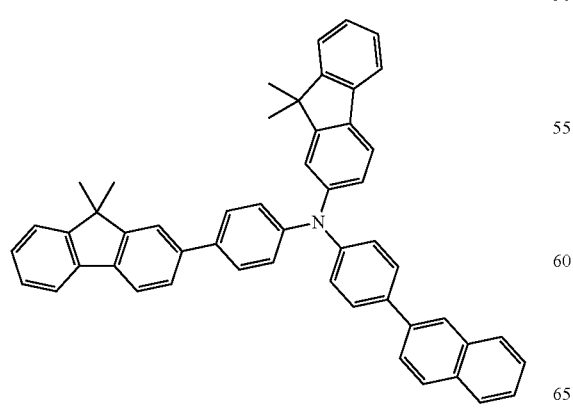
37
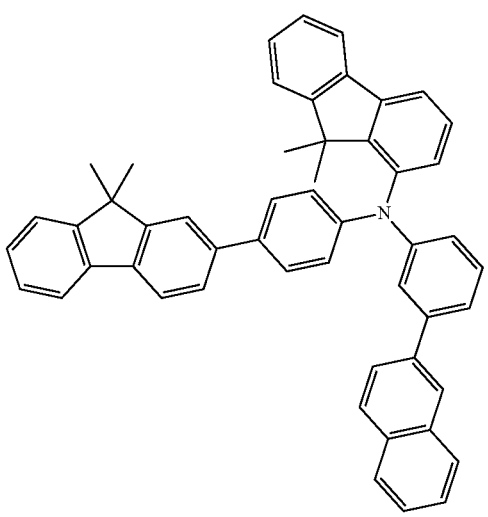

38
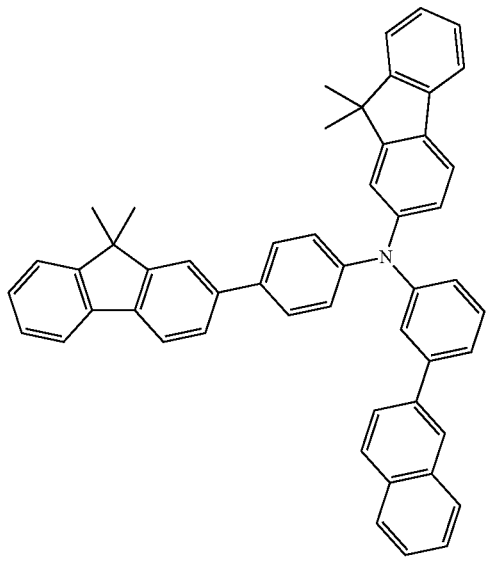
39
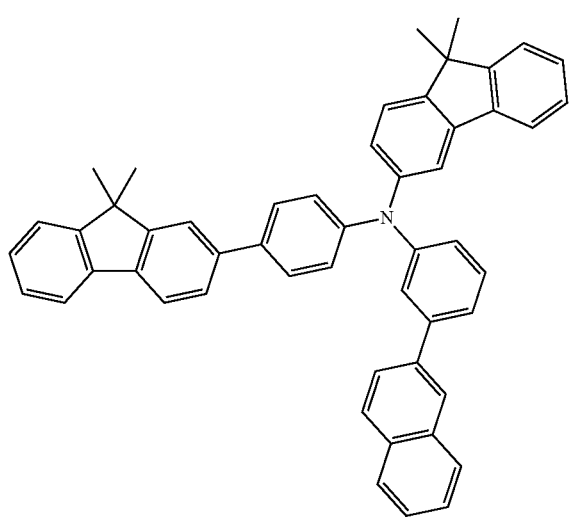
40
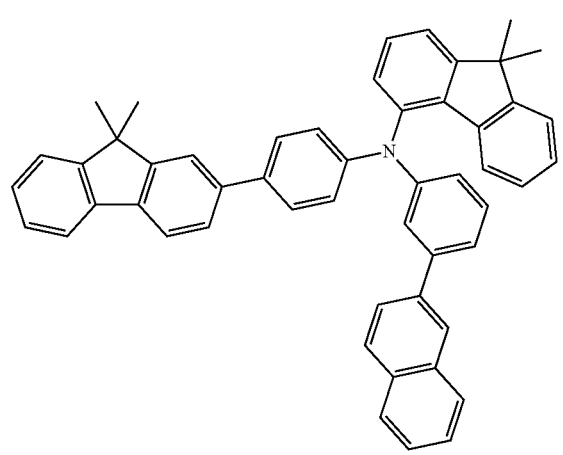
41
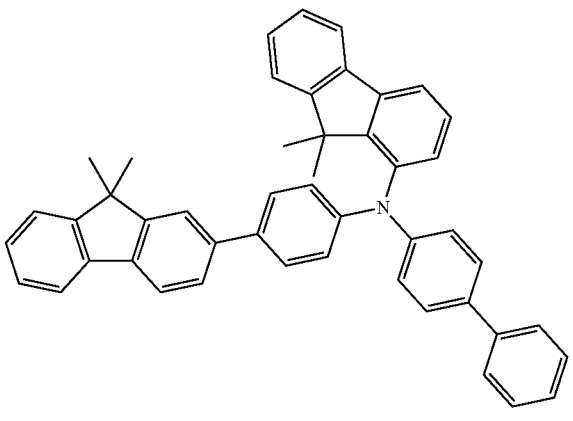
42
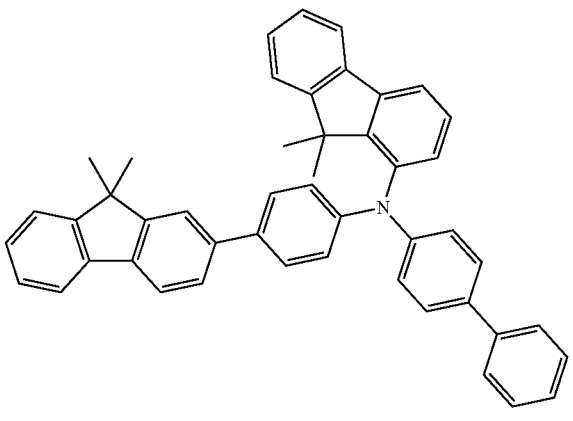
43
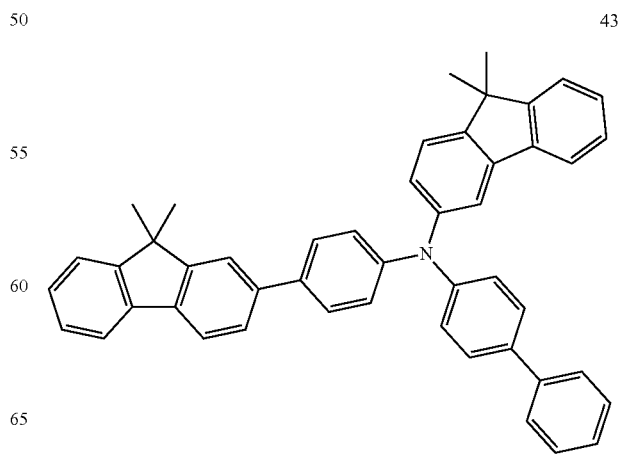

44
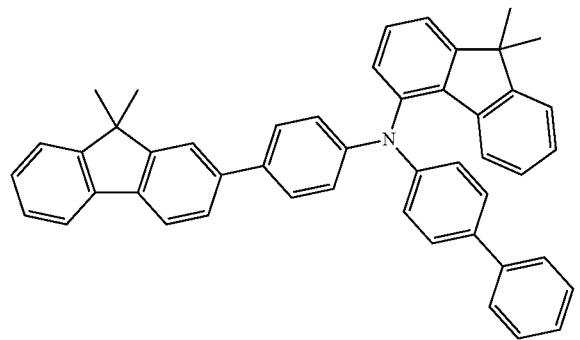
48
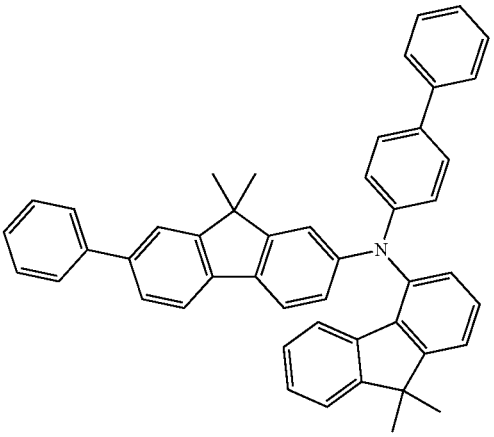
45
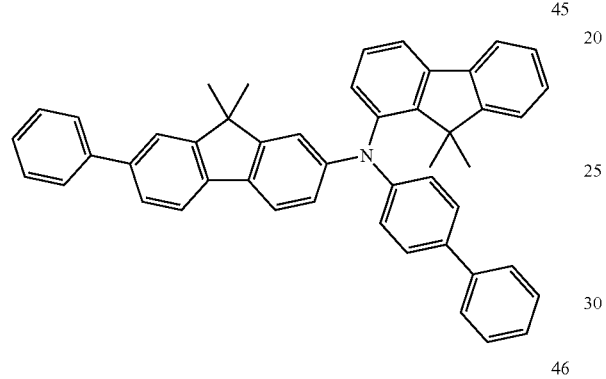
46
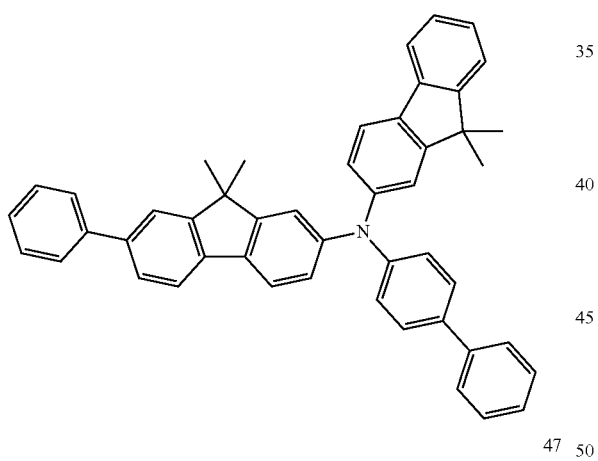
49
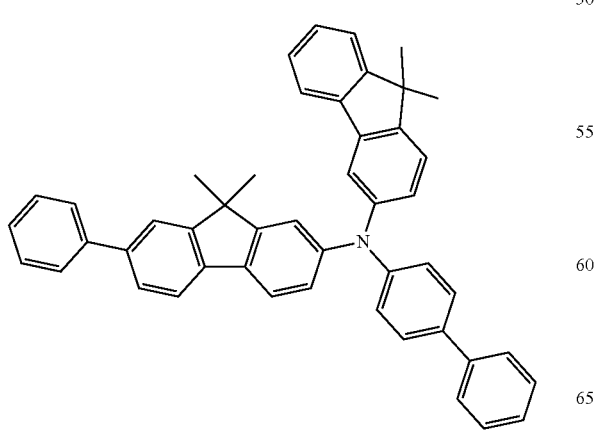
47
50
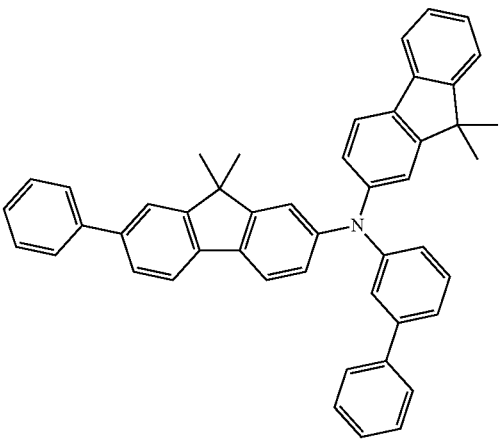

51
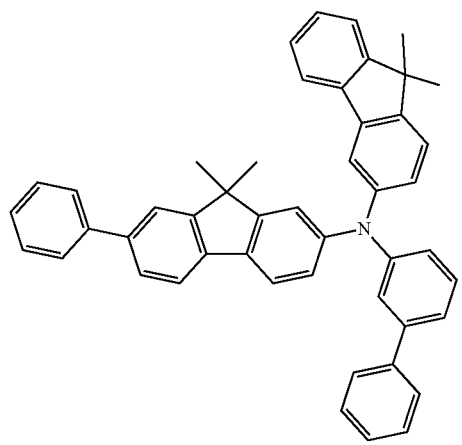
52
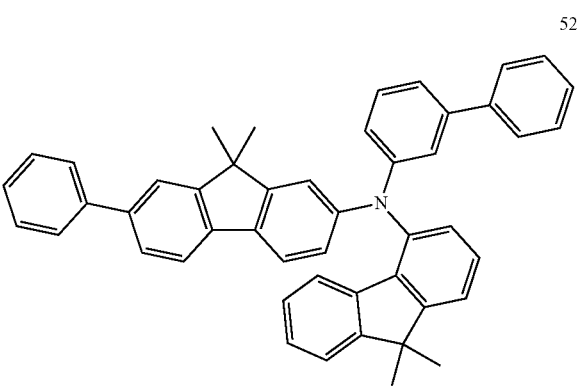
53
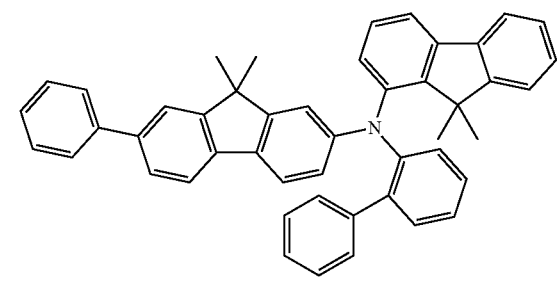
54
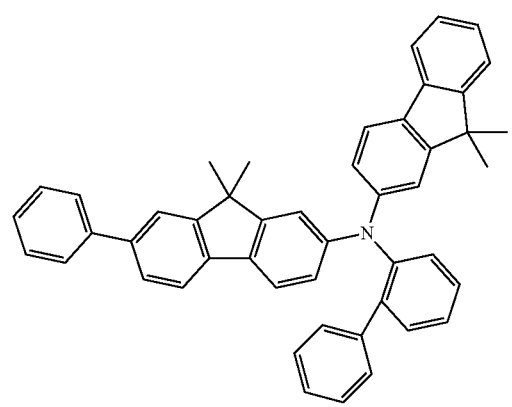
55
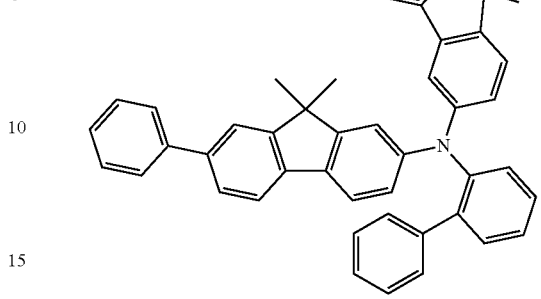
56
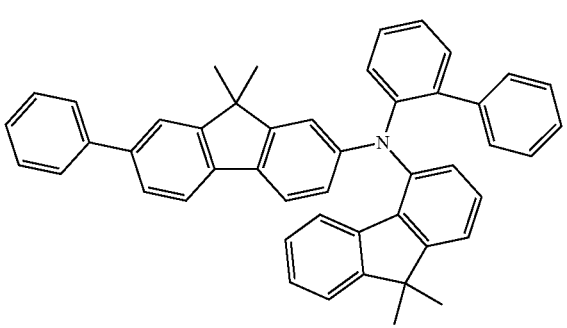
57
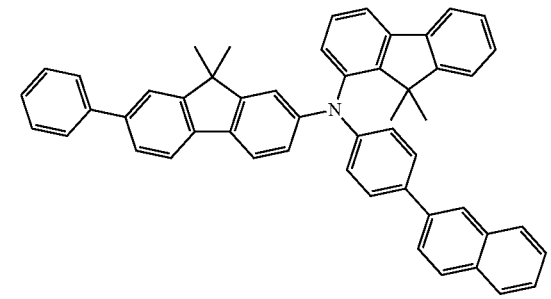
58
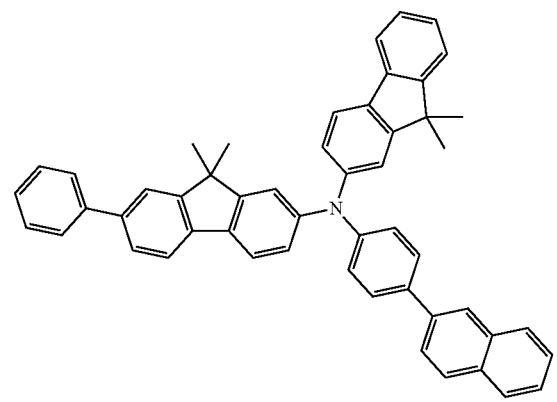

59
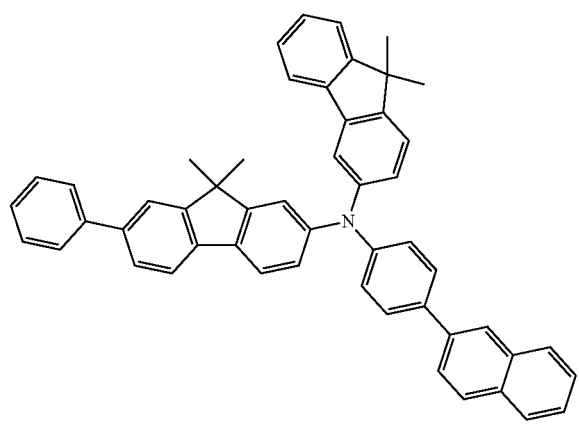
60
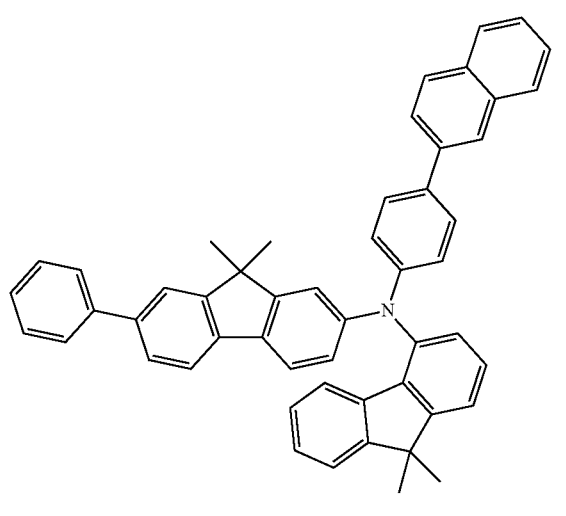
61
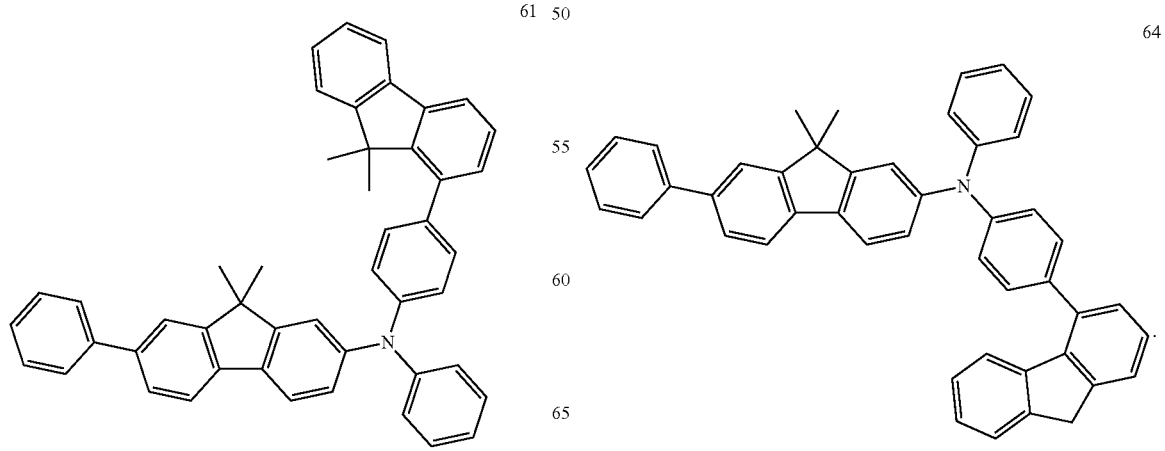
62
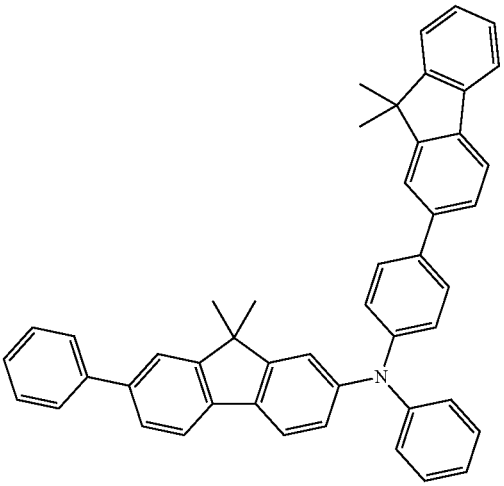
63
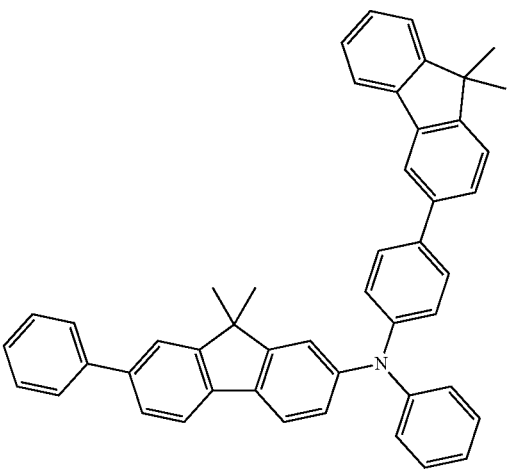
64

The second compound may be a compound of the following Group 2:
[Group 2]
81
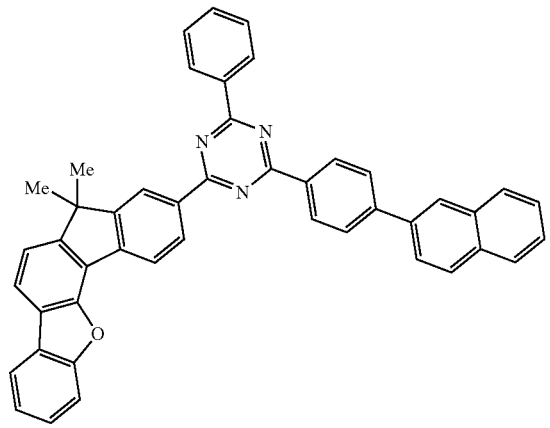
82
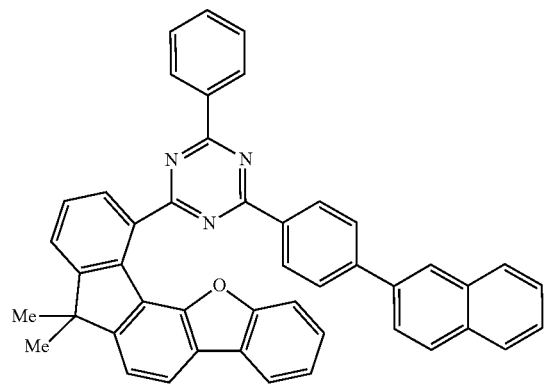
83
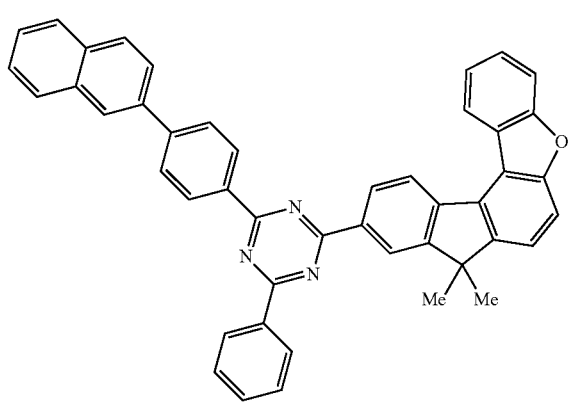
84
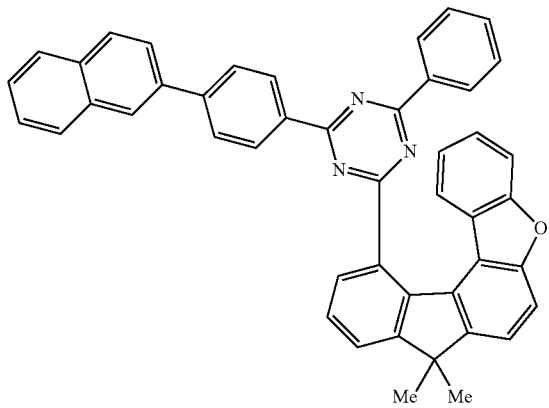
85
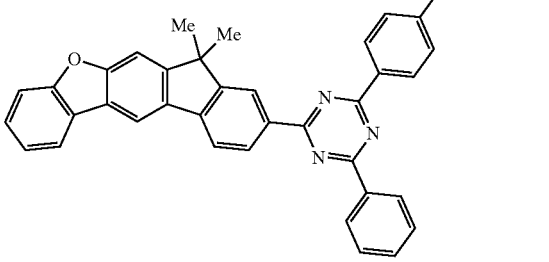
86
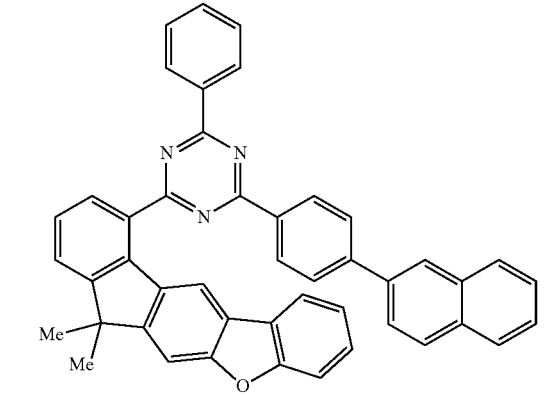
87
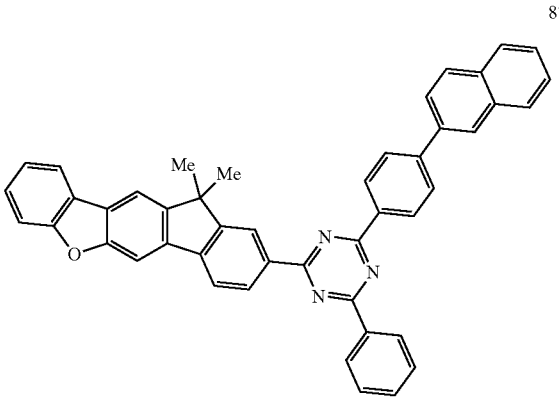

88
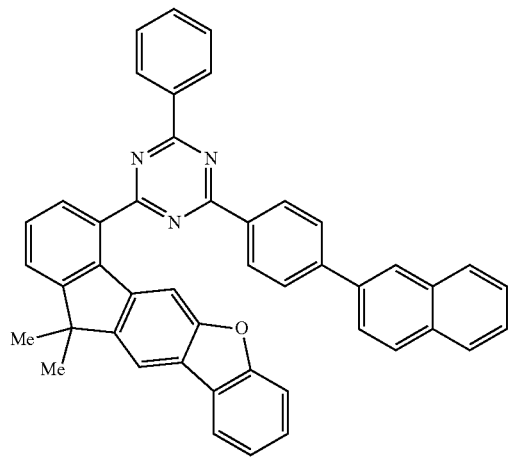
89
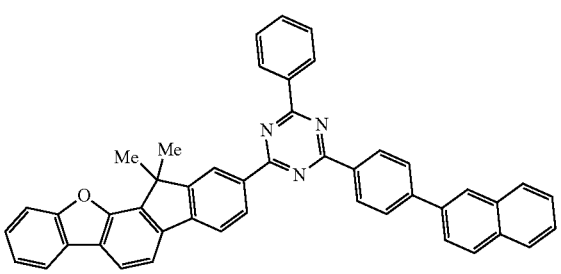
90
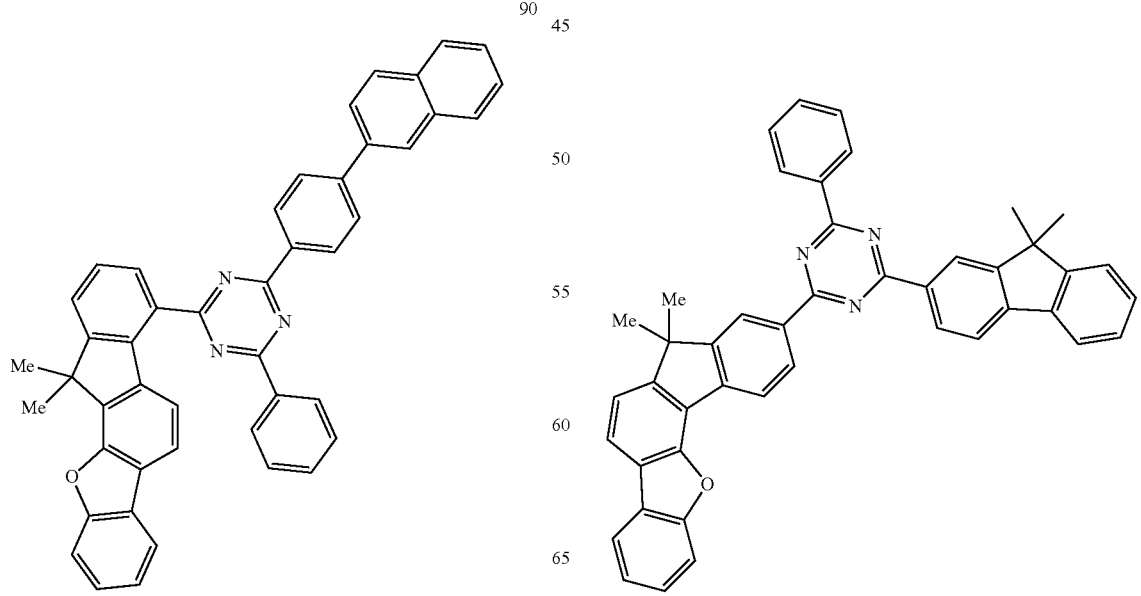
91
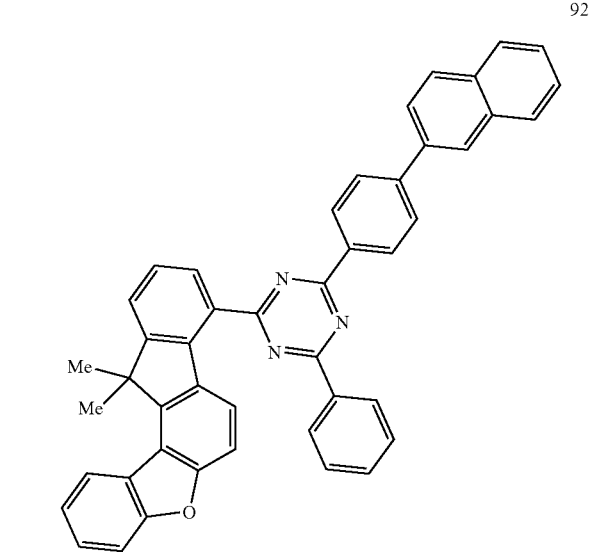
92
93

94

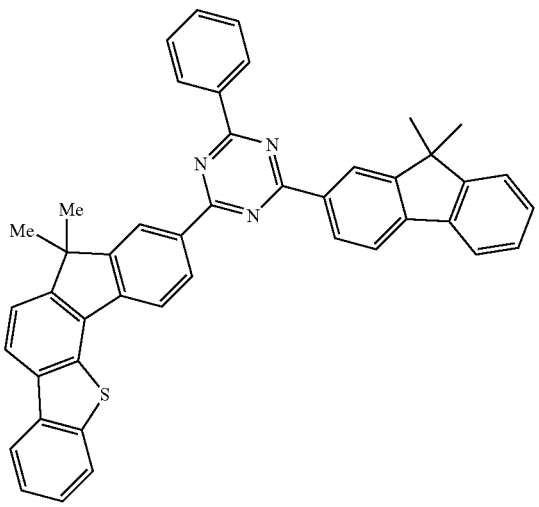

95

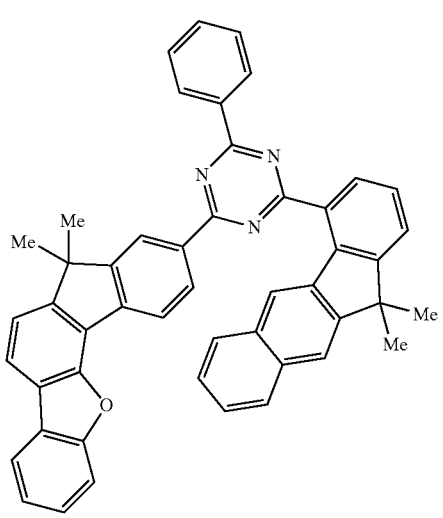

96

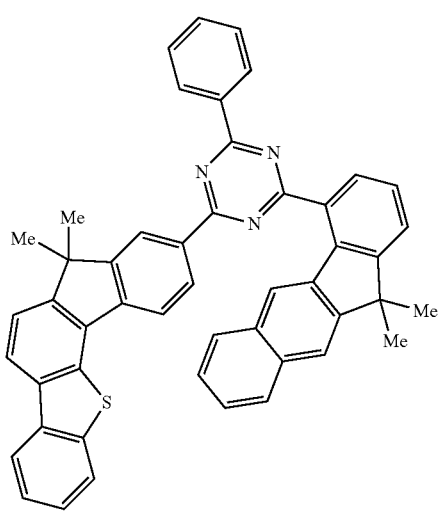

97

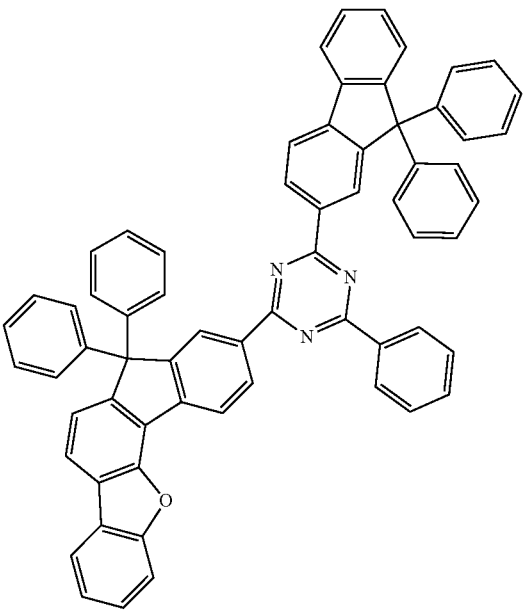

98

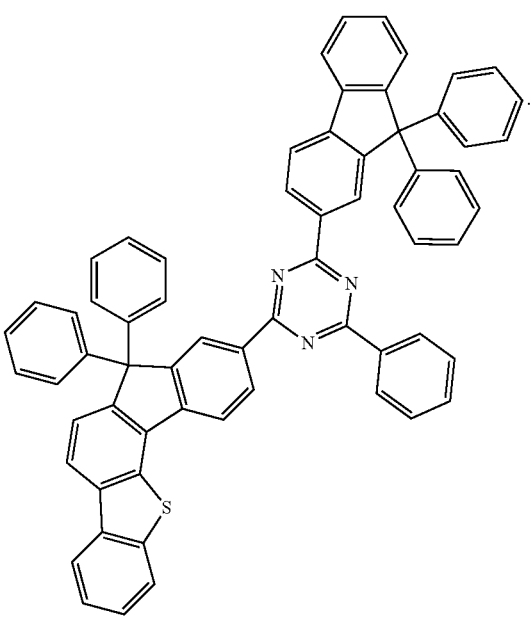

The embodiments may be realized by providing an organic optoelectronic device including an anode and a cathode facing each other, and at least one organic layer between the anode and the cathode, wherein the at least one organic layer includes a light emitting layer, and the light emitting layer includes the composition for an organic optoelectronic device according to an embodiment.

The composition for an organic optoelectronic device may be a host in the light emitting layer.

The composition for an organic optoelectronic device may include the first compound and the second compound in a weight ratio of about 90:10 to about 40:60.

The embodiments may be realized by providing a display device including the organic optoelectronic device according to an embodiment.

BRIEF DESCRIPTION OF THE DRAWINGS

Features will be apparent to those of skill in the art by describing in detail exemplary embodiments with reference to the attached drawings in which:

FIGS. 1 and 2 are cross-sectional views of an organic light emitting diode according to embodiments.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout. As used herein, the term "or" is not an exclusive term, e.g., "A or B" would include A, B, or A and B.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples, "substituted" refers to replacement of at least one hydrogen of a substituent or a compound by deuterium, a C1 to C20 alkyl group, a C6 to C30 aryl group, or a cyano group. In addition, in specific examples, "substituted" refers to replacement of at least one hydrogen of a substituent or a compound by deuterium, a C1 to C5 alkyl group, a C6 to C18 aryl group, or a cyano group. In addition, in specific examples, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, when a definition is not otherwise provided, "hetero" refers to one including one to three heteroatoms selected from N, O, S, P, and Si, and remaining carbons in one functional group.

As used herein, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a composition for an organic optoelectronic device according to an embodiment is described.

The composition for an organic optoelectronic device according to an embodiment may include a first compound for an organic optoelectronic device represented by Chemical Formula 1 and a second compound for an organic optoelectronic device represented by a combination of Chemical Formula 2 and Chemical Formula 3.

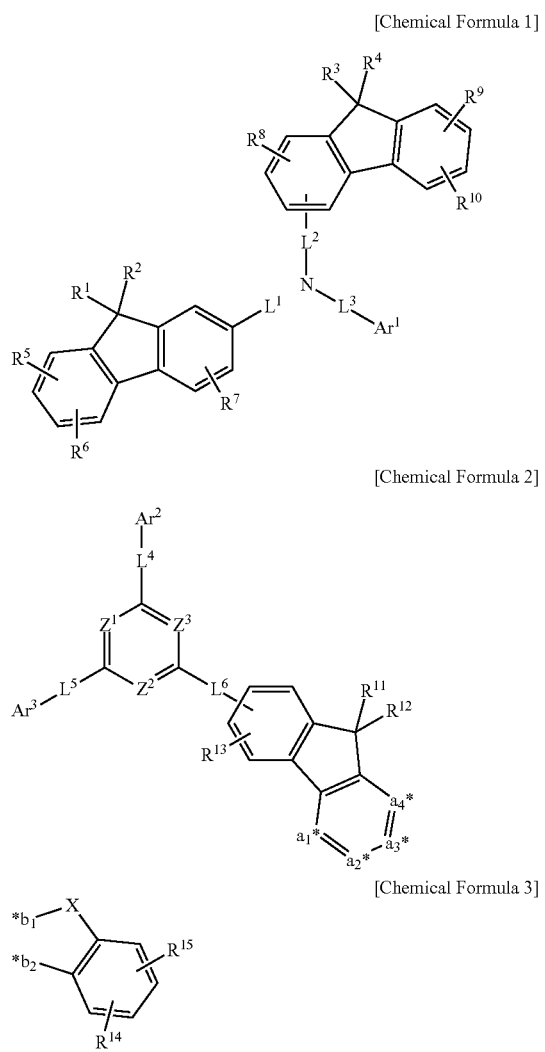

[Chemical Formula 1]

[Chemical Formula 2]

[Chemical Formula 3]

In Chemical Formula 1, $Ar^1$ may be or may include, e.g., a substituted or unsubstituted C6 to C30 aryl group, a substituted or unsubstituted C2 to C30 heteroaryl group, or a combination thereof.

$L^1$ to $L^3$ may each independently be or include, e.g., a single bond or a substituted or unsubstituted C6 to C30 arylene group.

$R^1$ to $R^4$ may each independently be or include, e.g., a substituted or unsubstituted C1 to C30 alkyl group, a substituted or unsubstituted C6 to C30 aryl group, or a combination thereof.

$R^5$ to $R^{10}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

In Chemical Formula 2 and Chemical Formula 3, a1* to a4* of Chemical Formula 2 may each independently be, e.g., a linking carbon or $CR^a$. As used herein, the term "linking carbon" refers to a shared carbon at which fused rings are linked.

*b1 and *b2 of Chemical Formula 3 may each be a linking carbon (e.g., the same carbons as two of a1* to a4*).

In an implementation, a1* and a2*; a2* and a3*; or a3* and a4* of Chemical Formula 2 may be linking carbons linked at *b1 and b2 of Chemical Formula 3.

$Z^1$ to $Z^3$ may each independently be, e.g., N or $CR^b$, and at least one of $Z^1$ to $Z^3$ is N, X may be, e.g., O, S, or $CR^cCR^d$.

$Ar^2$ and $Ar^3$ may each independently be or include, e.g., a substituted or unsubstituted C6 to C30 aryl group, a substituted or unsubstituted C2 to C30 heteroaryl group, or a combination thereof.

$L^4$ to $L^6$ may each independently be or include, e.g., a single bond or a substituted or unsubstituted C6 to C30 arylene group.

$R^c$, $R^d$, $R^{11}$, and $R^{12}$ may each independently be or include, e.g., a substituted or unsubstituted C1 to C30 alkyl group, a substituted or unsubstituted C6 to C30 aryl group, or a combination thereof.

$R^a$, $R^b$, and $R^{13}$ to $R^{15}$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

The first compound represented by Chemical Formula 1 may include two fluorenyl groups on a central amine, and at least one of the two fluorenyl groups may be linked to the amine at the position 2 of the fluorenyl group.

By including the two fluorenyl groups, the hole transport characteristics may be further improved, and low driving and high efficiency performance of an organic optoelectronic device including the same may be realized.

In an implementation, at least one fluorenyl group may be linked to the amine at the position 2, planarity of the molecule may be maintained and the deposition temperature may be increased, so that thermal stability during device manufacture may be improved.

In an implementation, the hole mobility may be increased, a driving voltage and efficiency of the organic light emitting diode including the same may be further improved.

In an implementation, the second compound may include a nitrogen-containing hexagonal or six-membered ring moiety and a fused fluorenyl group.

In an implementation, the LUMO energy band may be effectively expanded by including the nitrogen-containing hexagonal ring moiety, and it is used (e.g., mixed) together with the aforementioned first to help increase a balance between holes and electrons, thereby greatly improving the life-span characteristics of the device including the same.

In an implementation, the deposition temperature may be increased by including the fused fluorenyl group, and an optimum deposition film may be formed by improving film properties during device manufacture.

In an implementation, the first compound may be represented by one of Chemical Formula 1-1 to Chemical Formula 1-4, depending on the substitution position of the fluorenyl group.

[Chemical Formula 1-1]

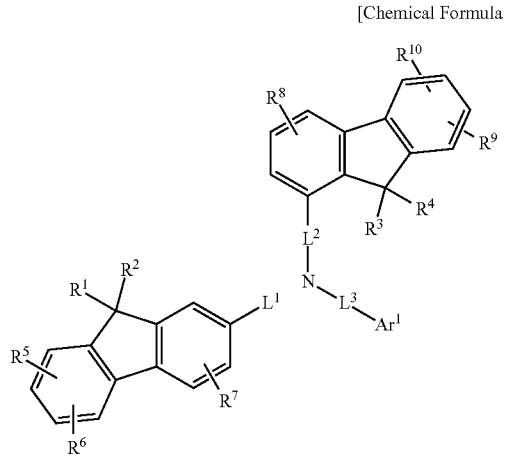

[Chemical Formula 1-2]

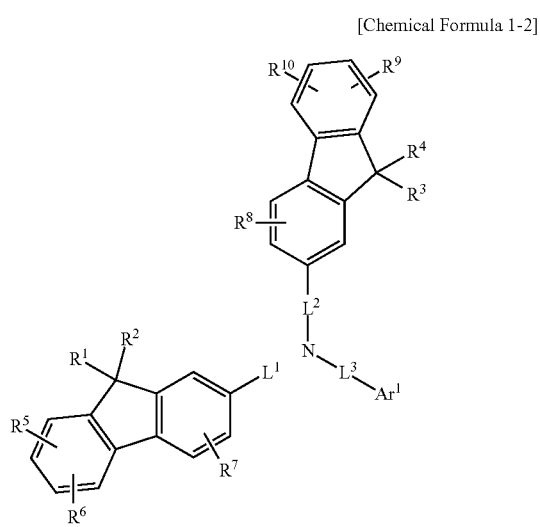

[Chemical Formula 1-3]

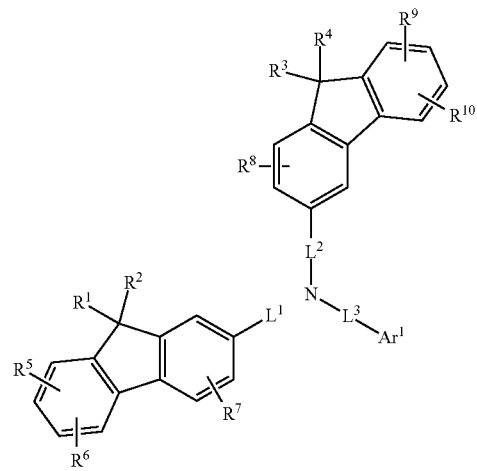

[Chemical Formula 1-4]

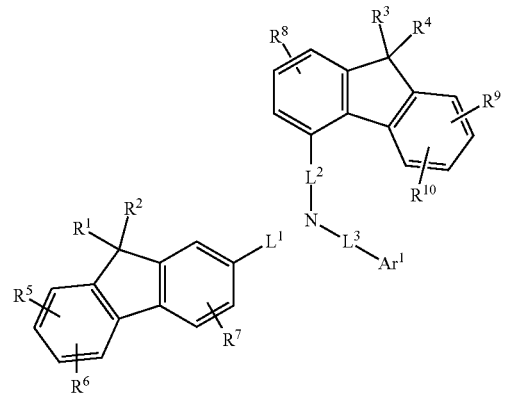

In Chemical Formulas 1-1 to 1-4, $Ar^1$, $L^1$ to $L^3$, and $R^1$ to $R^{10}$ may be defined the same as described above.

In an implementation, the first compound may be represented by one of Chemical Formula 1-2 to Chemical Formula 1-4.

In an implementation, $Ar^1$ of Chemical Formula 1 may be a substituted or unsubstituted phenyl group, a substituted or unsubstituted biphenyl group, or a substituted or unsubstituted naphthyl group.

In an implementation, $Ar^1$ in Chemical Formula 1 may be a substituent of the following Group I.

[Group I]

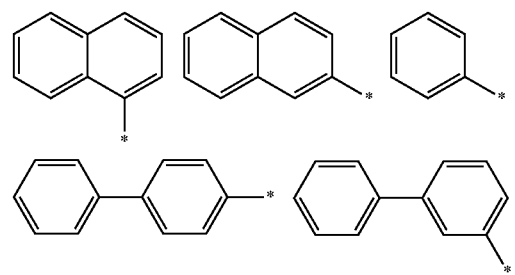

-continued

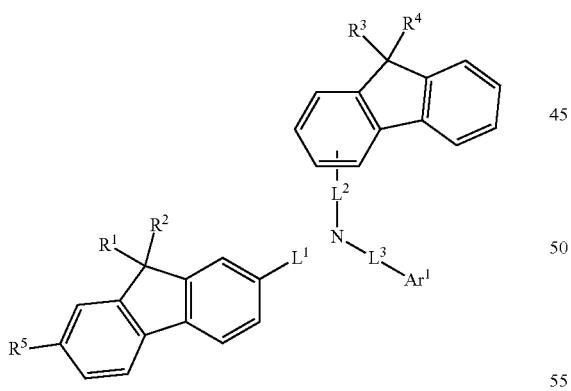

In an implementation, $R^1$ to $R^4$ in Chemical Formula 1 may each independently be a substituted or unsubstituted C1 to C10 alkyl group or a substituted or unsubstituted C6 to C20 aryl group.

In an implementation, $R^1$ to $R^4$ in Chemical Formula 1 may each independently be a substituted or unsubstituted methyl group or a substituted or unsubstituted phenyl group.

In an implementation, $R^5$ to $R^{10}$ in Chemical Formula 1 may each independently be hydrogen or a substituted or unsubstituted C6 to C12 aryl group.

In an implementation, $R^5$ to $R^{10}$ in Chemical Formula 1 may each independently be hydrogen or a phenyl group.

In an implementation, Chemical Formula 1 may be represented by Chemical Formula 1a.

[Chemical Formula 1a]

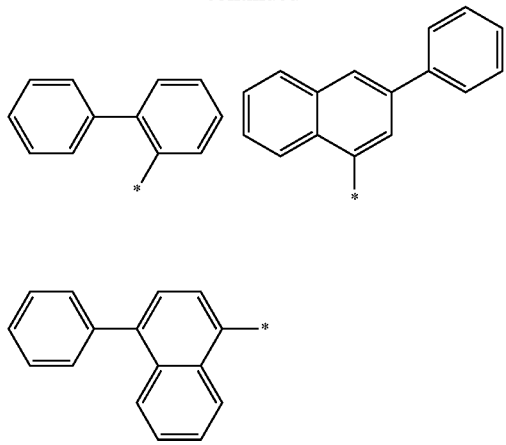

In Chemical Formula 1a, $R^1$ to $R^4$, $L^1$ to $L^3$, and $Ar^1$ may be defined the same as described above, and $R^5$ may be hydrogen or a substituted or unsubstituted phenyl group.

In an implementation, $L^1$ to $L^3$ in Chemical Formula 1 may each independently be, e.g., a single bond or a substituted or unsubstituted phenylene group.

In an implementation, $L^1$ to $L^3$ in Chemical Formula 1 may each independently be, e.g., a single bond, a substituted or unsubstituted meta-phenylene group, or a substituted or unsubstituted para-phenylene group.

In an implementation, the first compound may be a compound of the following Group 1.

[Group 1]

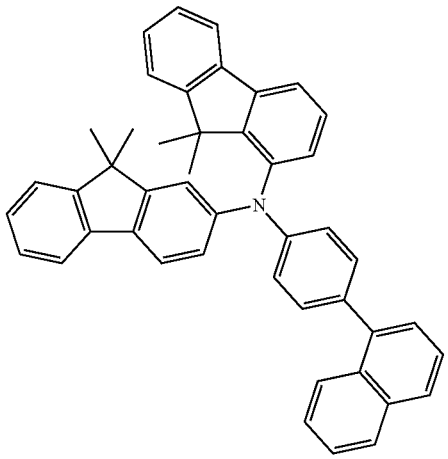

1

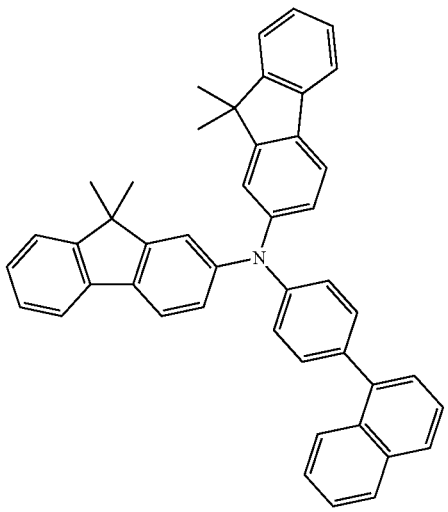

2

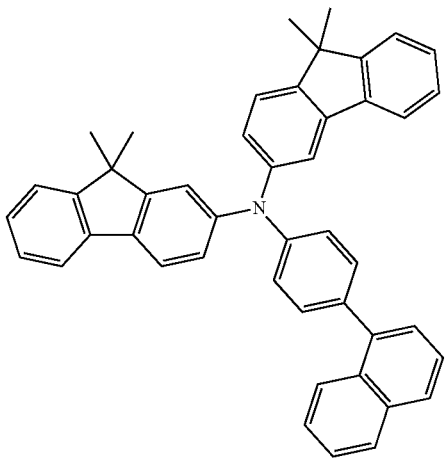

3

4
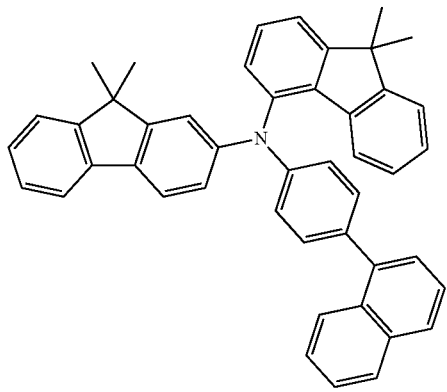
5
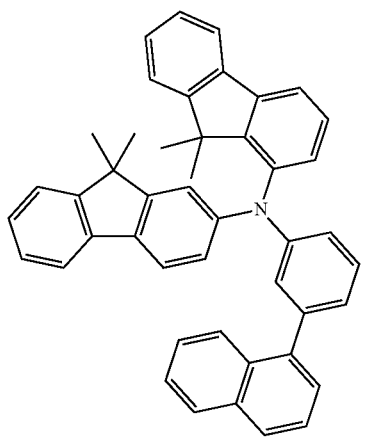
6
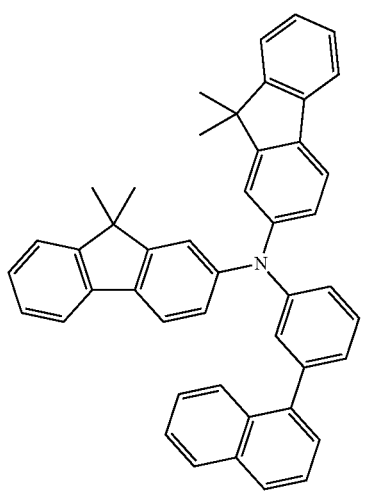
7
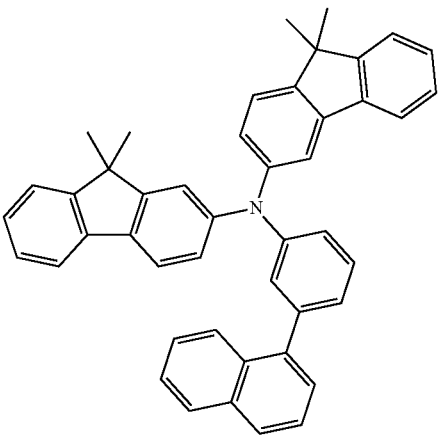
8
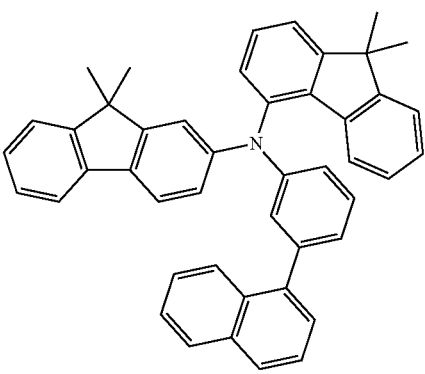
9
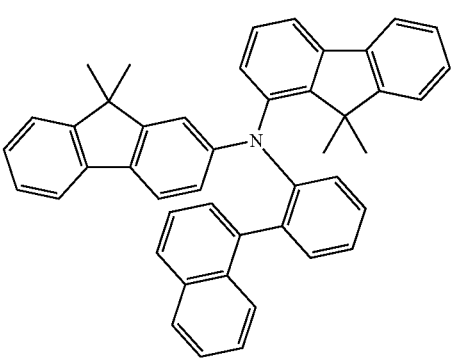
10
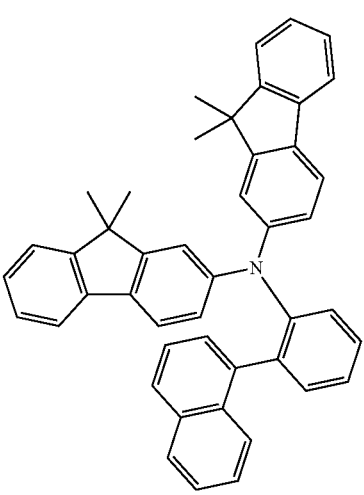

11
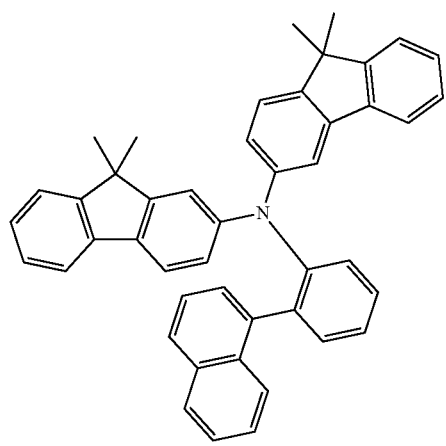
12
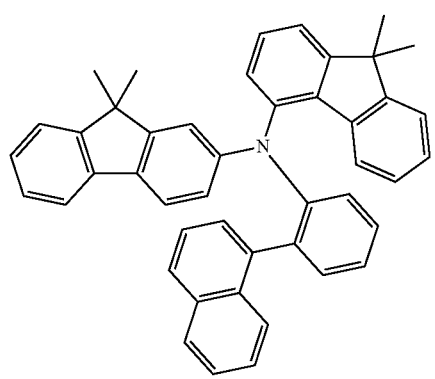
13
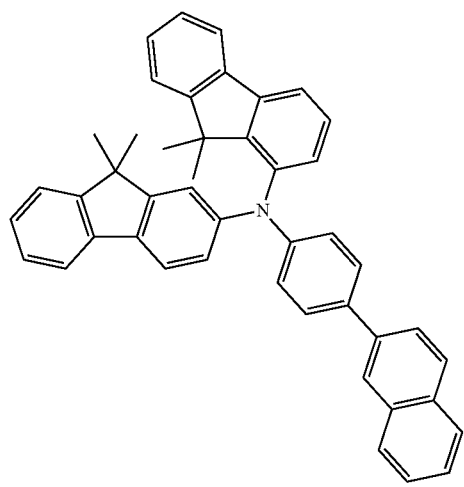
14
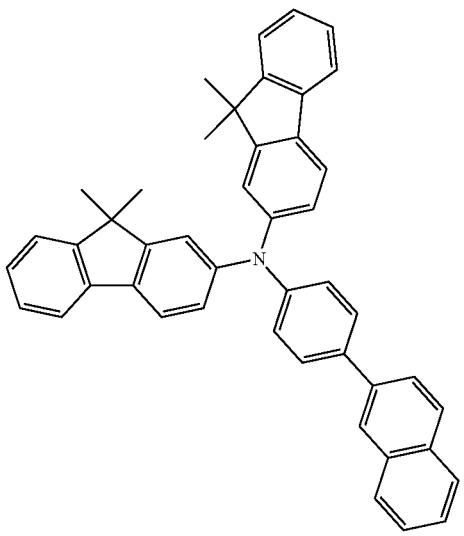
15
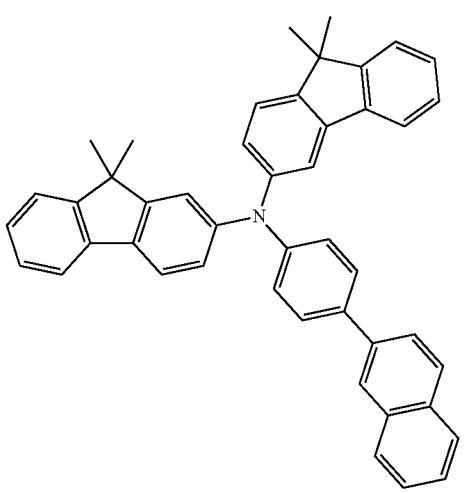
16
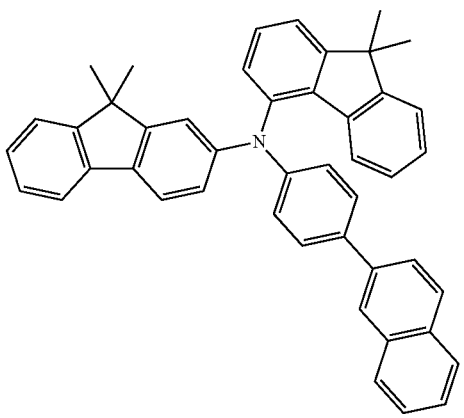

-continued
17
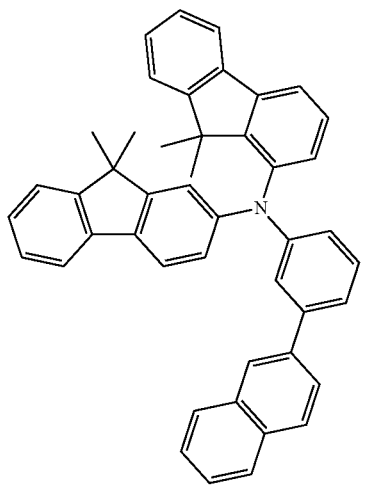
18
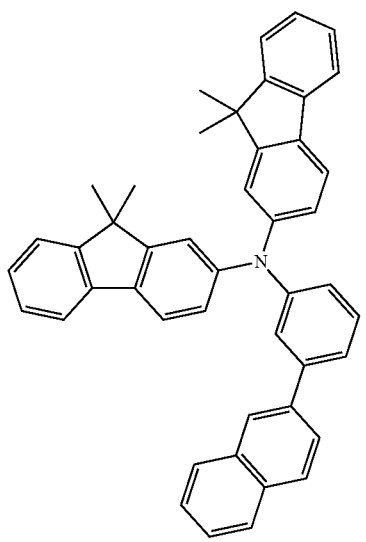
19
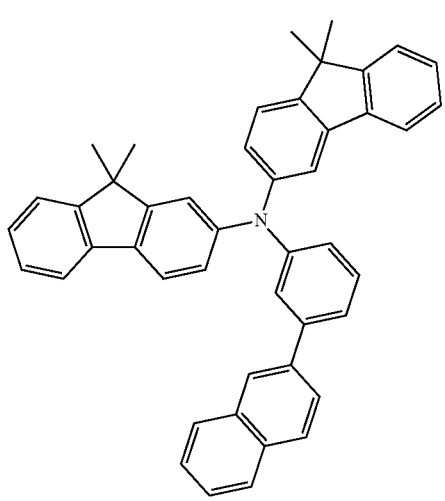
-continued
20
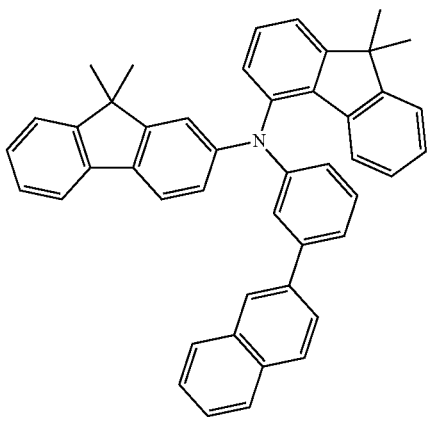
21
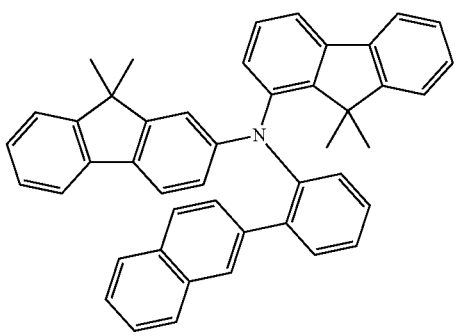
22
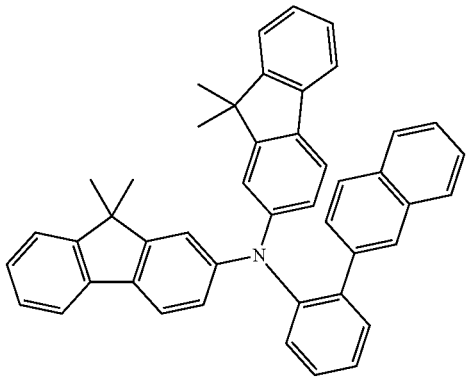
23
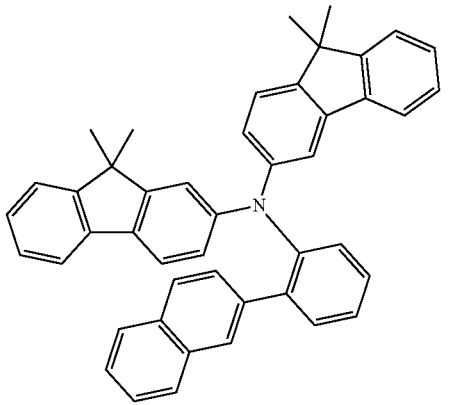

24
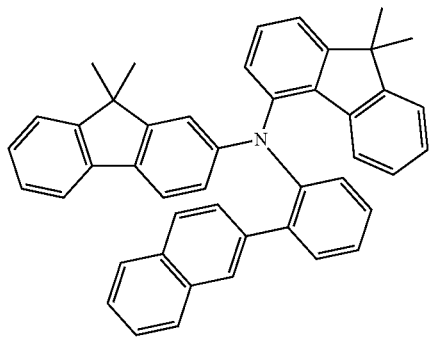
25
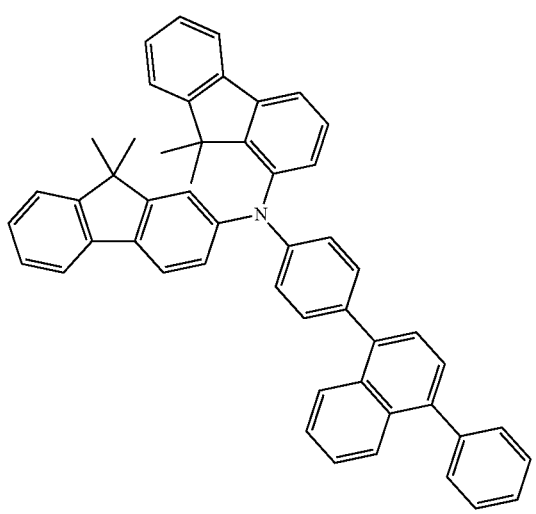
26
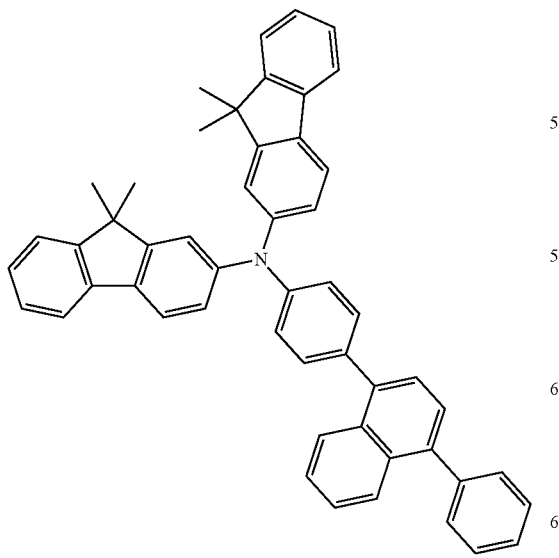
27
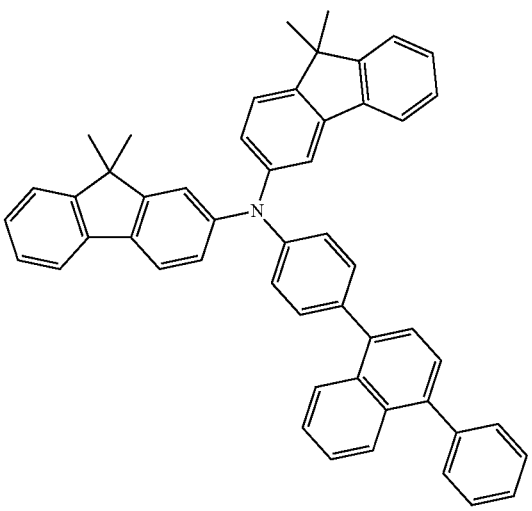
28
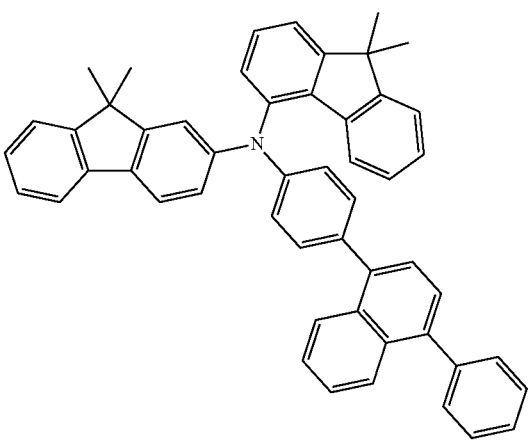
29
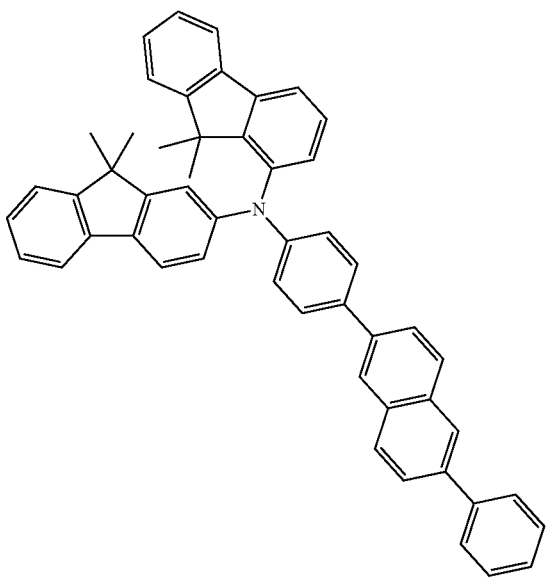

30
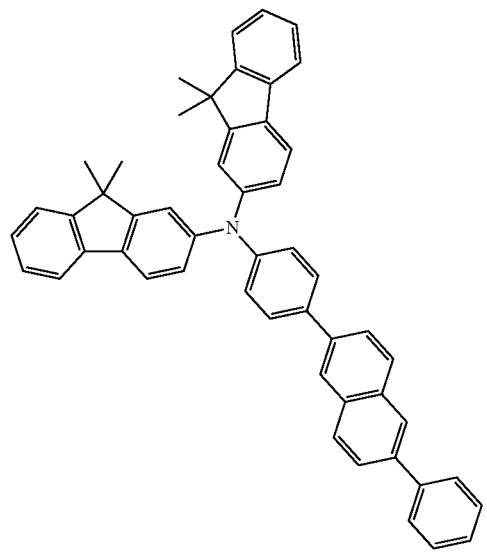
31
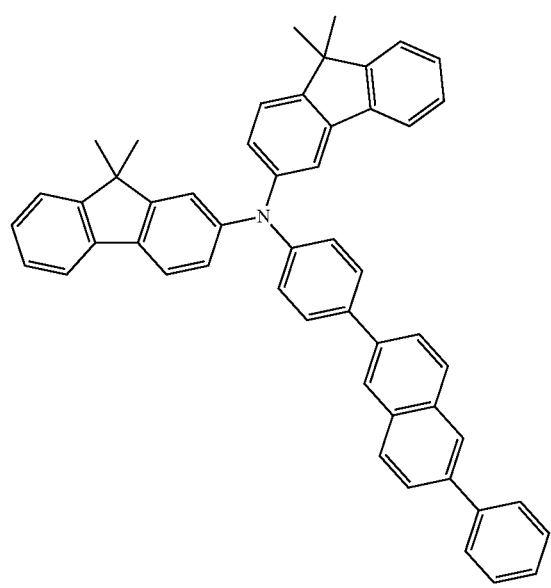
32
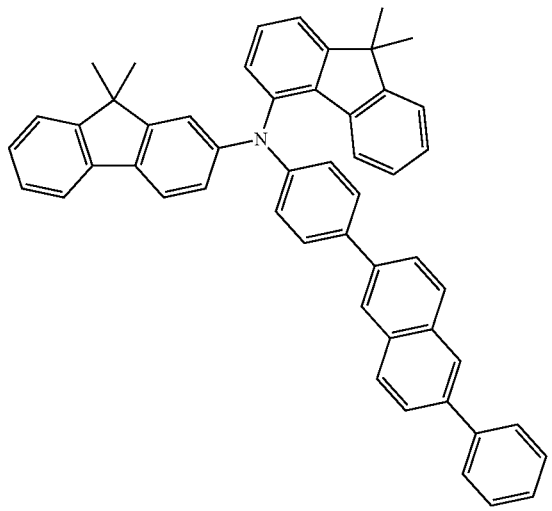
33
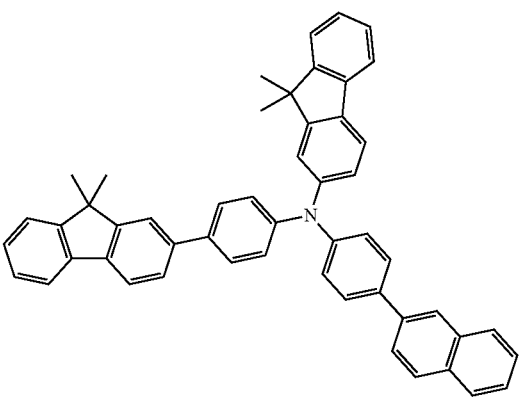

35
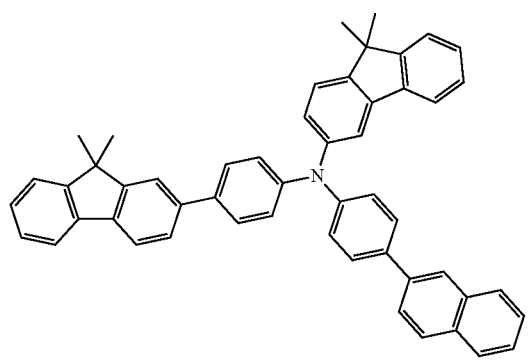
36
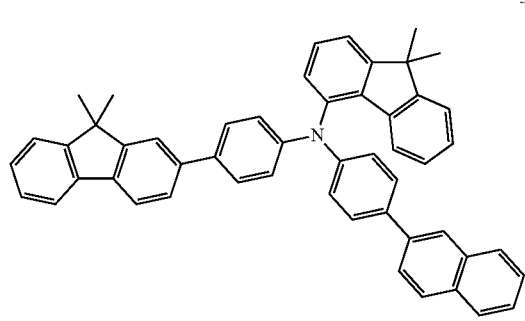
37
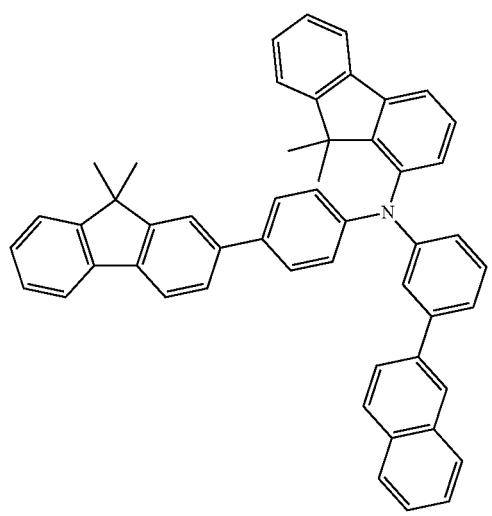
38
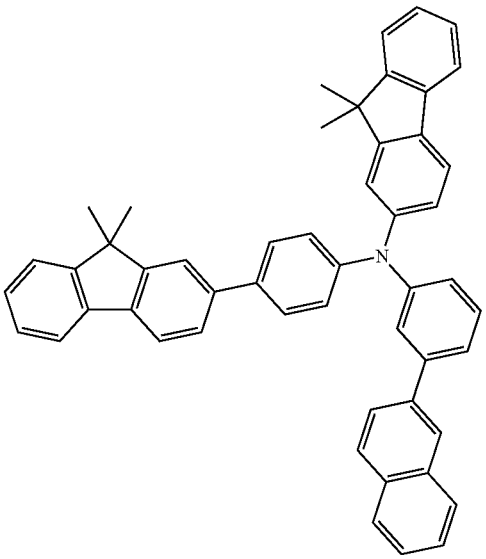
39
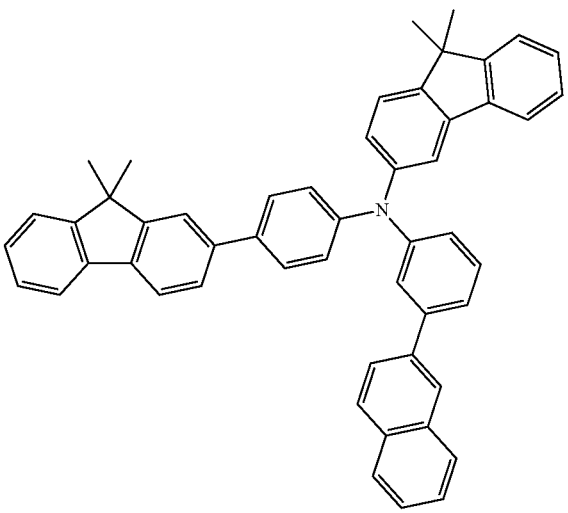
40
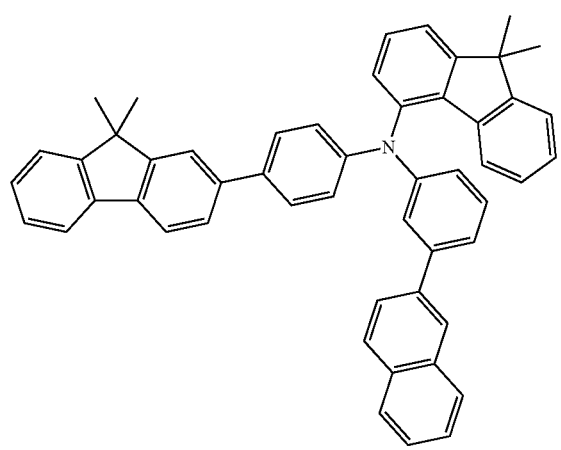

41
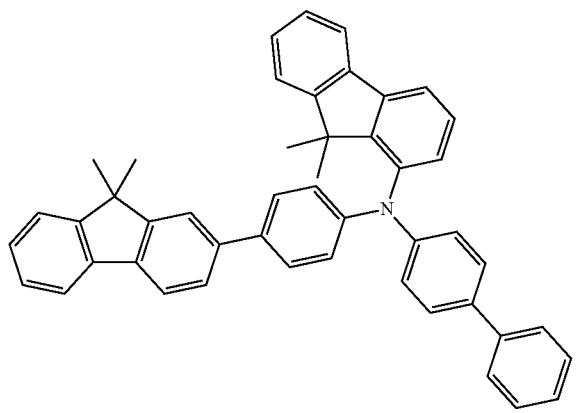
42
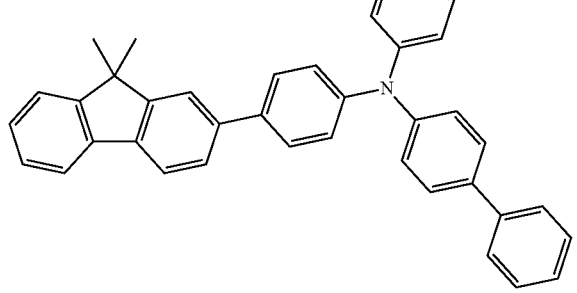
43
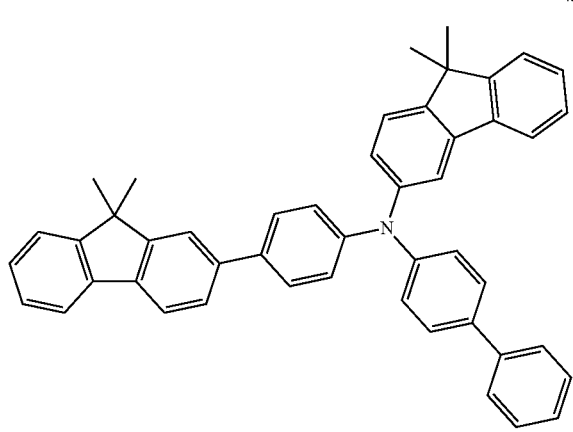
44
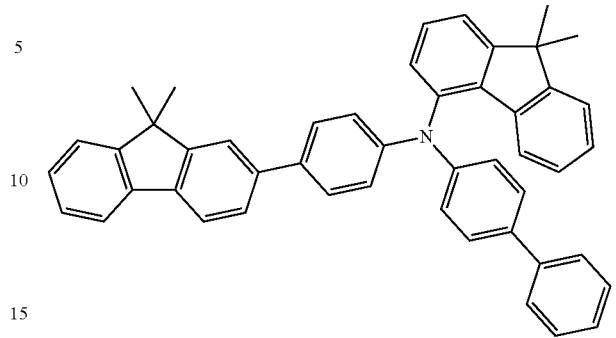
45
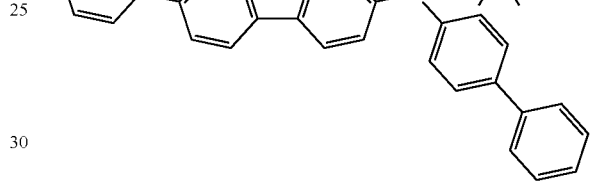
46
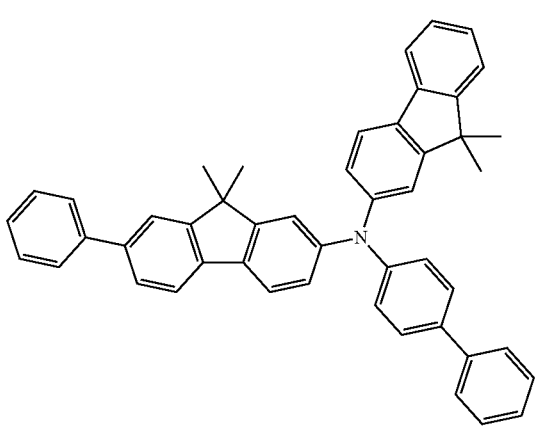
47
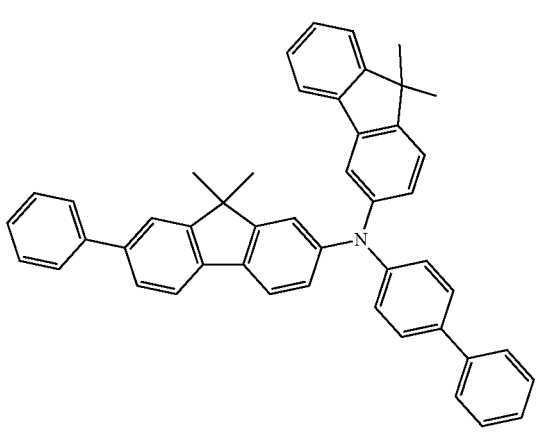

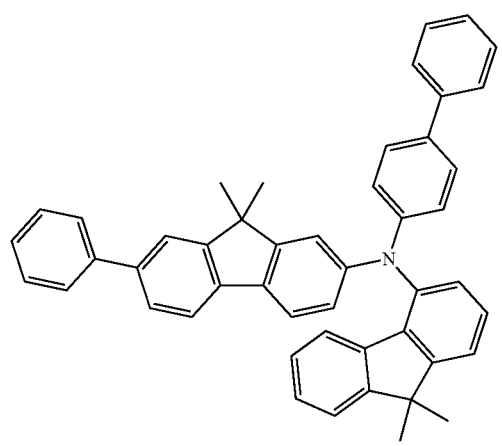
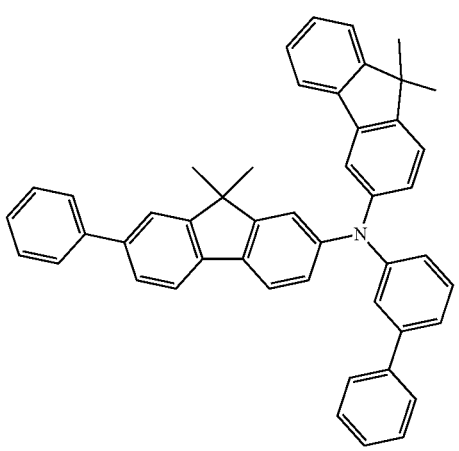
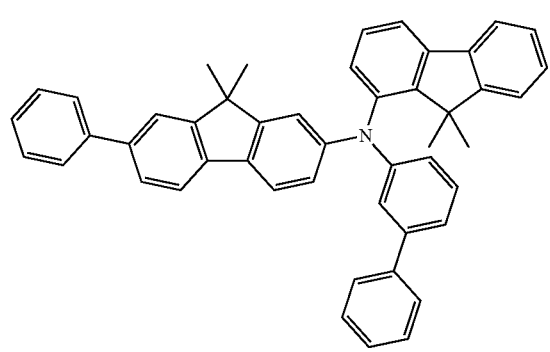
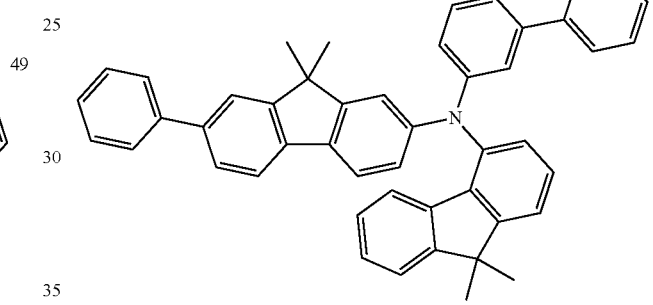
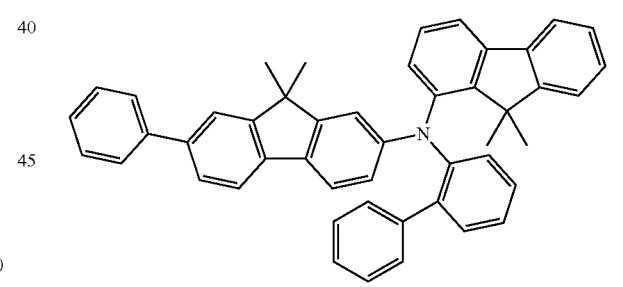
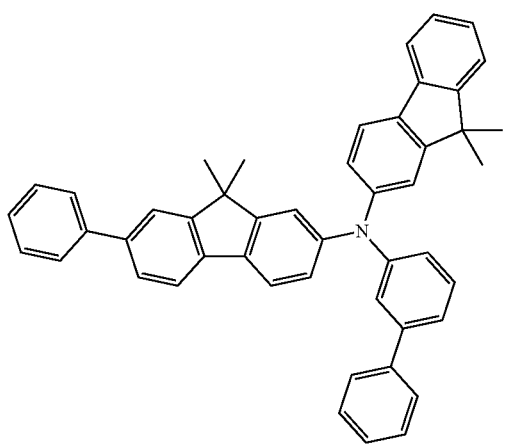
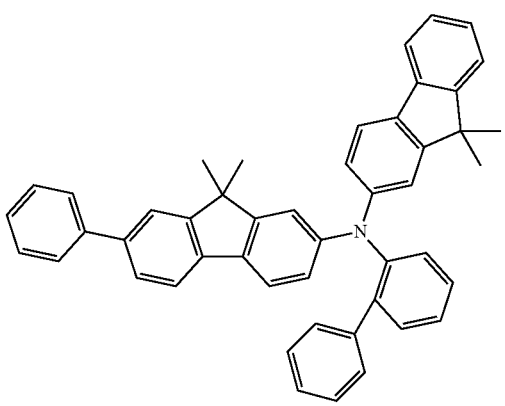

55
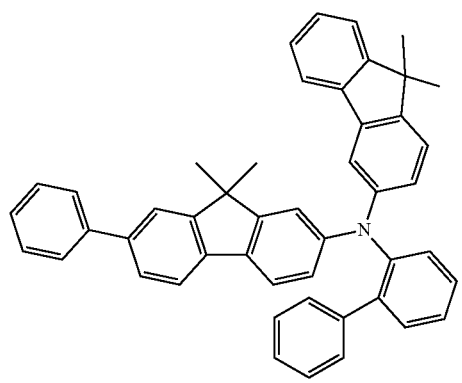
56
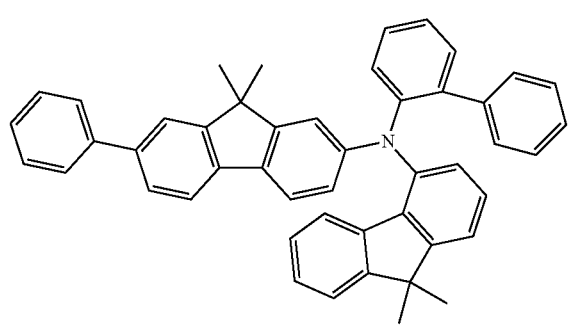
57
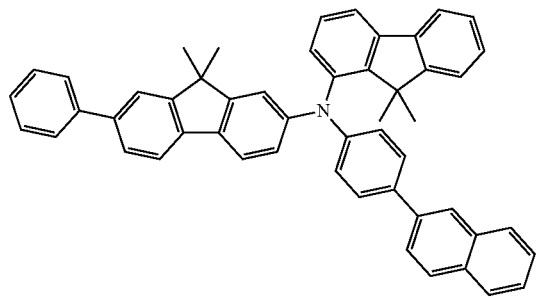
58
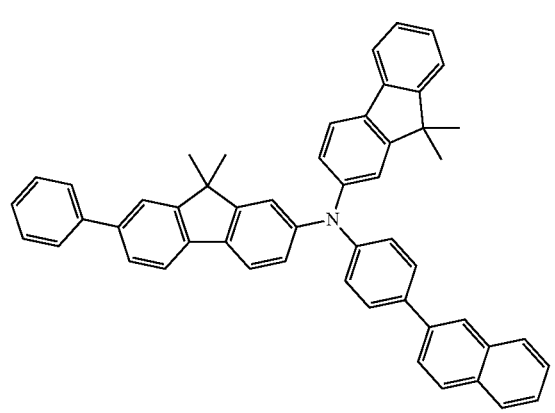
59
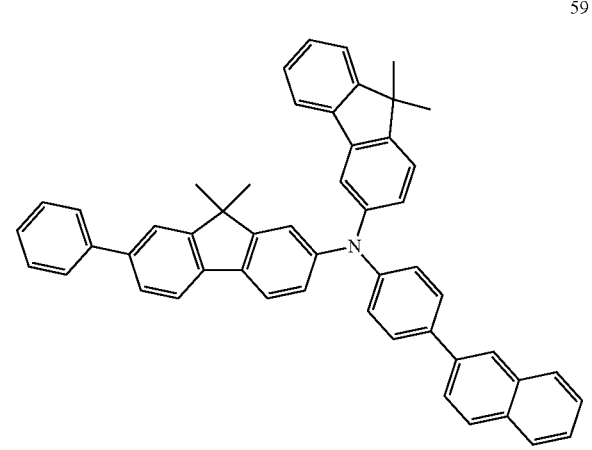
60
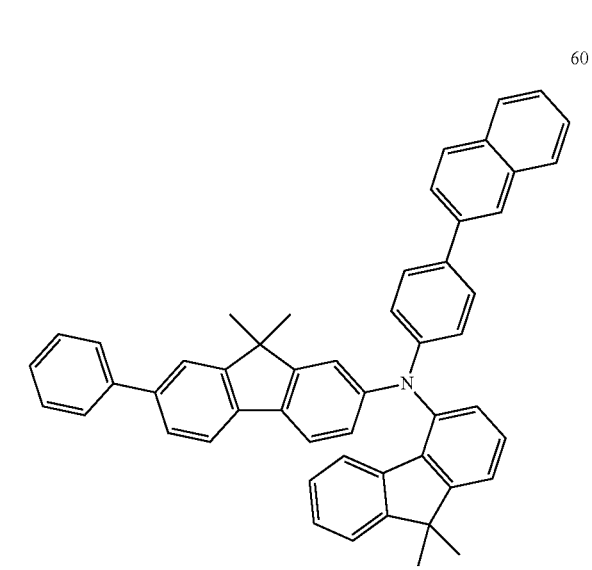
61
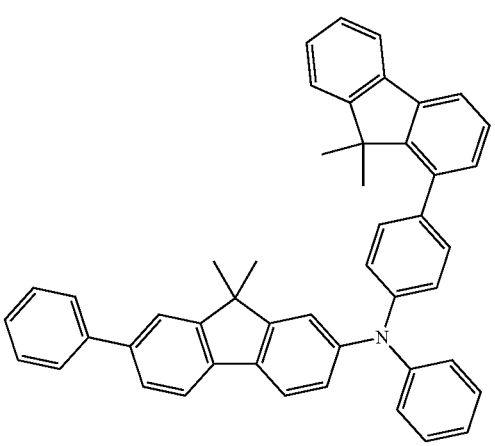

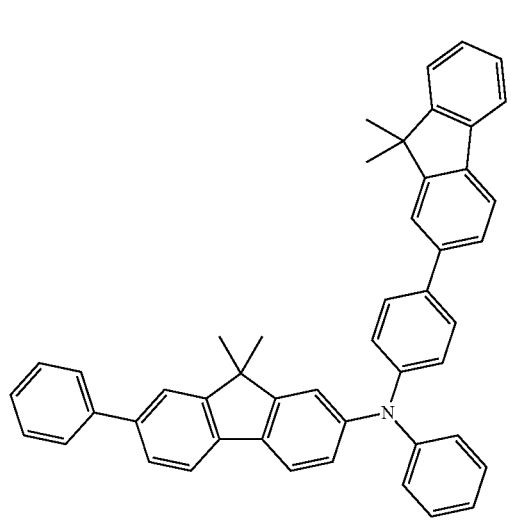
62
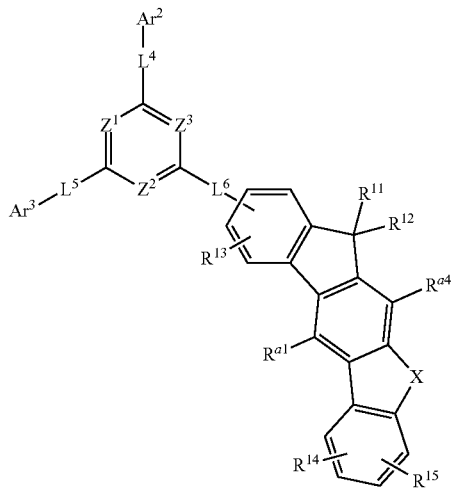
[Chemical Formula 2A]
63
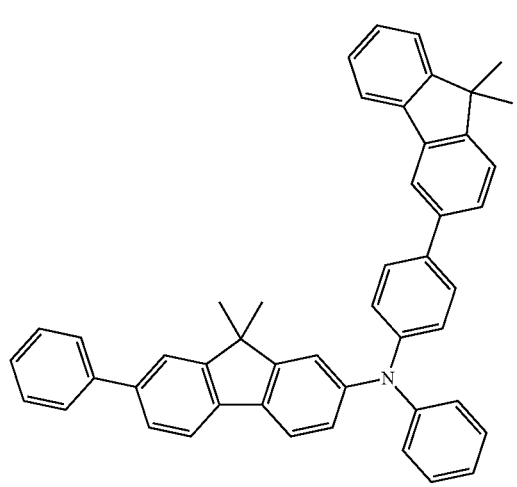
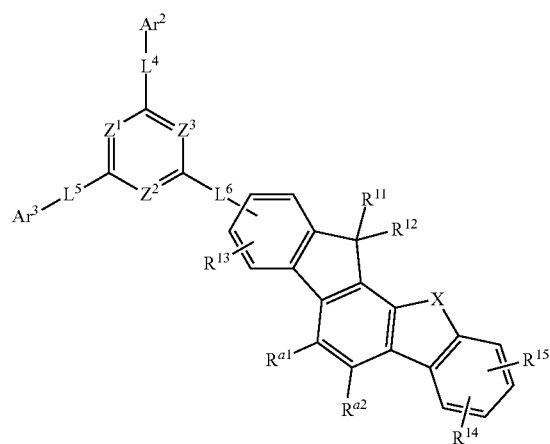
[Chemical Formula 2B]
64
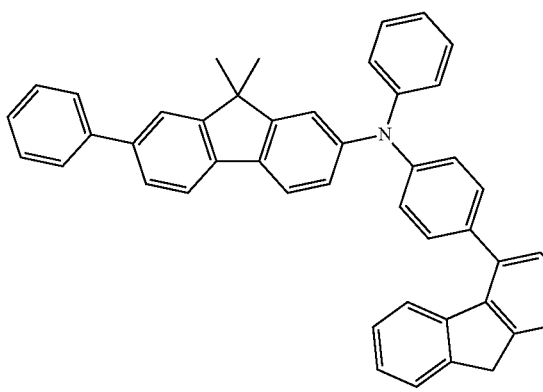
In an implementation, the second compound may be represented by one of Chemical Formula 2A to Chemical Formula 2F, depending on the fusion direction of fused fluorenyl.
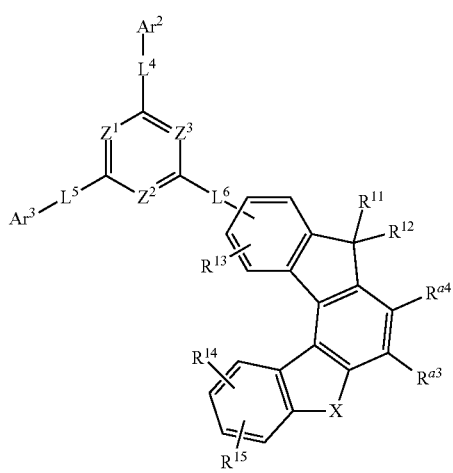
[Chemical Formula 2C]

[Chemical Formula 2D]

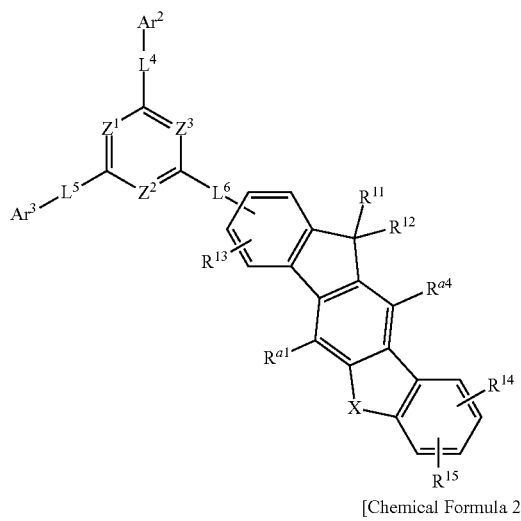

[Chemical Formula 2E]

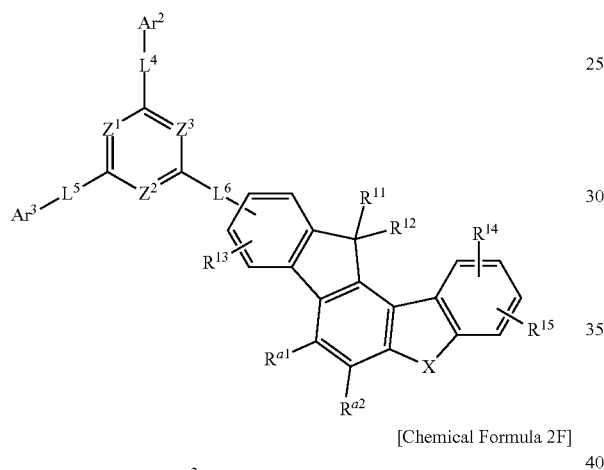

[Chemical Formula 2F]

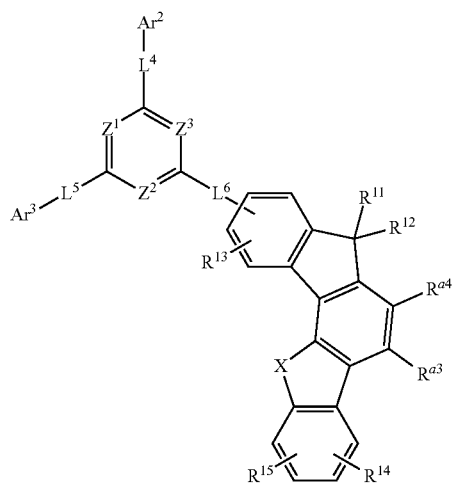

In Chemical Formula 2A to Chemical Formula 2F, $Z^1$ to $Z^3$, X, $Ar^2$, $Ar^3$, $L^4$ to $L^6$, and $R^{11}$ to $R^{15}$ may be defined the same as described above, and $R^{a1}$ to $R^{a4}$ may be defined the same as $R^a$.

In an implementation, Chemical Formula 2A may be represented by Chemical Formula 2A-2 or Chemical Formula 2A-4.

[Chemical Formula 2A-2]

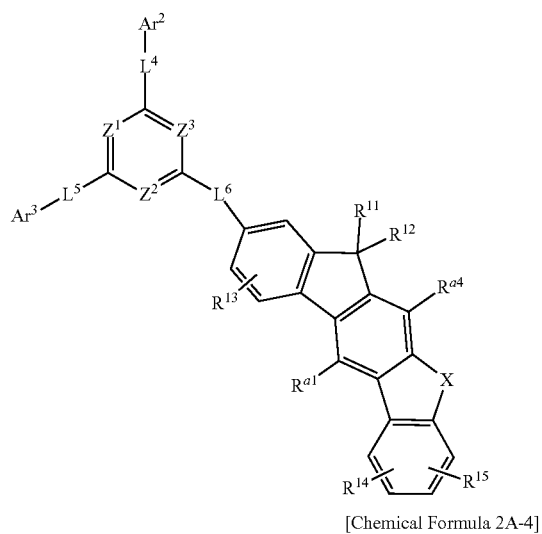

[Chemical Formula 2A-4]

In an implementation, Chemical Formula 2B may be represented by Chemical Formula 2C-2 or Chemical Formula 2B-4.

[Chemical Formula 2B-2]

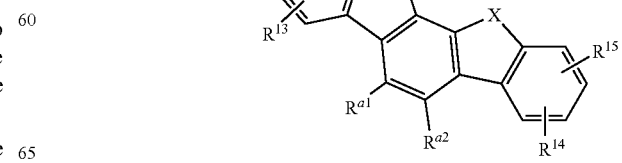

-continued

[Chemical Formula 2B-4]

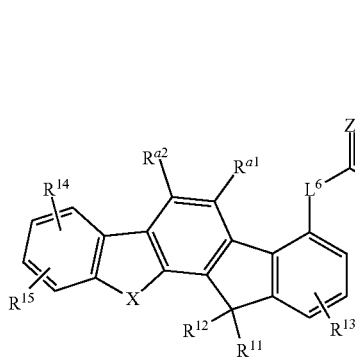

In an implementation, Chemical Formula 2C may be represented by Chemical Formula 2C-2 or Chemical Formula 2C-4.

[Chemical Formula 2C-2]

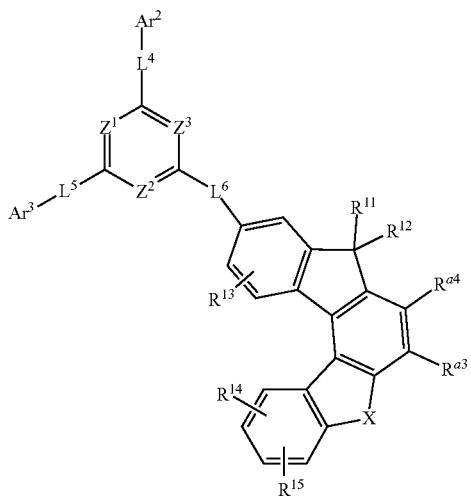

[Chemical Formula 2C-4]

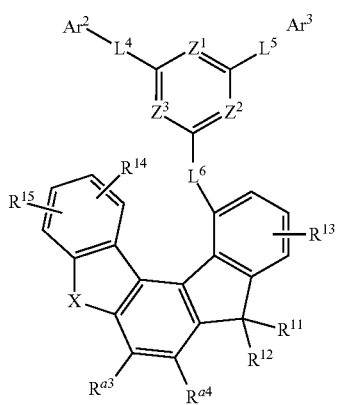

In an implementation, Chemical Formula 2D may be represented by Chemical Formula 2D-2 or Chemical Formula 2D-4.

[Chemical Formula 2D-2]

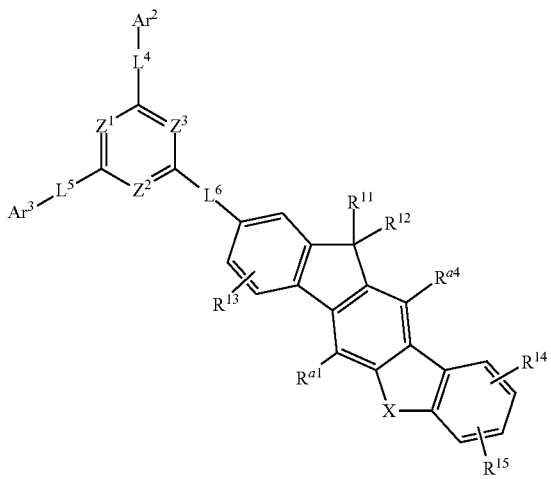

[Chemical Formula 2D-4]

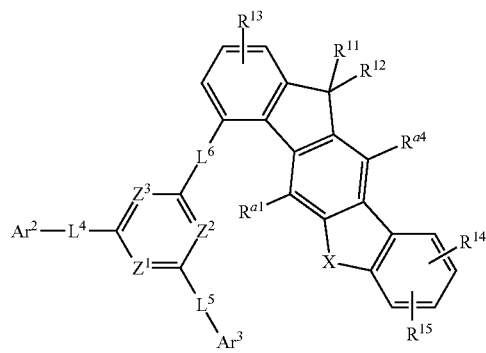

In an implementation, Chemical Formula 2E may be represented by Chemical Formula 2E-2 or Chemical Formula 2E-4.

[Chemical Formula 2E-2]

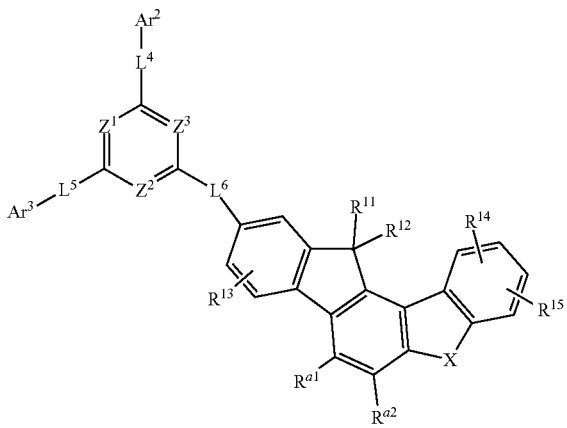

[Chemical Formula 2E-4]

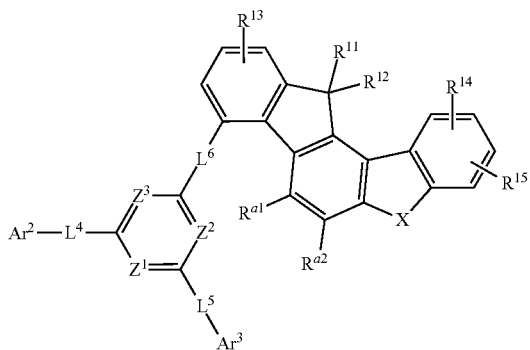

In an implementation, Chemical Formula 2F may be represented by Chemical Formula 2F-2 or Chemical Formula 2F-4.

[Chemical Formula 2F-2]

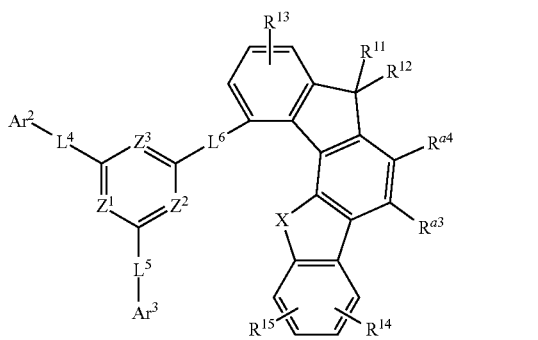

[Chemical Formula 2F-4]

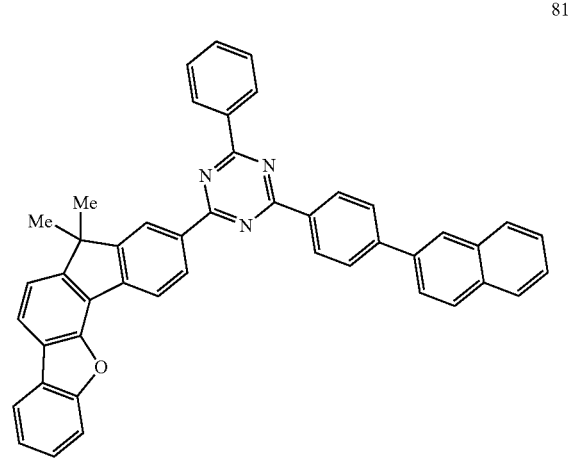

In Chemical Formula 2A-2, Chemical Formula 2A-4, Chemical Formula 2B-2, Chemical Formula 2B-4, Chemical Formula 2C-2, Chemical Formula 2C-4, Chemical Formula 2D-2, Chemical Formula 2D-4, Chemical Formula 2E-2, Chemical Formula 2E-4, Chemical Formula 2F-2, and Chemical Formula 2F-4, $Z^1$ to $Z^3$, X, $Ar^2$, $Ar^3$, $L^4$ to $L^6$, $R^{11}$ to $R^{15}$, and $R^{a1}$ to $R^{a4}$ may be defined the same as described above.

In an implementation, the second compound may be represented by Chemical Formula 2A or Chemical Formula 2F.

In an implementation, the second compound may be represented by Chemical Formula 2A-2, Chemical Formula 2A-4, Chemical Formula 2F-2, or Chemical Formula 2F-4.

In an implementation, the second compound may be represented by Chemical Formula 2A-2, Chemical Formula 2F-2, or Chemical Formula 2F-4.

In an implementation, $Ar^2$ and $Ar^3$ of Chemical Formula 2 may each independently be, e.g., a substituted or unsubstituted phenyl group, a substituted or unsubstituted biphenyl group, a substituted or unsubstituted naphthyl group, a substituted or unsubstituted triphenylene group, a substituted or unsubstituted fluorenyl group, a substituted or unsubstituted benzofluorenyl group, a substituted or unsubstituted dibenzofuranyl group, or a substituted or unsubstituted dibenzothiophenyl group.

In an implementation, $Ar^2$ and $Ar^3$ of Chemical Formula 2 may each independently be, e.g., a substituted or unsubstituted phenyl group, a substituted or unsubstituted naphthyl group, or a substituted or unsubstituted fluorenyl group.

In an implementation, $R^{11}$ and $R^{12}$ of Chemical Formula 2 may each independently be, e.g., a substituted or unsubstituted methyl group or a substituted or unsubstituted phenyl group.

In an implementation, $R^{11}$ and $R^{12}$ of Chemical Formula 2 may each be a substituted or unsubstituted methyl group.

In an implementation, $L^4$ to $L^6$ in Chemical Formula 2 may each independently be, e.g., a single bond or a substituted or unsubstituted phenylene group.

In an implementation, $L^4$ and $L^5$ of Chemical Formula 2 may each independently be, e.g., a single bond or a substituted or unsubstituted phenylene group, and $L^6$ may be, e.g., a single bond.

In an implementation, $R^{13}$ to $R^{15}$ of Chemical Formulae 2 and 3 may each be hydrogen.

In an implementation, the second compound may be a compound of the following Group 2.

[Group 2]

81

82
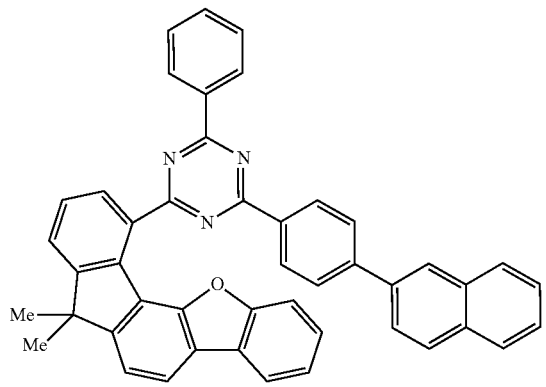
83
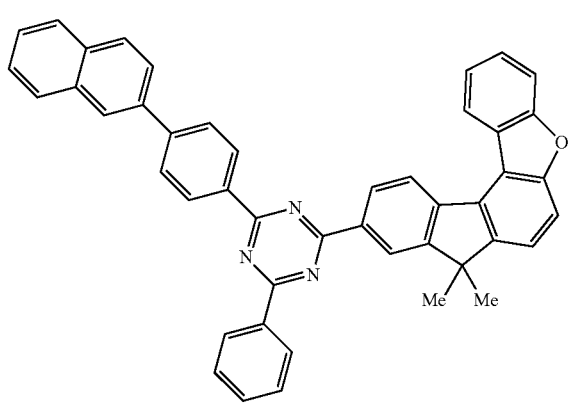
84
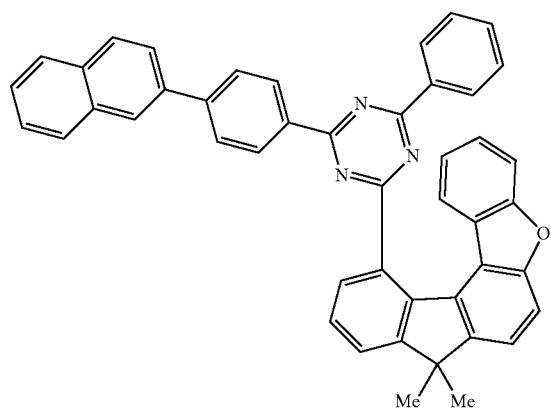
85
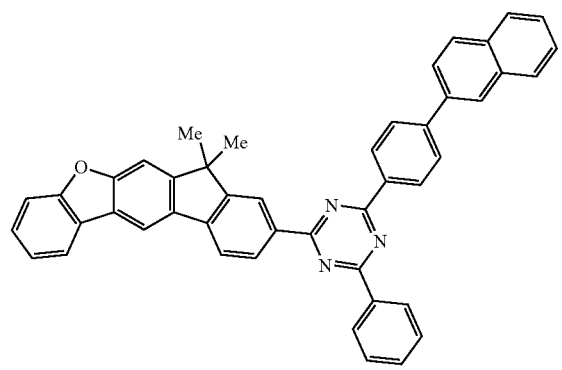
86
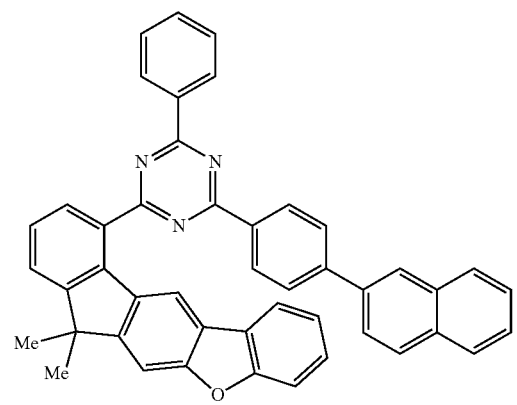
87
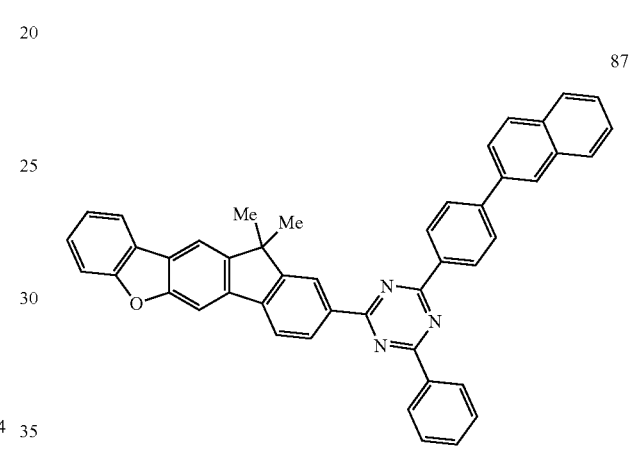
88
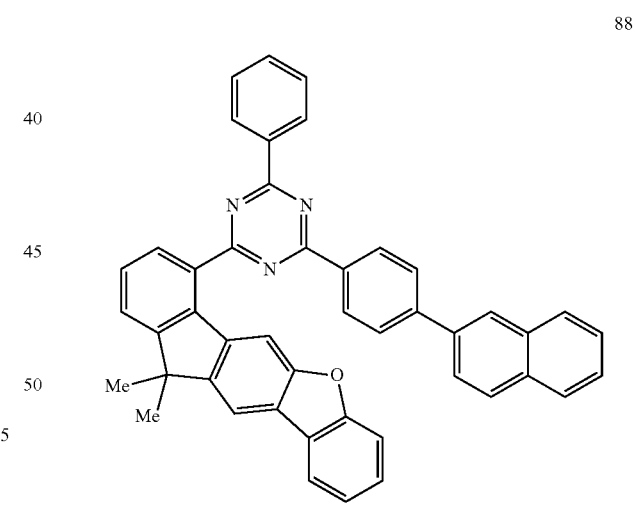
89
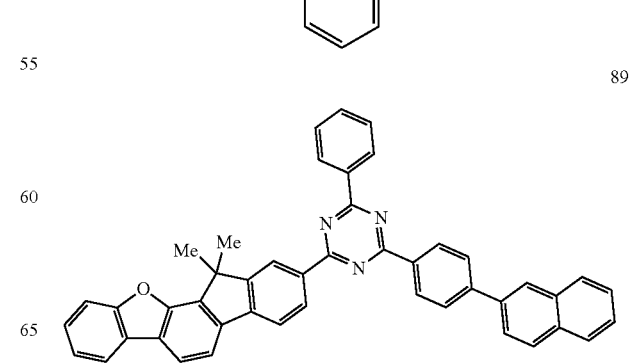

90
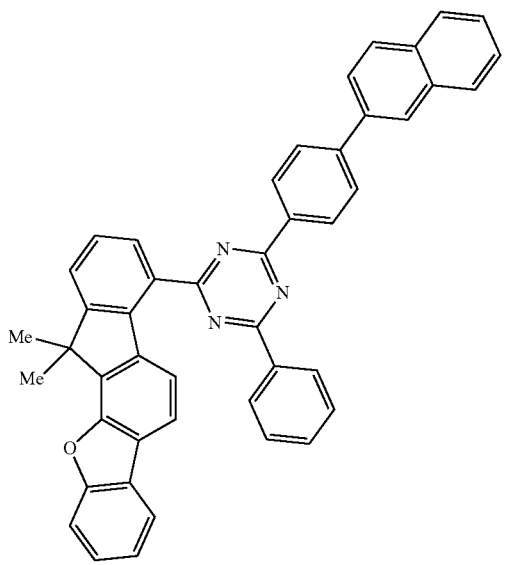
91
93
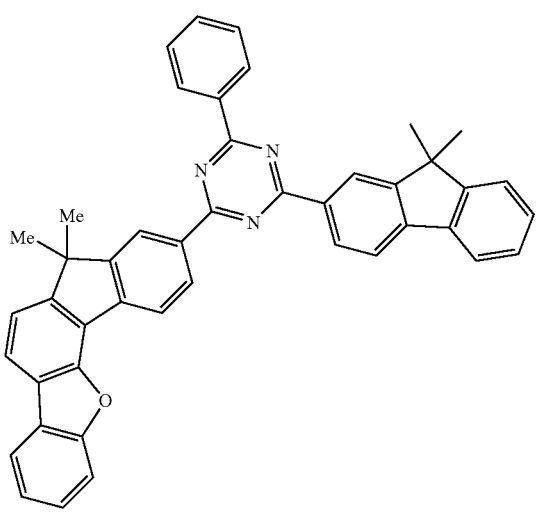
94
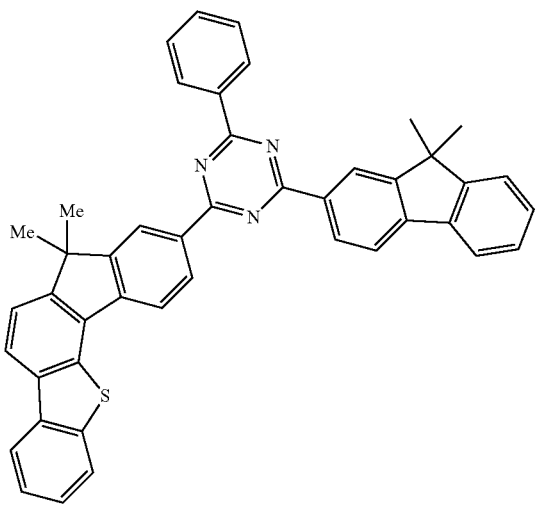
92
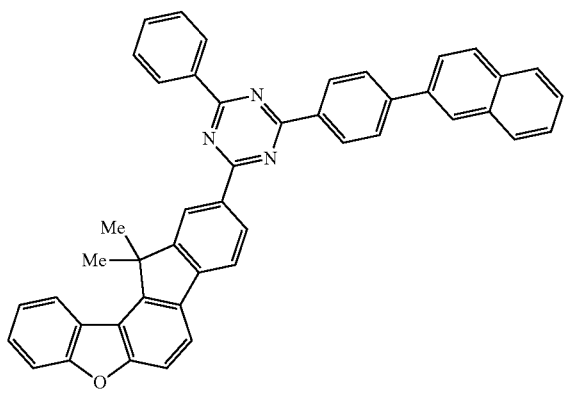
95
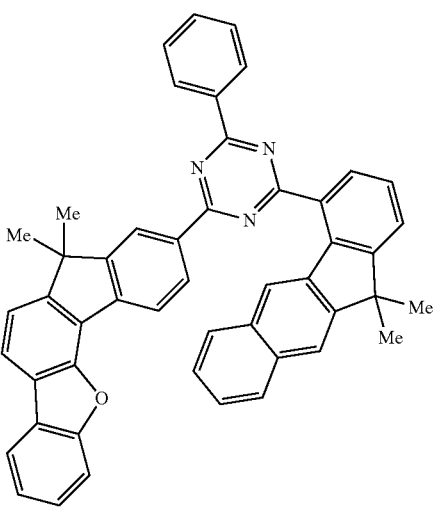

96

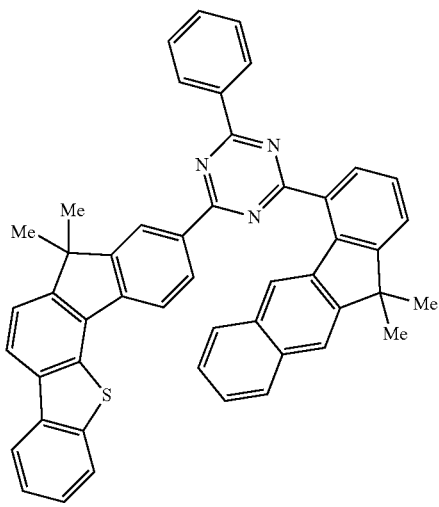

98

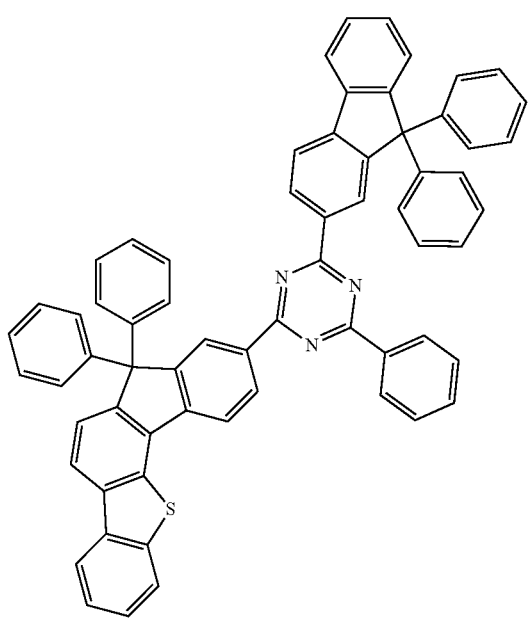

In an implementation, the composition for an organic optoelectronic device may include a first compound represented by Chemical Formula 1-3a and a second compound represented by one of Chemical Formula 2A-2, Chemical Formula 2F-2 and Chemical Formula 2F-4.

[Chemical Formula 1-3a]

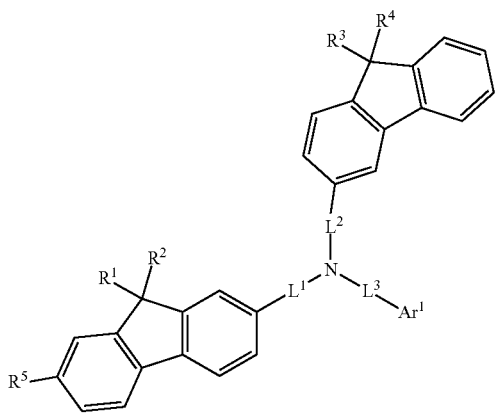

97

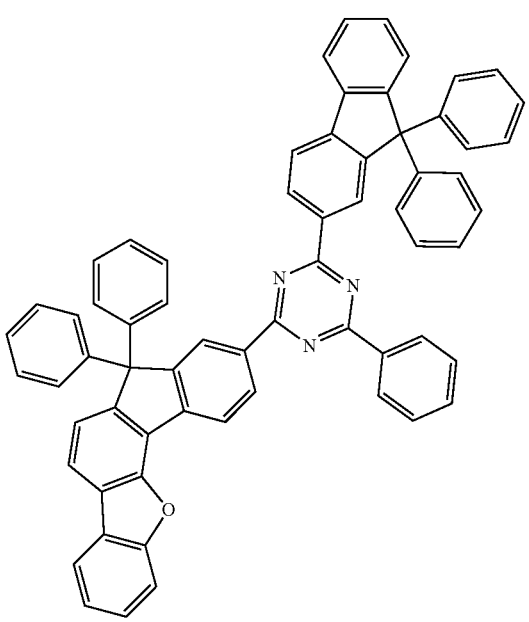

In Chemical Formula 1-3a, $R^1$ to $R^4$ may each independently be, e.g., a substituted or unsubstituted methyl group or a substituted or unsubstituted phenyl group, $R^5$ may be, e.g., hydrogen or a substituted or unsubstituted phenyl group, and $L^1$ to $L^3$ may each independently be, e.g., a single bond or a substituted or unsubstituted phenylene group.

In Chemical Formula 2A-2, Chemical Formula 2F-2, and Chemical Formula 2F-4, X may be, e.g., O, S, or $CR^cCR^d$, $Ar^2$ and $Ar^3$ may each independently be, e.g., a substituted or unsubstituted phenyl group, a substituted or unsubstituted naphthyl group, or a substituted or unsubstituted fluorenyl group, $R^c$, $R^d$, $R^{11}$, and $R^{12}$ may each independently be, e.g., a substituted or unsubstituted methyl group or a substituted or unsubstituted phenyl group, $L^4$ to $L^6$ may each independently be, e.g., a single bond or a substituted or unsubstituted phenylene group, and $R^{a3}$, $R^{a4}$, and $R^{13}$ to $R^{15}$ may each be, e.g., hydrogen.

The first compound for an organic optoelectronic device and the second compound for an organic optoelectronic device may be, e.g., included (e.g., mixed) in a weight ratio of about 1:99 to about 99:1. Within the above range, bipolar characteristics may be by implemented by adjusting an appropriate weight ratio using a hole transport capability of the first compound for an organic optoelectronic device and an electron transport capability of the second compound for an organic optoelectronic device, and thus efficiency and life-span may be improved. Within the above range, e.g., they may be included in a weight ratio of about 90:10 to about 10:90, about 90:10 to about 20:80, about 90:10 to about 30:70, or about 90:10 to about 40:60. In an implementation, they may be included in a weight ratio of about 80:20 to about 40:60, e.g., about 50:50.

In an implementation, the first compound and the second compound may be included as a host, e.g., a phosphorescent host of a light emitting layer.

In addition to the aforementioned host, the light emitting layer may further include one or more compounds.

The light emitting layer may further include a dopant. The dopant may be, e.g., a phosphorescent dopant, such as a red, green, or blue phosphorescent dopant. In an implementation, the dopant may be, e.g., a red phosphorescent dopant.

The dopant may be a material mixed with the composition for an organic optoelectronic device in a small amount to facilitate light emission and may be generally a material such as a metal complex that emits light by multiple excitation into a triplet or more. The dopant may be, e.g. an inorganic, organic, or organic-inorganic compound, and one or more types thereof may be used.

Examples of the dopant may include a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^4MX$            [Chemical Formula Z]

In Chemical Formula Z, M may be a metal, and $L^4$ and X may each independently be a ligand to form a complex compound with M.

The M may be, e.g., Ir, Pt, Os, Ti, Zr, Hf, Eu, Tb, Tm, Fe, Co, Ni, Ru, Rh, Pd, or a combination thereof, and the $L^4$ and X may be, e.g., a bidendate ligand.

The aforementioned composition for an organic optoelectronic device may be formed by a dry film formation method such as chemical vapor deposition (CVD).

Hereinafter, an organic optoelectronic device including the aforementioned composition for an organic optoelectronic device is described.

The organic optoelectronic device may be a suitable device to convert electrical energy into photoenergy and vice versa, e.g., an organic photoelectric device, an organic light emitting diode, an organic solar cell, and an organic photoconductor drum.

Herein, an organic light emitting diode as one example of an organic optoelectronic device is described referring to drawings.

FIGS. 1 and 2 are cross-sectional views showing organic light emitting diodes according to embodiments.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to facilitate hole injection, and may be, e.g., a metal, a metal oxide, or a conductive polymer. The anode 120 may be, e.g., a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to facilitate electron injection, and may be, e.g., a metal, a metal oxide, or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; a multi-layer structure material such as LiF/Al, $LiO_2$/Al, LiF/Ca, or $BaF_2$/Ca.

The organic layer 105 may include the aforementioned composition for an organic optoelectronic device.

The organic layer 105 may include a light emitting layer 130 and the light emitting layer 130 may include the aforementioned composition for an organic optoelectronic device.

The light emitting layer 130 may include, e.g., the aforementioned composition for an organic optoelectronic device as a phosphorescent host.

In addition to the aforementioned host, the light emitting layer may further include one or more compounds.

The light emitting layer may further include a dopant. The dopant may be, e.g., a phosphorescent dopant, such as a red, green, or blue phosphorescent dopant. In an implementation, the dopant may be, e.g., a red phosphorescent dopant.

The composition for an organic optoelectronic device further including a dopant may be, e.g., a red light emitting composition.

The dopant may be a material mixed with the compound or composition for an organic optoelectronic device in a small amount to cause light emission and may be generally a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$L^7MX^2$            [Chemical Formula Z]

In Chemical Formula Z, M may be, e.g., a metal, $L^7$ and $X^2$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and $L^7$ and $X^2$ may be, e.g., a bidentate ligand.

The organic layer may further include an auxiliary layer in addition to the light emitting layer.

The auxiliary layer may be, e.g., a hole auxiliary layer 140.

Referring to FIG. 2, an organic light emitting diode 200 may further include a hole auxiliary layer 140 in addition to the light emitting layer 130. The hole auxiliary layer 140 may help further increase hole injection and/or hole mobility and blocks electrons between the anode 120 and the light emitting layer 130.

The hole auxiliary layer 140 may include, e.g., a compound of the following Group A.

In an implementation, the hole auxiliary layer 140 may include a hole transport layer between the anode 120 and the light emitting layer 130 and a hole transport auxiliary layer between the light emitting layer 130 and the hole transport layer, and a compound of Group A may be included in the hole transport auxiliary layer.

[Group A]

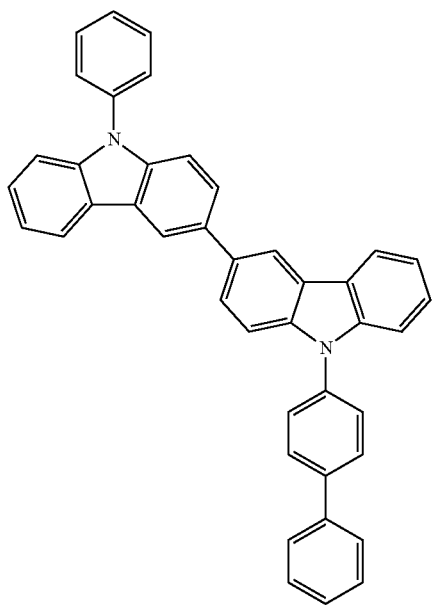

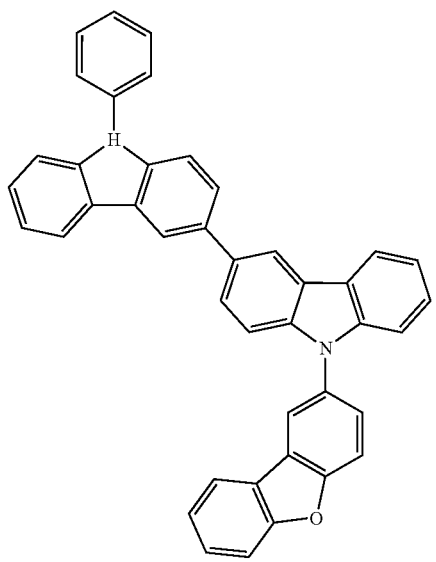

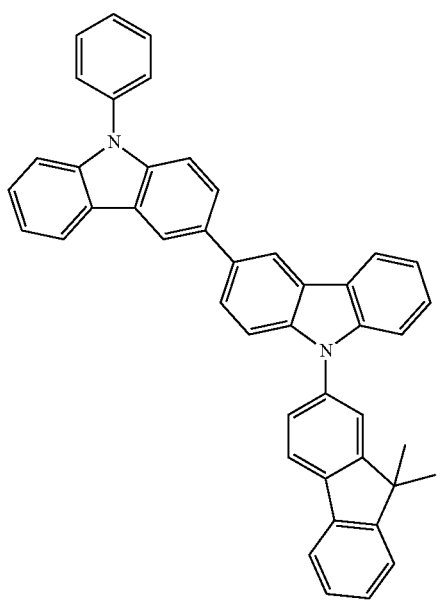

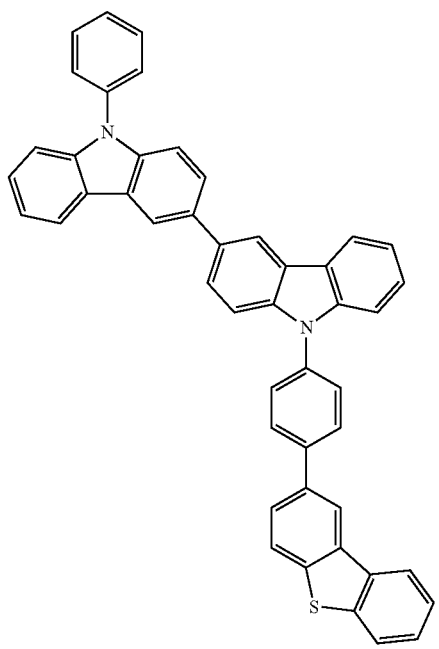

79
-continued
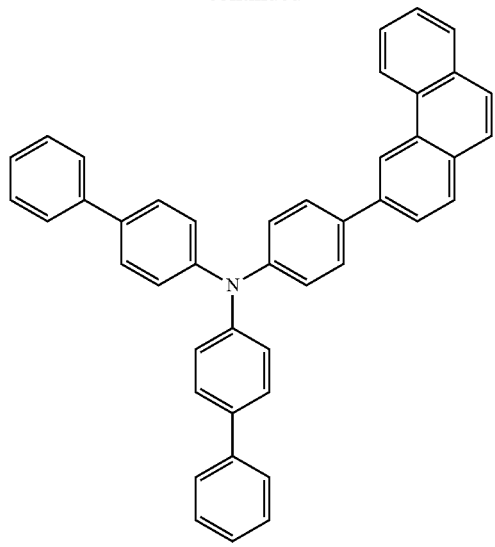
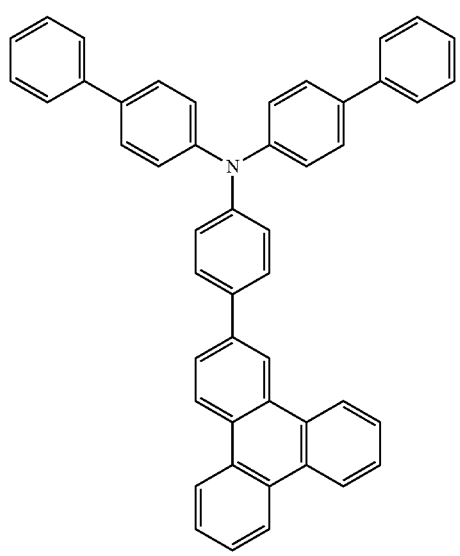
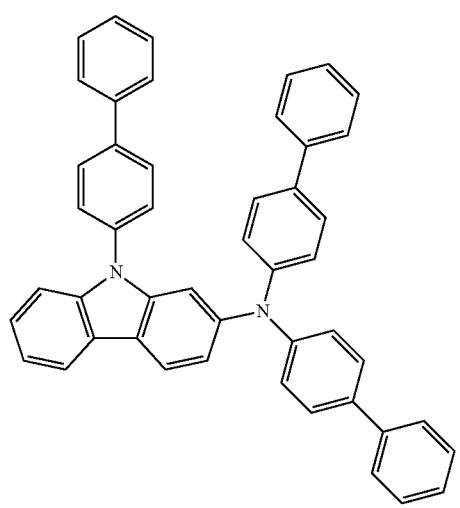
80
-continued
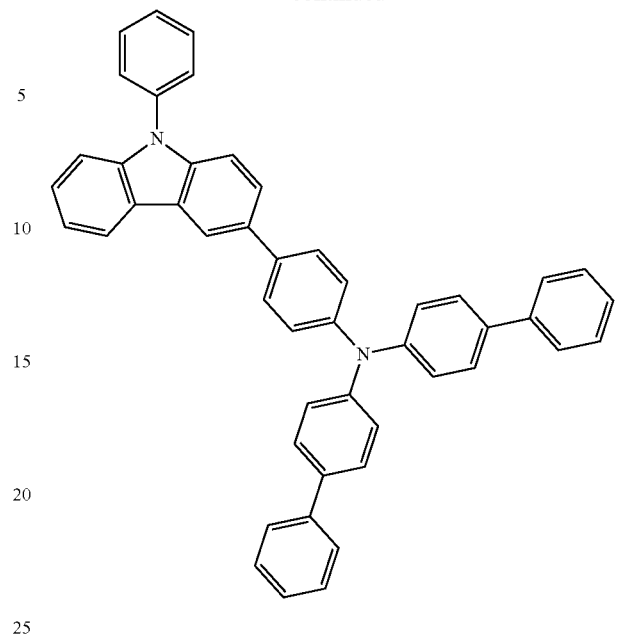
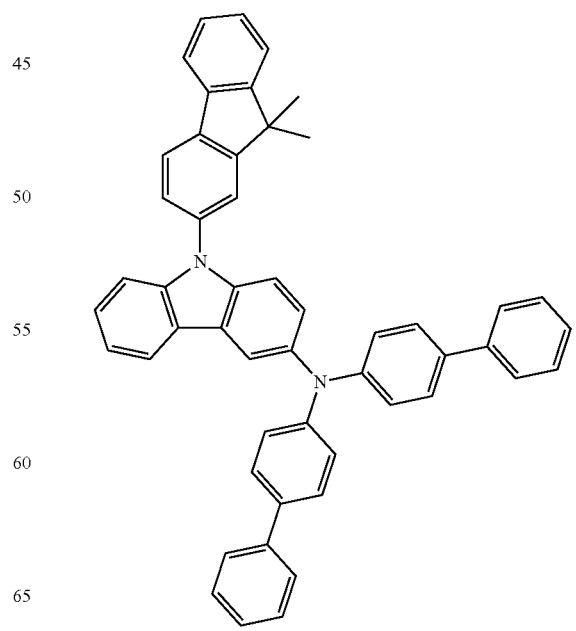

81
-continued
82
-continued
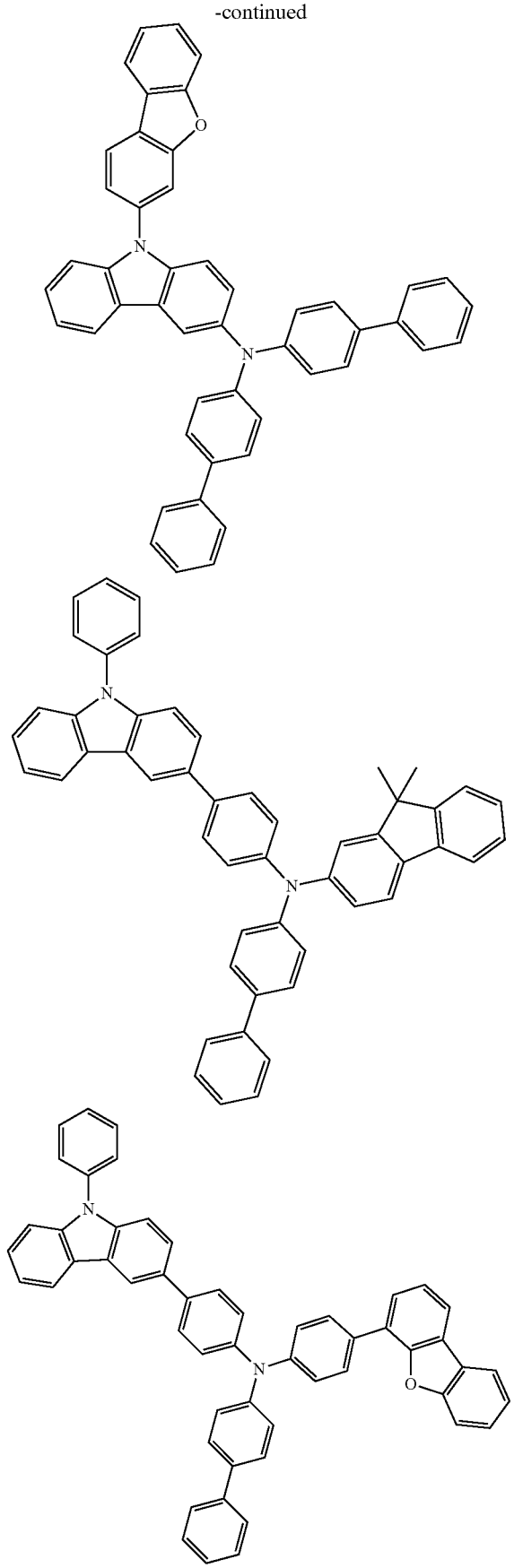
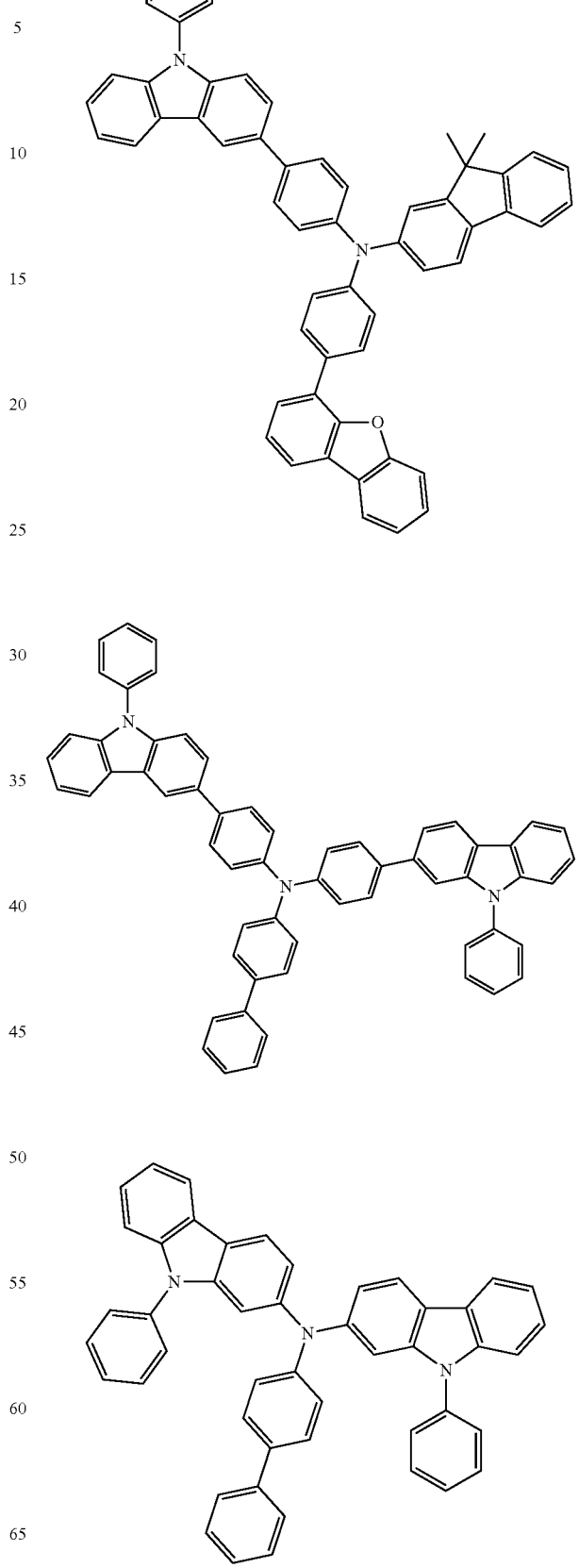

83
-continued
84
-continued
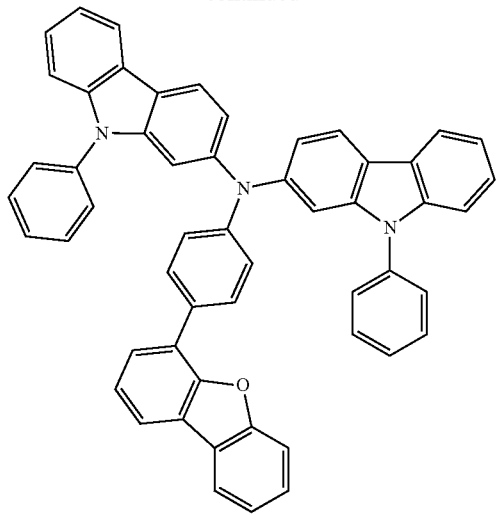
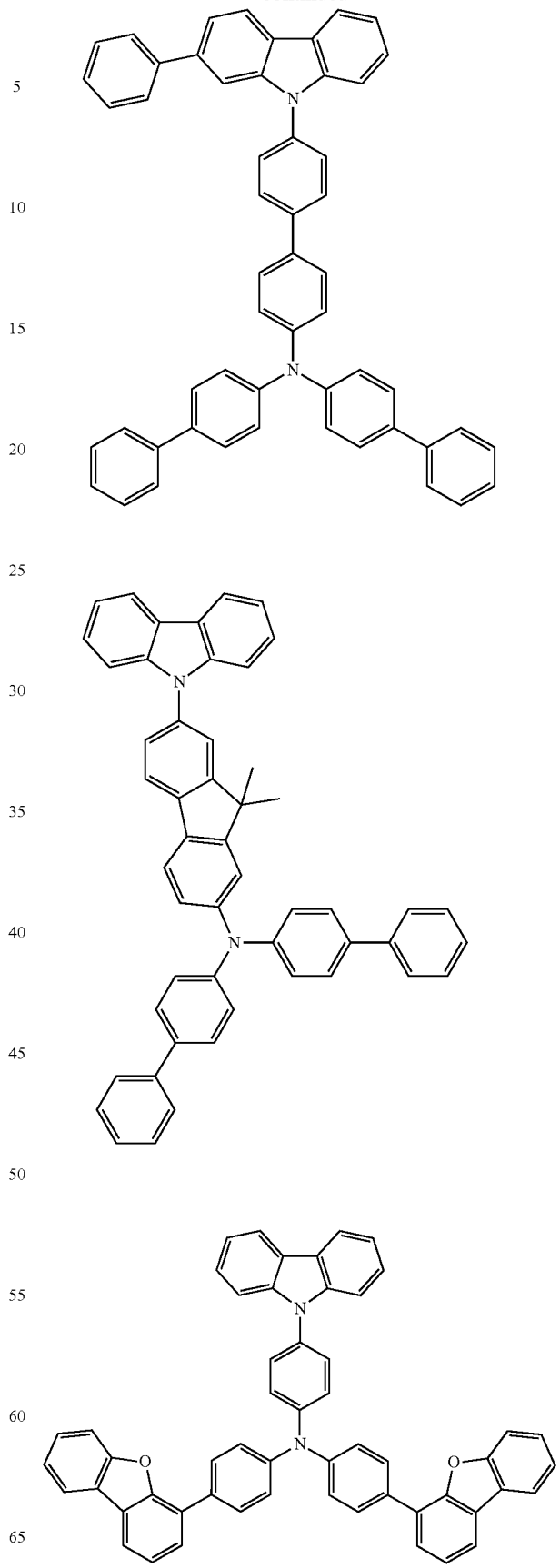

85
-continued
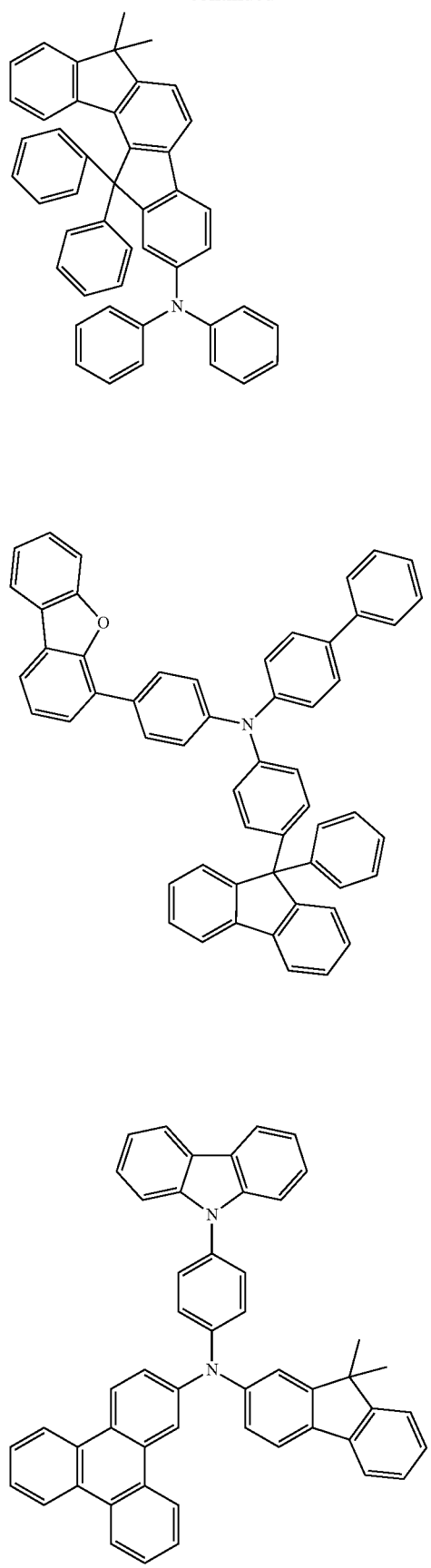
86
-continued
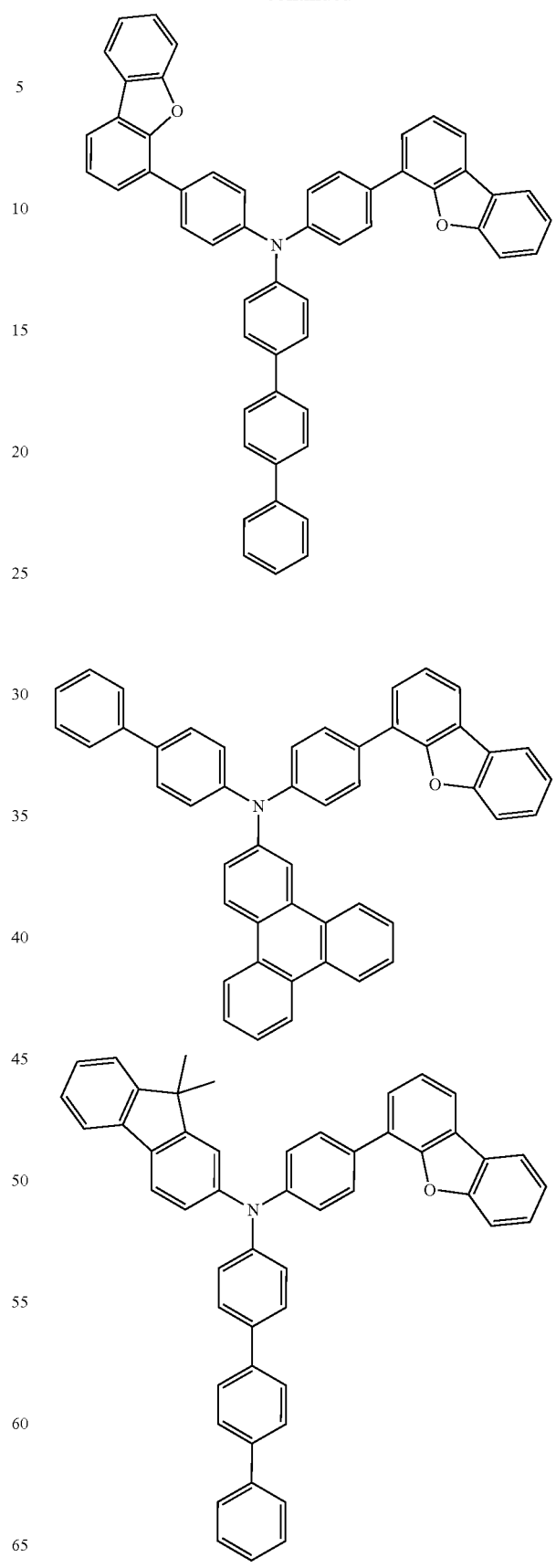

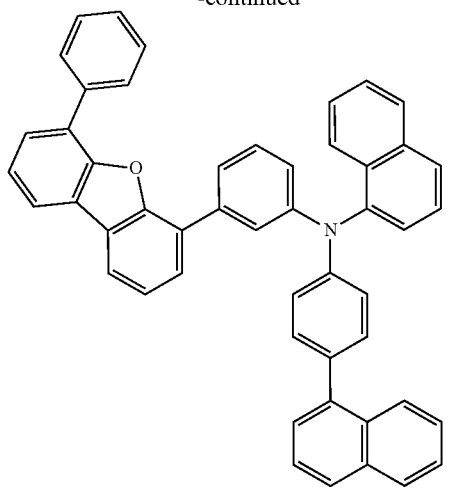
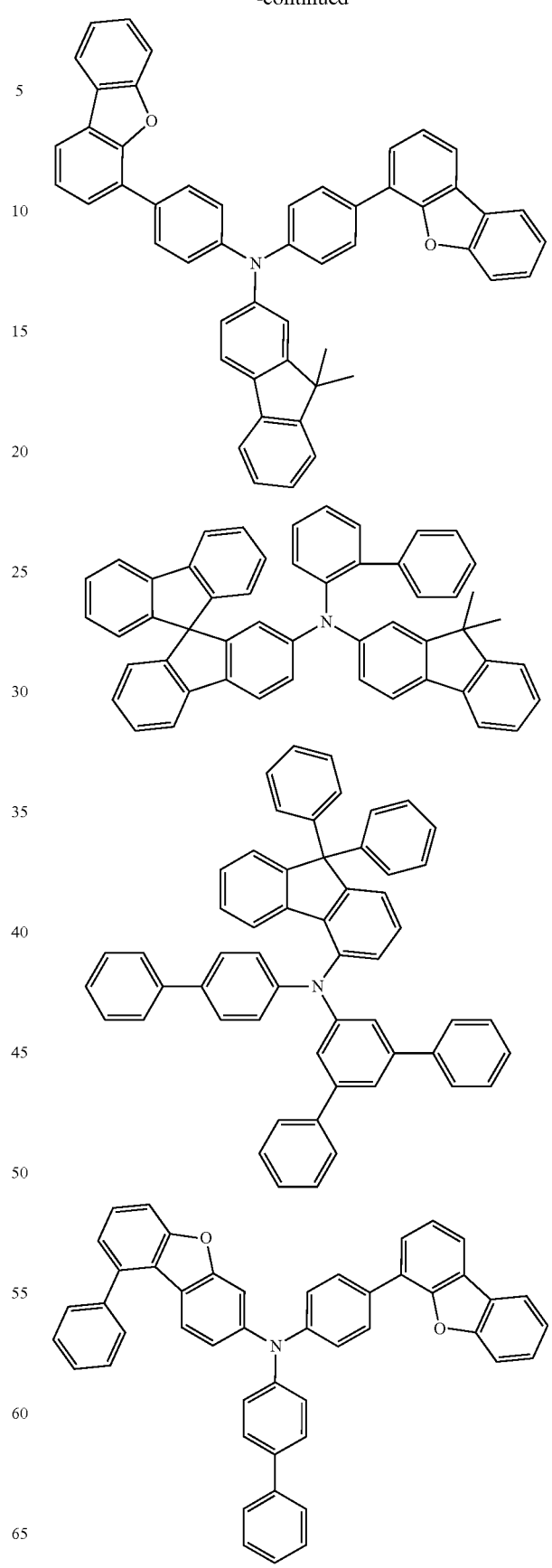

89
-continued
90
-continued
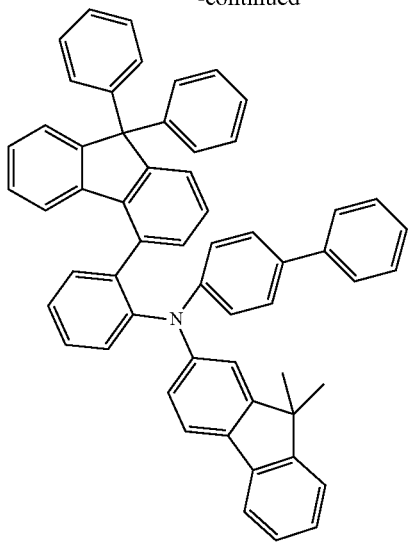
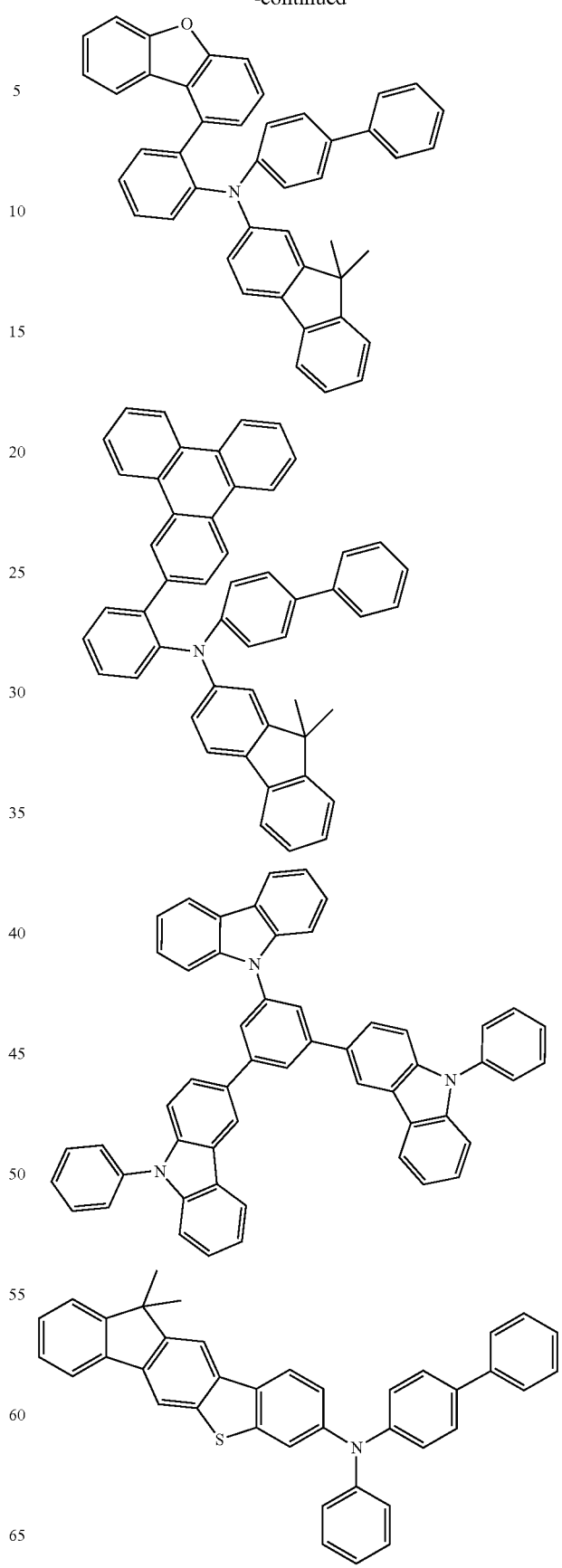

91
-continued
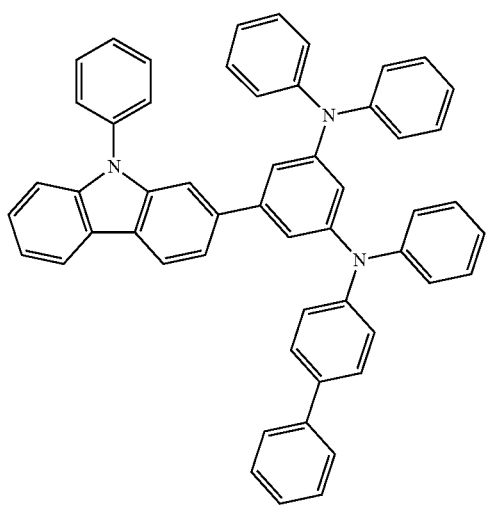
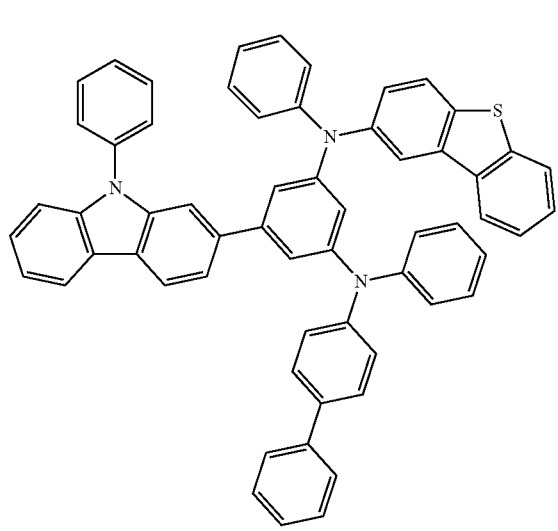
92
-continued
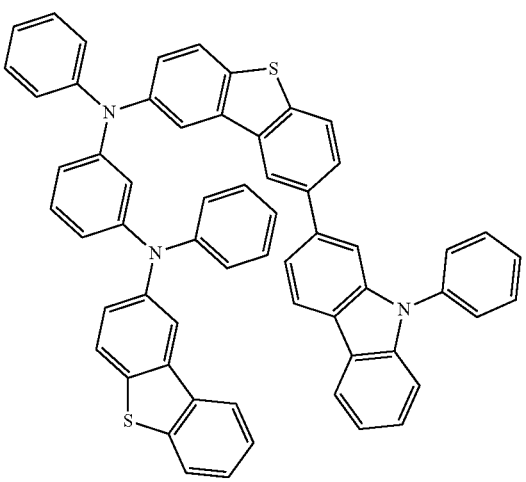
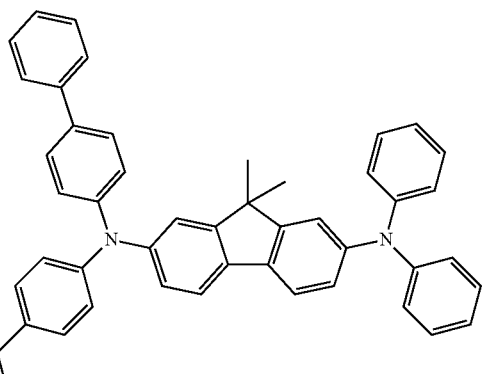

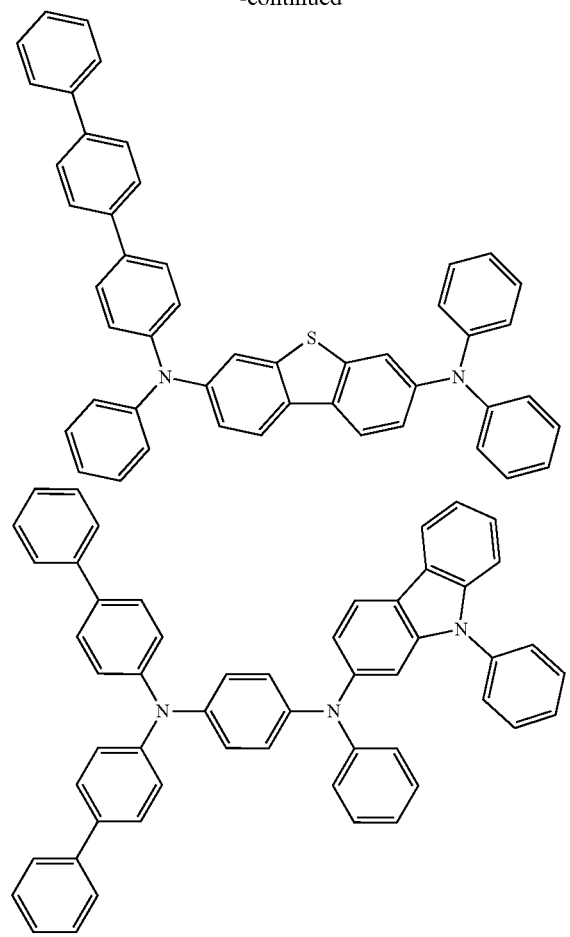
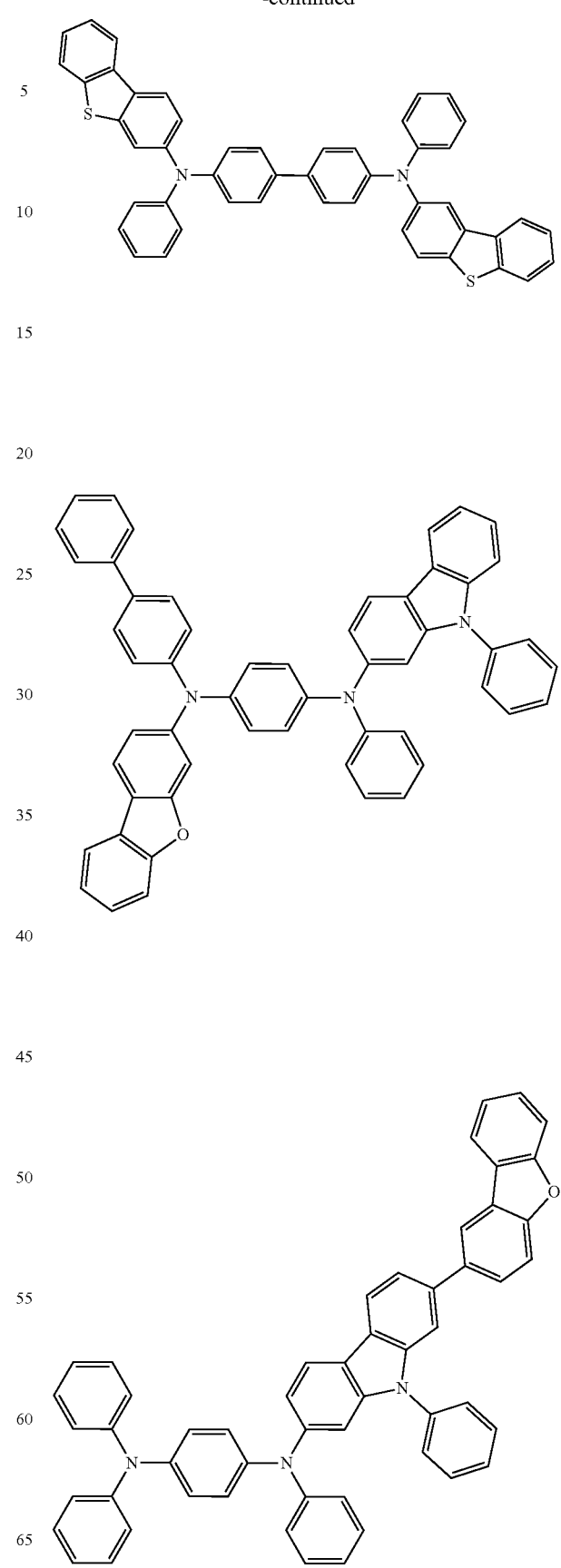

95
-continued
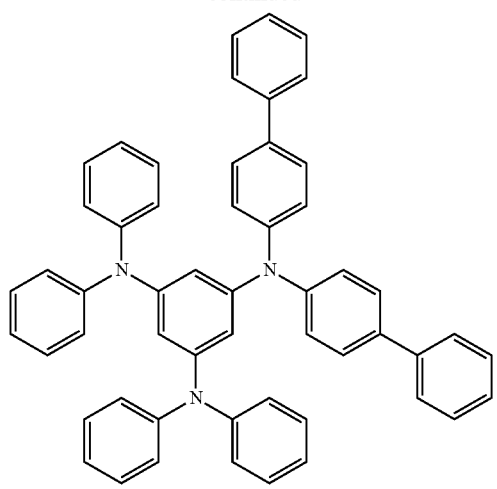
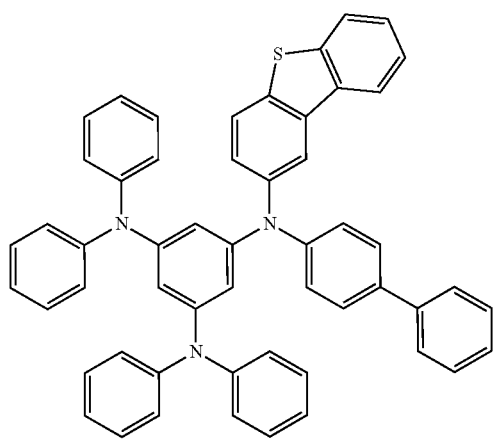
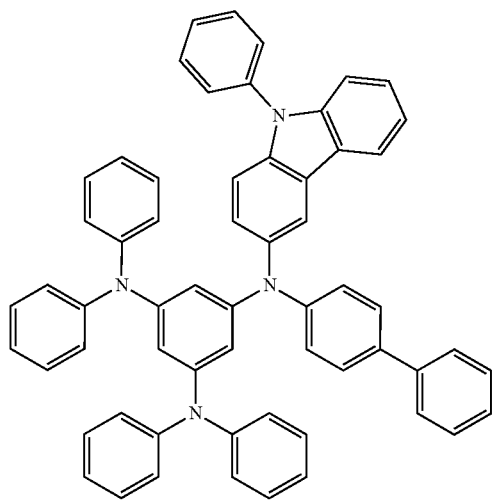
96
-continued
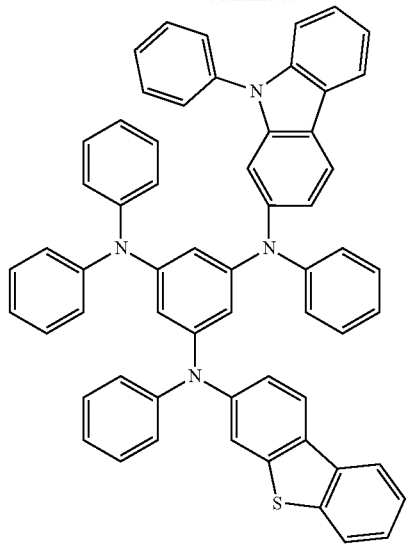
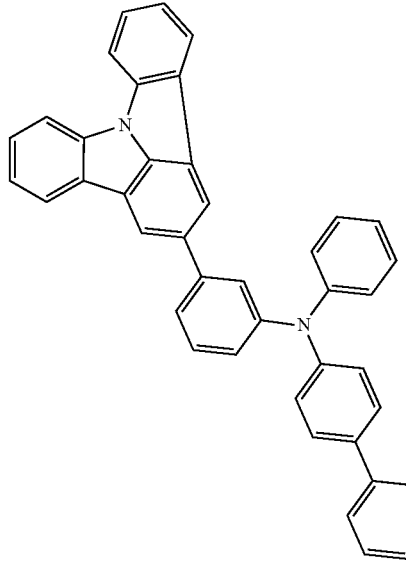
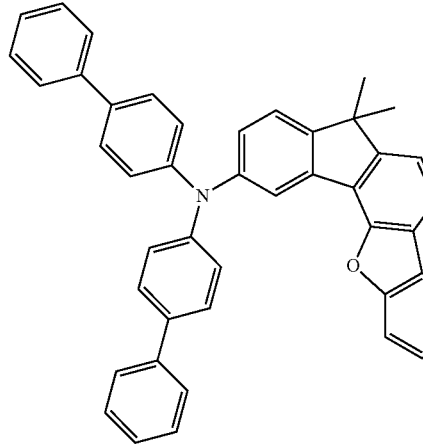

97
-continued
98
-continued
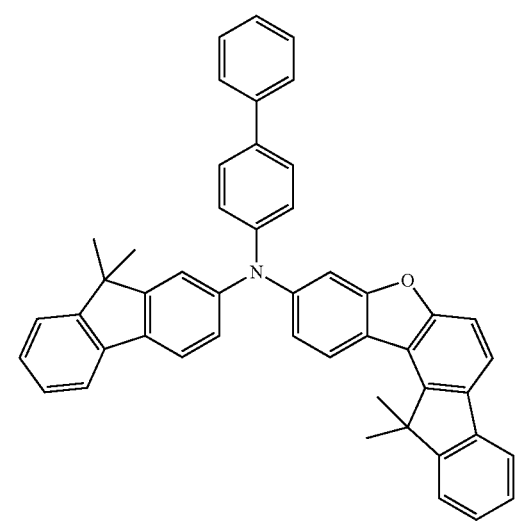
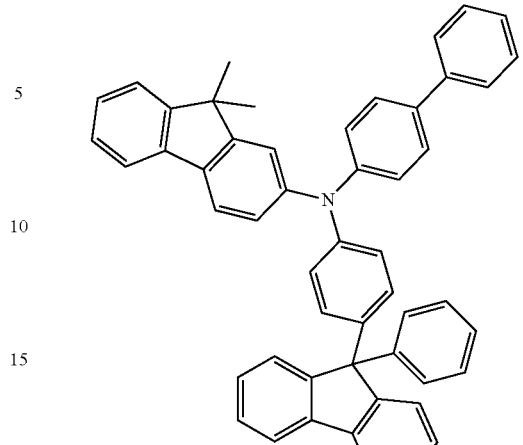
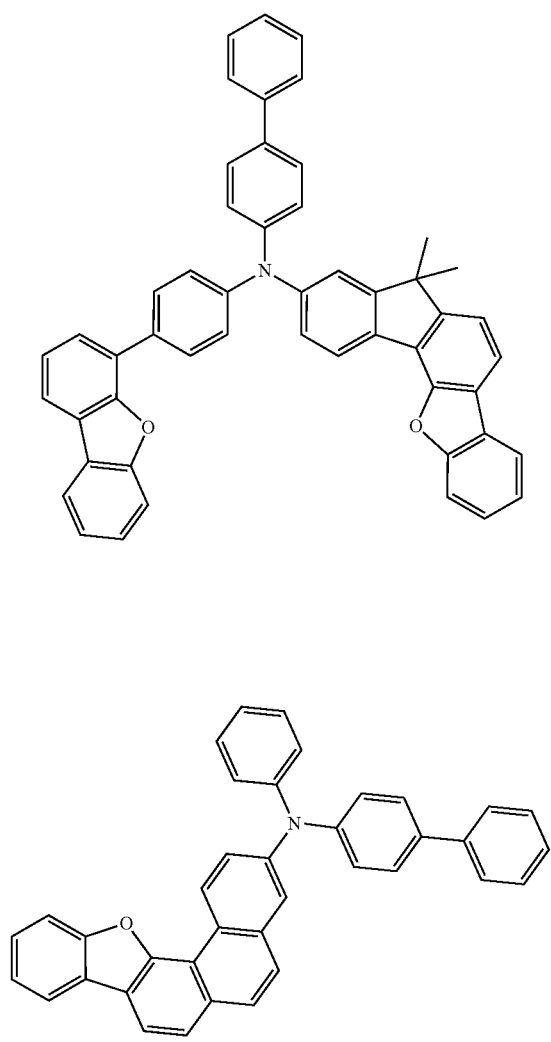
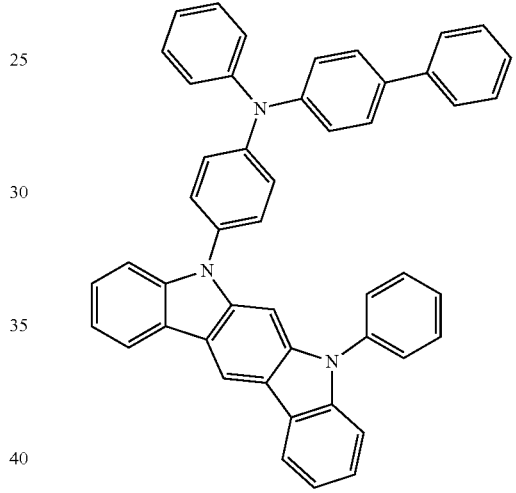
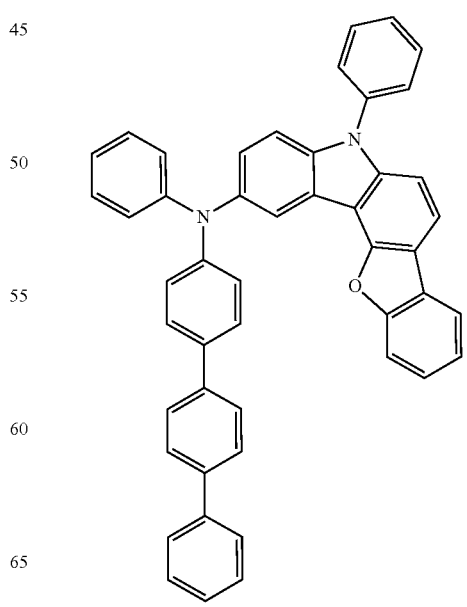

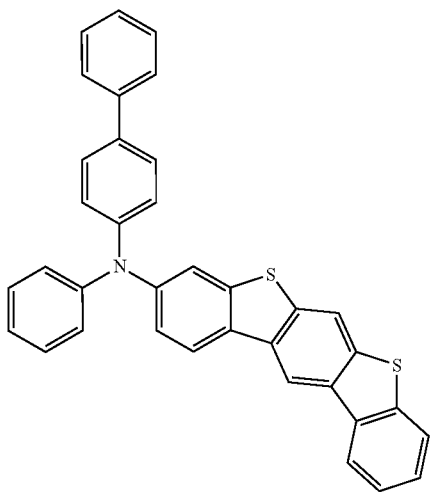
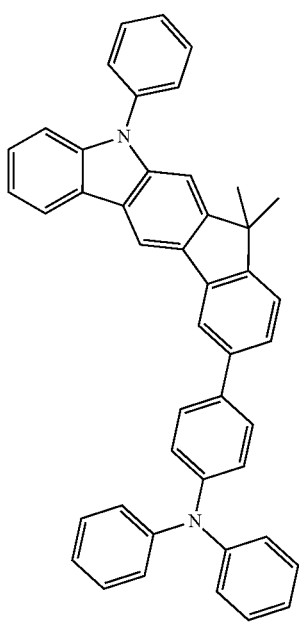
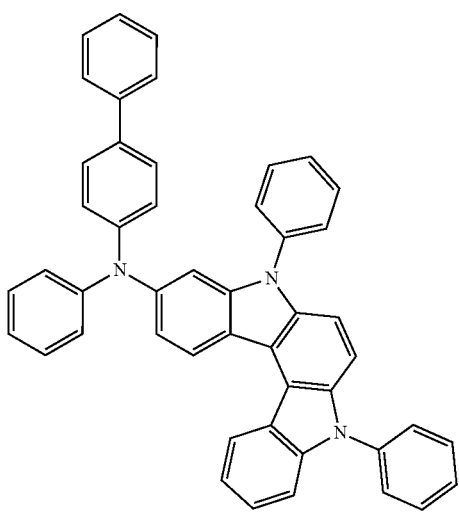
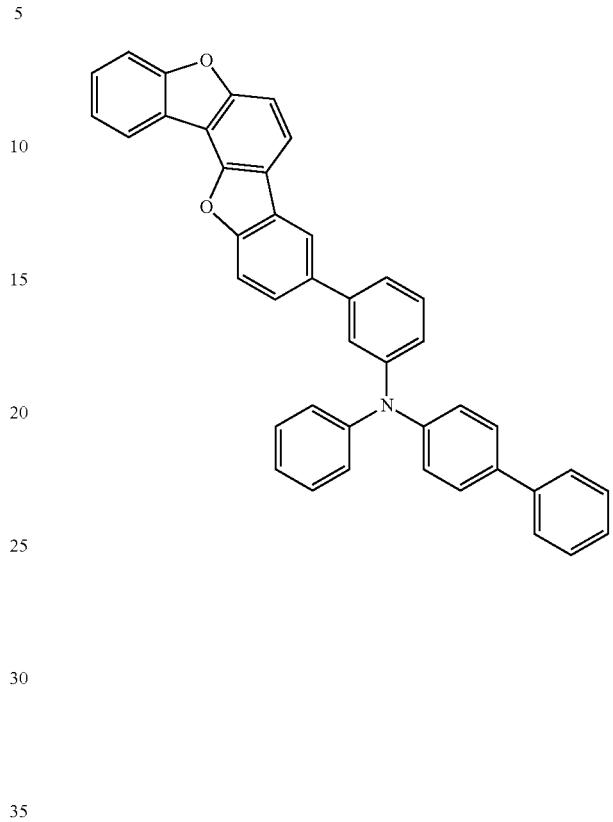

In the hole transport auxiliary layer, other suitable compounds may be included in addition to the aforementioned compounds.

In an implementation, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo chemical industry or P&H tech as far as there in no particular comment or were synthesized by suitable methods.

(Preparation of Compounds for Organic Optoelectronic Device)

Compounds were synthesized through the following steps.

Synthesis of First Compound for Organic Optoelectronic Device

Synthesis Example 1: Synthesis of Compound 2

[Reaction Scheme 1]

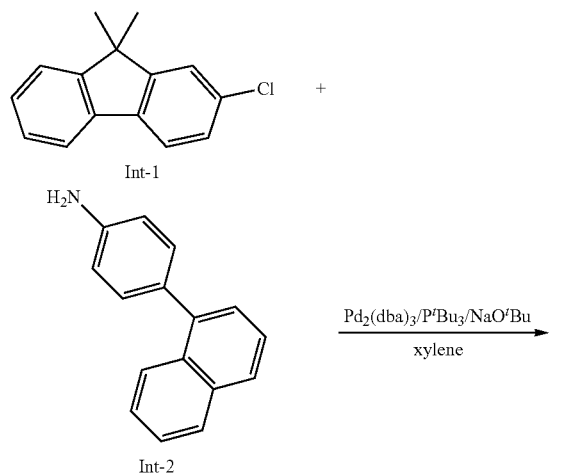

20.0 g (87.4 mmol) of Int-1, 9.2 g (42.0 mmol) of Int-2, 12.6 g (131.2 mmol) of sodium t-butoxide, and 2.7 g (13.1 mmol) of tri-tert-butylphosphine were dissolved in 430 ml of xylene, and 4.0 g (4.4 mmol) of Pd$_2$(dba)$_3$ was added thereto and then, refluxed and stirred under a nitrogen atmosphere for 12 hours. When a reaction was complete, an organic layer was extracted therefrom with xylene and distilled water, dried with anhydrous magnesium sulfate, and filtered, and a filtrate therefrom was concentrated under a reduced pressure. A product therefrom was purified with n-hexane/dichloromethane (a volume ratio of 2:1) through silica gel column chromatography to obtain 43.3 g (Yield: 82%) of Compound 2.

calcd. C46H37N: C, 91.50; H, 6.18; N, 2.32. found: C, 91.51; H, 6.17; N, 2.32.

Synthesis Example 2: Synthesis of Compound 3

[Reaction Scheme 2]

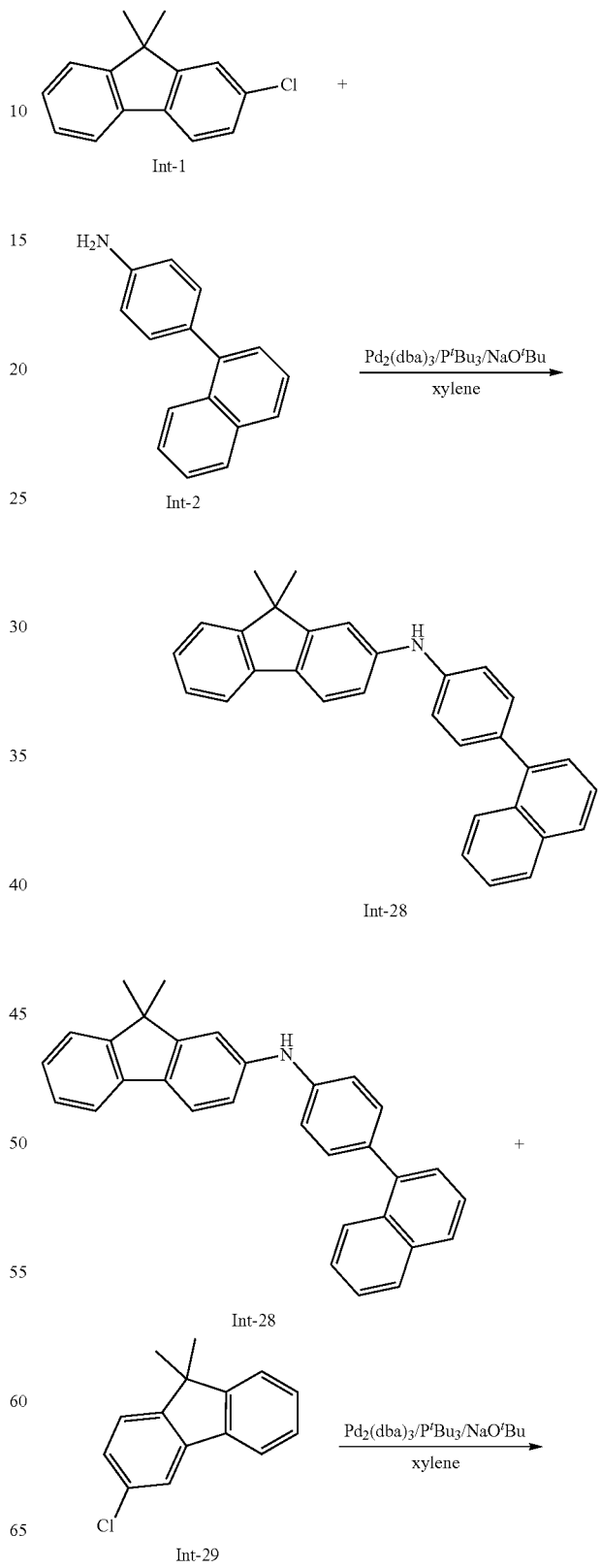

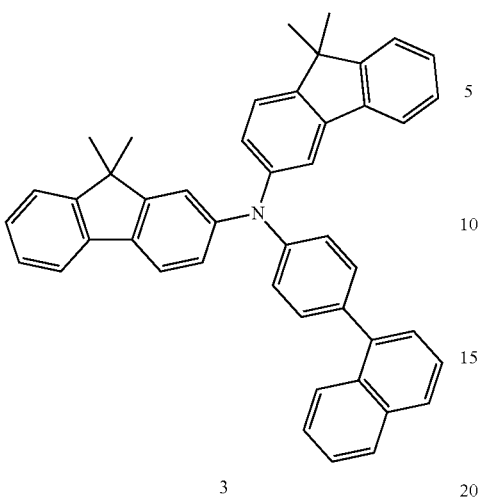

3

1st Step: Synthesis of Intermediate Int-28

Intermediate Int-28 was synthesized according to the same method as Compound 2 of Synthesis Example 1 except that Int-1 and Int-2 were used in an equal mole ratio.

2nd Step: Synthesis of Compound 3

5.65 g (Yield: 70%) of Compound 3 was synthesized according to the same method as Compound 2 of Synthesis Example 1 except that Int-28 and Int-29 were used.

calcd. C46H37N: C, 91.50; H, 6.18; N, 2.32. found C, 91.50; H, 6.18; N, 2.32.

Synthesis Example 3: Synthesis of Compound 43

[Reaction Scheme 3]

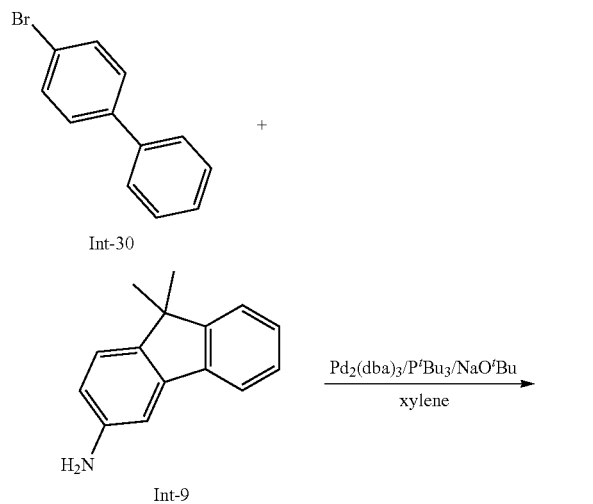

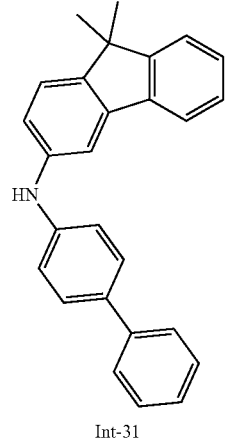

Int-31

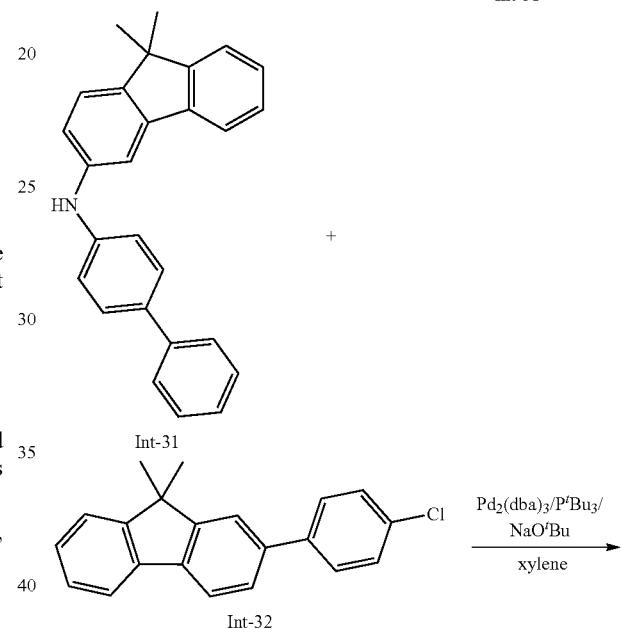

43

1st Step: Synthesis of Intermediate Int-31

Intermediate Int-31 was synthesized according to the same method as Compound 2 of Synthesis Example 1 except that Int-30 and Int-9 were used.

2nd Step: Synthesis of Compound 43

6.05 g (Yield: 70%) of Compound 43 was synthesized according to the same method as Compound 2 of Synthesis Example 1 except that Int-31 and Int-32 were used.

calcd. C48H39N: C, 91.53; H, 6.24; N, 2.22. found C, 91.54; H, 6.23; N, 2.22.

Synthesis Example 4: Synthesis of Compound 47

[Reaction Scheme 4]

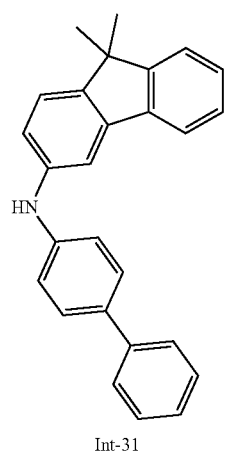

Int-31

+

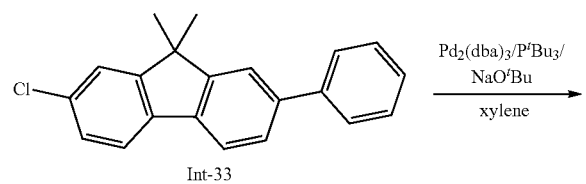

Int-33

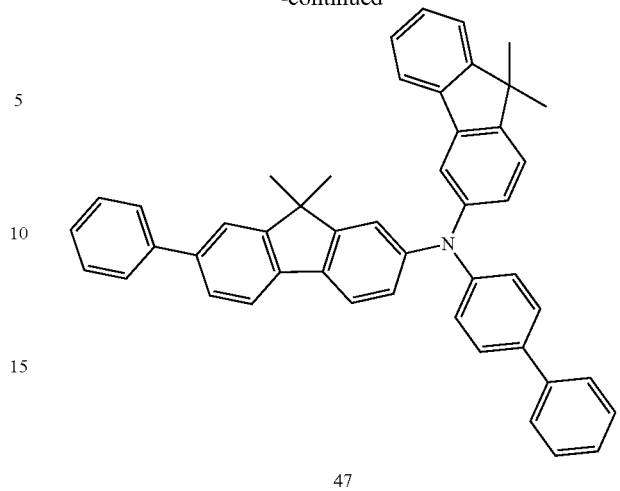

47

6.06 g (Yield: 68%) of Compound 47 was synthesized according to the same method as Compound 2 of Synthesis Example 1 except that Int-31 and Int-32 were used.

calcd. C48H39N: C, 91.53; H, 6.24; N, 2.22. found C, 91.53; H, 6.24; N, 2.22.

Synthesis Examples 5 to 14

Each compound of Synthesis Examples 5 to 7 shown in Table 1 was synthesized according to the same method as Compound 2 of Synthesis Example 1 except that Int-B of Table 1 was used instead of Int-2 of Synthesis Example 1.

Each compound of Synthesis Examples 8 to 13 shown in Table 1 was synthesized according to the same method as Compound 3 of Synthesis Example 2 except that Int-B of Table 1 was used instead of Int-2 of Synthesis Example 2, or Int-A of Table 1 was used instead of Int-29.

A compound of Synthesis Example 14 shown in Table 1 was synthesized according to the same method as Compound 47 of Synthesis Example 4 except Int-34 synthesized by using Int-B of Table 1 instead of Int-2 of Synthesis Example 1 was used instead of Int-31 of Synthesis Example 4.

TABLE 1

| Synthesis Example | Int-A | Int-B | Final product | Amount (yield) | Property data of final product |
|---|---|---|---|---|---|
| Synthesis Example 5 | Int-1 | H$_2$N-⌬-⌬⌬ (Int-4) | Compound 14 | 4.91 g (74%) | calcd. C46H37N: C, 91.50; H, 6.18; N, 2.32 found C, 91.50; H, 6.17; N, 2.33 |

TABLE 1-continued

| Synthesis Example | Int-A | Int-B | Final product | Amount (yield) | Property data of final product |
|---|---|---|---|---|---|
| Synthesis Example 6 | Int-1 | Int-5 (3-(naphthalen-2-yl)aniline) | Compound 18 | 4.53 g (67%) | calcd. C46H37N: C, 91.50; H, 6.18; N, 2.32 found C, 91.50; H, 6.18; N, 2.32 |
| Synthesis Example 7 | Int-1 | Int-6 (4-(6-phenylnaphthalen-2-yl)aniline) | Compound 30 | 4.59 g (77%) | calcd. C52H41N: C, 91.86; H, 6.08; N, 2.06 found C, 91.87; H, 6.07; N, 2.06 |
| Synthesis Example 8 | Int-7 | Int-2 | Compound 4 | 5.88 g 68% | calcd. C46H37N: C, 91.50; H, 6.18; N, 2.32 found C, 91.51; H, 6.17; N, 2.32 |
| Synthesis Example 9 | Int-29 | Int-3 (3-(naphthalen-1-yl)aniline) | Compound 7 | 5.04 g (71%) | calcd. C46H37N: C, 91.50; H, 6.18; N, 2.32 found C, 91.50; H, 6.17; N, 2.33 |
| Synthesis Example 10 | Int-29 | Int-4 | Compound 15 | 4.75 g (74%) | calcd. C46H37N: C, 91.50; H, 6.18; N, 2.32 found C, 91.50; H, 6.18; N, 2.32 |
| Synthesis Example 11 | Int-7 | Int-4 | Compound 16 | 4.99 g (71%) | calcd. C46H37N: C, 91.50; H, 6.18; N, 2.32 found C, 91.51; H, 6.17; N, 2.32 |
| Synthesis Example 12 | Int-29 | Int-5 | Compound 19 | 7.01 g (75%) | calcd. C46H37N: C, 91.50; H, 6.18; N, 2.32 found C, 91.50; H, 6.17; N, 2.33 |
| Synthesis Example 13 | Int-29 | Int-6 | Compound 31 | 5.71 g (70%) | calcd. C52H41N: C, 91.86; H, 6.08; N, 2.06 found C, 91.86; H, 6.08; N, 2.06 |

TABLE 1-continued

| Synthesis Example | Int-A | Int-B | Final product | Amount (yield) | Property data of final product |
|---|---|---|---|---|---|
| Synthesis Example 14 | Int-8 | Int-33 | Compound 55 | 4.15 g (68%) | calcd. C48H39N: C, 91.53; H, 6.24; N, 2.22; found C, 91.53; H, 6.24; N, 2.22 |
| | Int-34 | | | | |

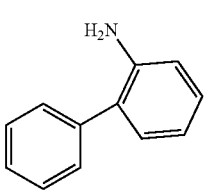

Comparative Synthesis Examples 1 and 2

A compound of Comparative Synthesis Example 1 shown in Table 2 was synthesized according to the same method as Compound 3 of Synthesis Example 2 except that Int-4 was used instead of Int-2 of Synthesis Example 2, and Int-35 was used instead of Int-29 of Synthesis Example 2.

A compound of Comparative Synthesis Example 2 shown in Table 2 was synthesized according to the same method as Compound 2 of Synthesis Example 1 except that Int-29 was used instead of Int-1 of Synthesis Example 1, and Int-9 was used instead of Int-2 of Synthesis Example 1.

TABLE 2

| Synthesis Example | Starting material 1 | Starting material 2 | Final product | Amount (yield) | Property data of final product |
|---|---|---|---|---|---|
| Comparative Synthesis Example 1 | Int-4 | Int-35 | Comparative Compound 1 | 8.95 g, (78%) | calcd. C43H33N: C, 91.61; H, 5.90; N, 2.48 found C, 91.61; H, 5.90; N, 2.48 |

TABLE 2-continued

| Synthesis Example | Starting material 1 | Starting material 2 | Final product | Amount (yield) | Property data of final product |
|---|---|---|---|---|---|
| Comparative Synthesis Example 2 | Int-29 | 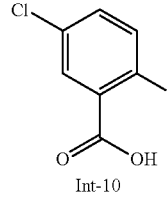<br>Int-9 | 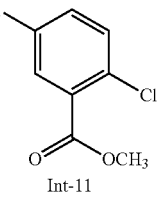<br>Comparative Compound 2 | 3.66 g, (75%) | calcd. C45H39N: C, 91.02; H, 6.62; N, 2.36 found C, 91.02; H, 6.62; N, 2.36 |

Synthesis of Second Compound for Organic Optoelectronic Device

Synthesis Example 15: Synthesis of Compound 81

[Reaction Scheme 5]

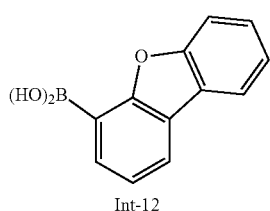

Int-10 → Int-11 (H₂SO₄/MeOH) +

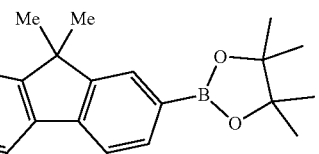
Int-12

Pd(PPh₃)₄, K₂CO₃ →

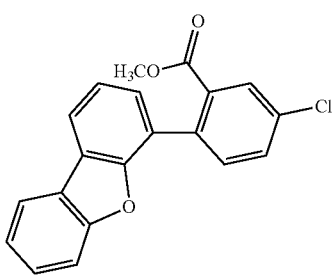
Int-13

1. CH₃MgBr/THF
2. TFA/MC →

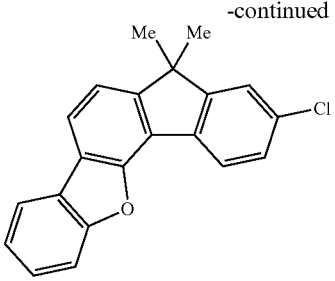
Int-14

Pd(dppf)Cl₂/KOAc, Xylene →

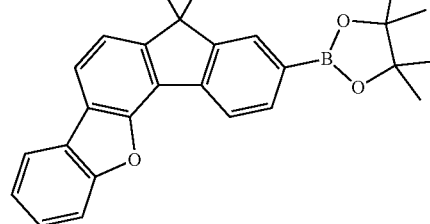
Int-15

+

Int-16

Pd(PPh₃)₄, K₂CO₃ →

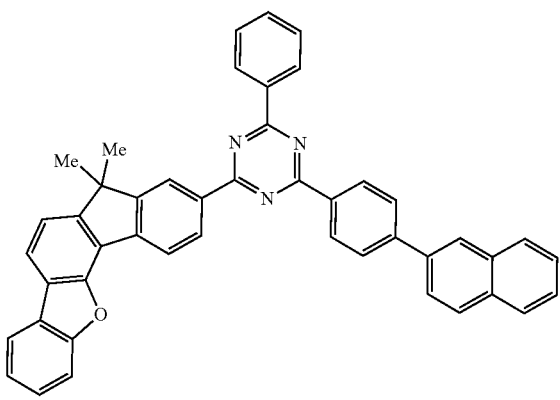

81

1st Step: Synthesis of Int-11

Int-10 (100 g, 523.83 mmol) was dissolved in 1.5 L of MeOH, and sulfuric acid (29.52 ml) was slowly added thereto in a dropwise fashion and then, heated and refluxed at 70° C. for 24 hours. When a reaction was complete, the resultant was concentrated under a reduced pressure and then, dissolved in 1 L of ethyl acetate. The solution was neutralized with NaOH, extracted with ethyl acetate, treated with anhydrous magnesium sulfate to remove moisture therefrom, filtered, and concentrated under a reduced pressure. The obtained residue was separated and purified through flash column chromatography to obtain 100.05 g (Yield: 94%) of Int-11.

2nd Step: Synthesis of Int-13

Int-11 (100.00 g, 487.73 mmol) was dissolved in 1.6 L of tetrahydrofuran (THF), and Int-12 (118.35 g, 487.73 mmol) and tetrakis(triphenylphosphine) palladium (16.91 g, 14.63 mmol) were added thereto and then, stirred. Subsequently, potassium carbonate (168.52 g, 1.22 mol) saturated in 800 ml of water was added thereto and then, heated and refluxed at 80° C. for 12 hours. When a reaction was complete, an organic layer was separated therefrom and concentrated. A mixture obtained therefrom was added to 1 L of methanol, and a solid crystallized therein was filtered, dissolved in monochlorobenzene, filtered with silica gel/Celite, and after removing an appropriate amount of the organic solvent, recrystallized to obtain 124.83 g (Yield: 76%) of Int-13.

3rd Step: Synthesis of Int-14

Int-13 (120.0 g, 356.33 mmol) was dissolved in 1 L of tetrahydrofuran under a nitrogen atmosphere, and a 3 M (296 ml) solution of methylmagnesium bromide (in diethyl ether) was slowly added thereto in a dropwise fashion, while the internal temperature was maintained at 0° C. After stirring the mixture at ambient temperature for 2 hours, the reactant was poured into ice, extracted with ethyl acetate, treated with anhydrous magnesium sulfate to remove moisture, filtered, and concentrated under a reduced pressure. The concentrated solution was dissolved in 1 L of methylene chloride (MC), and 191 ml of trifluoroethanoic acid (TFA) was slowly added in a dropwise fashion and then, stirred at ambient temperature for 12 hours. When a reaction was complete, the resultant was concentrated under a reduced pressure and then, dissolved in 1 L of ethyl acetate. Subsequently, the solution was neutralized with NaOH, extracted with ethyl acetate (EA), treated with anhydrous magnesium sulfate to remove moisture, filtered, and concentrated under a reduced pressure. The obtained residue was separated and purified through flash column chromatography to obtain 89.74 g (Yield: 79%) of Int-14.

4th Step: Synthesis of Int-15

Int-14 (89.0 g, 279.17 mmol) was dissolved in 1.2 L of xylene under a nitrogen atmosphere, and bis(pinacolato)diboron (85.07 g, 335.01 mmol), (1,1'-bis(diphenylphosphine)ferrocene)dichloropalladium (II) (13.68 g, 16.75 mmol), and potassium acetate (82.20 g, 837.52 mmol) were added thereto and then, heated and refluxed at 150° C. for 24 hours. When a reaction was complete, water was added to the reaction solution, and the mixture was filtered and dried in a vacuum oven. The obtained residue was separated and purified through column chromatography to obtain 69 g (Yield: 62%) of Int-15.

5th Step: Synthesis of Compound 81

Int-15 (5.00 g, 12.19 mmol) was dissolved in 40 mL of tetrahydrofuran (THF), and Int-16 (5.49 g, 12.19 mmol) and tetrakis(triphenylphosphine) palladium (0.42 g, 0.37 mmol) were added thereto and then, stirred. Subsequently, potassium carbonate (4.21 g, 30.46 mmol) saturated in 20 ml of water was added thereto and then, stirred at 80° C. for 12 hours. When a reaction was complete, an organic layer was separated therefrom and concentrated. The obtained mixture was added to 150 mL of methanol, and a solid crystallized therein was filtered, dissolved in toluene, filtered with silica gel/Celite, and after removing an appropriate amount of the organic solvent, recrystallized to obtain 5.24 g (Yield: 67%) of Compound 81.

calcd. C46H31N3O: C, 86.09; H, 4.87; N, 6.55; O, 2.49. found C, 86.09; H, 4.87; N, 6.55; 0, 2.49.

Synthesis Examples 16 to 29

Each compound of Synthesis Examples 16 to 19 was synthesized according to the same method as Compound 15 of Synthesis Example 15 except that Int-C of Table 3 was used instead of Int-15 of Synthesis Example 15.

TABLE 3

| Synthesis Example | Int-C | Final product | Amount (yield) | Property data of final product |
|---|---|---|---|---|
| Synthesis Example 16 | Int-17 | Compound 82 | 6.08 g, (70%) | calcd. C46H31N3O: C, 86.09; H, 4.87; N, 6.55; O, 2.49 found C, 86.09; H, 4.87; N, 6.55; O, 2.49 |
| Synthesis Example 17 | Int-18 | Compound 83 | 7.50 g, (75%) | calcd. C46H31N3O: C, 86.09; H, 4.87; N, 6.55; O, 2.49 found C, 86.10; H, 4.87; N, 6.55; O, 2.48 |
| Synthesis Example 18 | Int-19 | Compound 85 | 6.49 g, (65%) | calcd. C46H31N3O: C, 86.09; H, 4.87; N, 6.55; O, 2.49 found C, 86.09; H, 4.87; N, 6.55; O, 2.49 |
| Synthesis Example 19 | Int-20 | Compound 94 | 6.04 g, (69%) | calcd. C45H33N3S: C, 83.43; H, 5.13; N, 6.49; S, 4.95; found C, 83.44; H, 5.13; N, 6.49; S, 4.94 |

Comparative Synthesis Examples 3 to 5

Each compound of Comparative Synthesis Example 3 to 5 shown in Table 4 was synthesized according to the same method as Compound 81 of Synthesis Example 15 except that Int-D of Table 4 was used instead of Int-15 of Synthesis Example 15, and Int-E of Table 4 was used instead of Int-16 of Synthesis Example 15.

TABLE 4

| Synthesis Example | Int-D | Int-E | Final product | Amount (yield) | Property data of final product |
|---|---|---|---|---|---|
| Comparative Synthesis Example 3 | Int-21 | Int-36 | Comparative Compound 3 | 5.66 g, (74%) | calcd. C42H29N3O: C, 85.25; H, 4.94; N, 7.10; O, 2.70 found C, 85.25; H, 4.94; N, 7.10; O, 2.70 |
| Comparative Synthesis Example 4 | Int-22 | Int-36 | Comparative Compound 4 | 3.28 g, (47%) | calcd. C39H25N5: C, 83.10; H, 4.47; N, 12.42 found C, 83.11; H, 4.46; N, 12.42 |

TABLE 4-continued

| Synthesis Example | Int-D | Int-E | Final product | Amount (yield) | Property data of final product |
|---|---|---|---|---|---|
| Comparative Synthesis Example 5 | Int-23 | Int-36 | Comparative Compound 5 | 9.53 g, (75%) | calcd. C33H20N4O: C, 81.13; H, 4.13; N, 11.47; O, 3.27 found C, 81.13; H, 4.13; N, 11.47; O, 3.27 |

(Manufacture of Organic Light Emitting Diode)

Example 1

The glass substrate coated with ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 1% NDP-9 (available from Novaled) was vacuum-deposited on the ITO substrate to form a 1,400 Å-thick hole transport layer, and Compound B was deposited to be 600 Å-thick on the hole transport layer to form a hole transport auxiliary layer. On the hole transport auxiliary layer, 400 Å-thick light emitting layer was formed by using Compound 2 of Synthesis Example 1 and Compound 81 of Synthesis Example 15 simultaneously as a host and 2 wt % of [Ir(piq)$_2$acac] as a dopant by a vacuum-deposition. Compound 2 and Compound 81 were used in a weight ratio of 5:5. Subsequently, Compound C was deposited at a thickness of 50 Å on the light emitting layer to form an electron transport auxiliary layer, and Compound D and LiQ were simultaneously vacuum-deposited in a weight ratio of 1:1 to form a 300 Å-thick electron transport layer. On the electron transport layer, Liq and Al were sequentially vacuum-deposited to be 15 Å-thick and 1,200 Å-thick, manufacturing an organic light emitting diode.

ITO/Compound A (1% NDP-9 doping, 1,400 Å)/Compound B (600 Å)/EML [mixture of Compound 2 and Compound 81 in a 5:5 weight ratio: [Ir(piq)2acac]=98 wt %: 2 wt %] (400 Å)/Compound C (50 Å)/Compound D: Liq (300 Å)/LiQ (15 Å)/Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Examples 2 to 5 and Comparative Examples 1 to 5

Diodes of Examples 2 to 5 and Comparative Examples 1 to 5 were respectively manufactured according to the same method as Example 1 except that the host was changed as shown in Table 5.

Evaluation

Driving voltages, efficiency, and life-span characteristics of the organic light emitting diodes according to Examples 1 to 5 and Comparative Examples 1 to 5 were evaluated. Specific measurement methods are as follows, and the results are shown in Table 5.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance and current density from the items (1) and (2).

(4) Measurement of Life-Span

The luminance (cd/m$^2$) was maintained at 5000 cd/m$^2$ and the time at which the current efficiency (cd/A) decreased to 90% was measured to obtain results.

(5) Measurement of Driving Voltage

A driving voltage of each diode was measured by using a current-voltage meter (Keithley 2400) at 15 mA/cm$^2$.

(6) Calculation of T90 Life-Span Ratio (%)

Relative values of each T90 (h) were calculated based on T90 (h) of Comparative Example 2 in Table 5 and then, shown in Table 5.

(7) Calculation of Driving Voltage Ratio (%)

Relative values of the driving voltages were calculated based on the driving voltage of Comparative Example 2 in Table 5 and are shown in Table 5.

(8) Calculation of Luminous Efficiency Ratio (%)

Relative values of each luminous efficiency (cd/A) was calculated based on the luminous efficiency (cd/A) of Comparative Example 2 in Table 5 and are shown in Table 5.

TABLE 5

| | First host | Second host | Driving voltage (V) | Luminous efficiency (cd/A) | Life-span T90 (h) |
|---|---|---|---|---|---|
| Example 1 | 2 | 81 | 96% | 113% | 129% |
| Example 2 | 47 | 81 | 97% | 111% | 131% |
| Example 3 | | 82 | 96% | 112% | 130% |
| Example 4 | | 85 | 99% | 109% | 117% |
| Example 5 | | 94 | 96% | 110% | 125% |
| Comparative Example 1 | Comparative Compound 1 | 81 | 117% | 99% | 81% |
| Comparative Example 2 | Comparative Compound 2 | | 100% | 100% | 100% |
| Comparative Example 3 | 47 | Comparative Compound 3 | 104% | 97% | 89% |
| Comparative Example 4 | | Comparative Compound 4 | 107% | 98% | 83% |
| Comparative Example 5 | | Comparative Compound 5 | 110% | 99% | 87% |

Referring to Table 5, the devices of the Examples exhibited greatly improved driving voltage, luminous efficiency, and life-span, compared with the Comparative Examples.

One or more embodiments may provide a composition for an organic optoelectronic device capable of implementing a high efficiency and long life-span organic optoelectronic device.

Organic optoelectronic devices having high efficiency and long life-span may be implemented.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composition for an organic optoelectronic device, the composition comprising:
a first compound represented by Chemical Formula 1 and a second compound represented by a combination of Chemical Formula 2 and Chemical Formula 3:

[Chemical Formula 1]

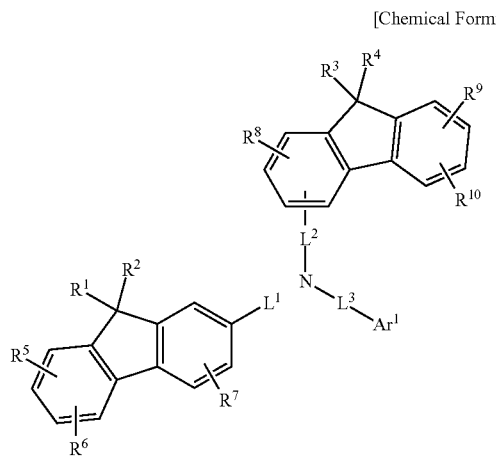

wherein, in Chemical Formula 1,
$Ar^1$ is a substituted or unsubstituted C6 to C30 aryl group, a substituted or unsubstituted C2 to C30 heteroaryl group, or a combination thereof,
$L^1$ to $L^3$ are each independently a single bond or a substituted or unsubstituted C6 to C30 arylene group,
$R^1$ to $R^4$ are each independently a substituted or unsubstituted C1 to C30 alkyl group, a substituted or unsubstituted C6 to C30 aryl group, or a combination thereof,
$R^5$ to $R^{10}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof;

[Chemical Formula 2]

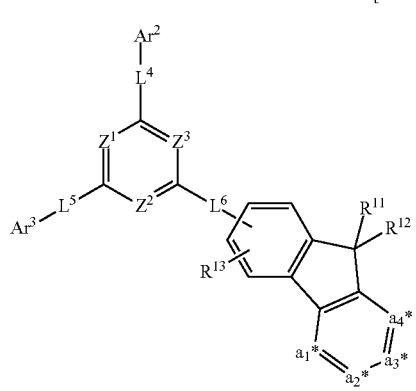

[Chemical Formula 3]

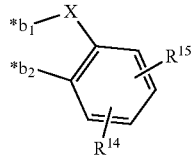

wherein, in Chemical Formula 2 and Chemical Formula 3,
a1* to a4* of Chemical Formula 2 are each independently a linking carbon or $CR^a$, provided that a1* and a2*; a2* and a3*; or a3* and a4* of Chemical Formula 2 are linking carbons linked at *b1 and b2 of Chemical Formula 3,
$Z^1$ to $Z^3$ are each independently N or $CR^b$, and at least one of $Z^1$ to $Z^3$ is N,
X is O, S, or $CR^cCR^d$,
$Ar^1$ and $Ar^3$ are each independently a substituted or unsubstituted C6 to C30 aryl group, a substituted or unsubstituted C2 to C30 heteroaryl group, or a combination thereof,
$L^4$ to $L^6$ are each independently a single bond or a substituted or unsubstituted C6 to C30 arylene group,
$R^c$, $R^d$, $R^{11}$, and $R^{12}$ are each independently a substituted or unsubstituted C1 to C30 alkyl group, a substituted or unsubstituted C6 to C30 aryl group, or a combination thereof, and
$R^a$, $R^b$, and $R^{13}$ to $R^{15}$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof.

2. The composition as claimed in claim 1, wherein the first compound is represented by one of Chemical Formula 1-1 to Chemical Formula 1-4:

[Chemical Formula 1-1]

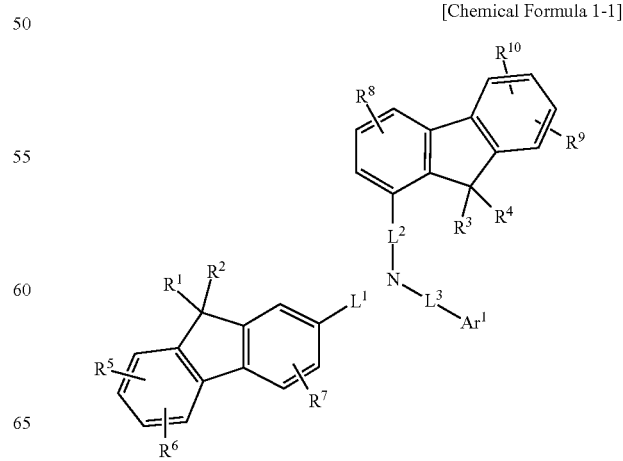

-continued

[Chemical Formula 1-2]

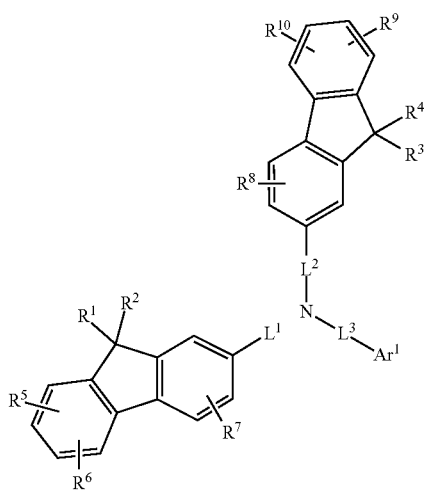

[Chemical Formula 1-3]

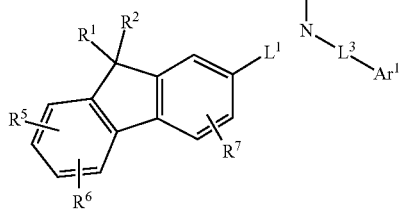

[Chemical Formula 1-4]

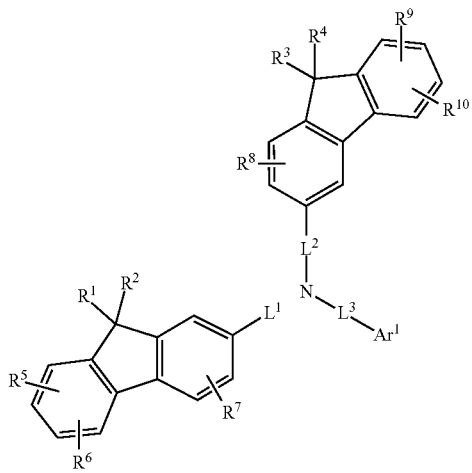

wherein, in Chemical Formulae 1-1 to 1-4, Ar$^1$, L$^1$ to L$^3$, and R$^1$ to R$^{10}$ are defined the same as those of Chemical Formula 1.

3. The composition as claimed in claim 1, wherein Ar$^1$ in Chemical Formula 1 is a substituted or unsubstituted phenyl group, a substituted or unsubstituted biphenyl group, or a substituted or unsubstituted naphthyl group.

4. The composition as claimed in claim 1, wherein Ar$^1$ in Chemical Formula 1 is a substituent of the following Group I:

[Group I]

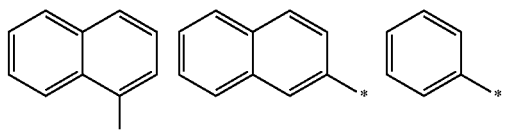

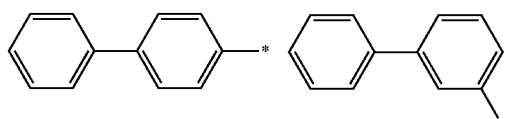

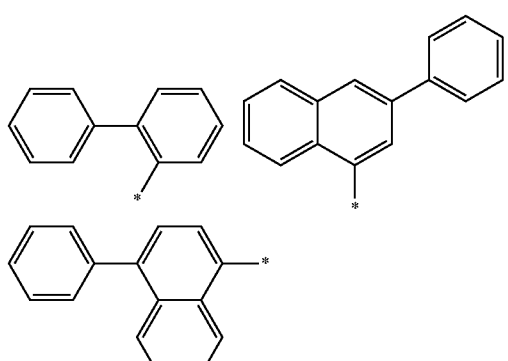

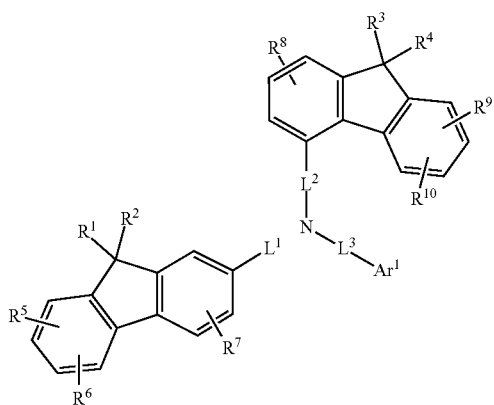

wherein, in Group I, * is a linking point.

5. The composition as claimed in claim 1, wherein the second compound is represented by Chemical Formula 2A or Chemical Formula 2F:

[Chemical Formula 2A]

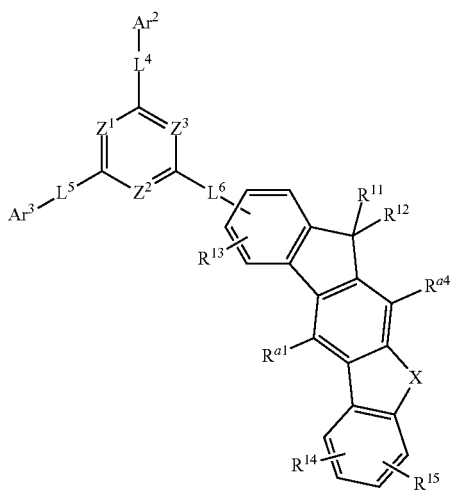

127
-continued

[Chemical Formula 2F]

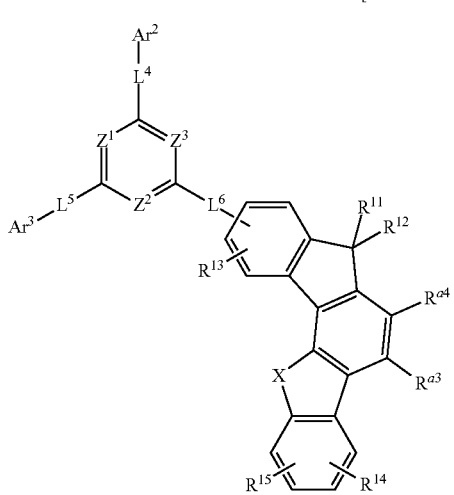

128
-continued

[Chemical Formula 2F-2]

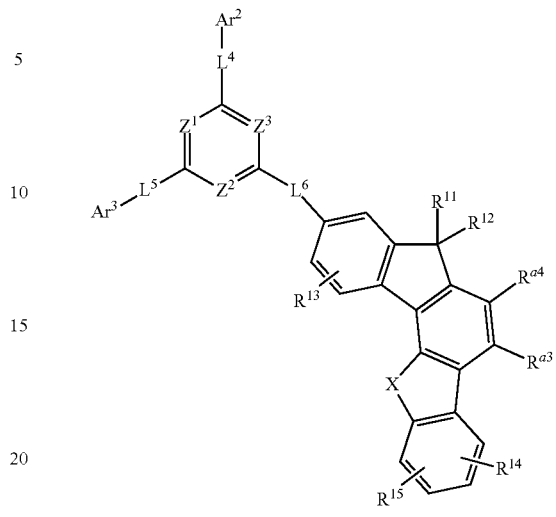

wherein, in Chemical Formula 2A and Chemical Formula 2F, $Z^1$ to $Z^3$, X, $Ar^2$, $Ar^3$, $L^4$ to $L^6$, and $R^{11}$ to $R^{15}$ are defined the same as those of Chemical Formulae 2 and 3, $R^{a1}$ to $R^{a4}$ are defined the same as $R^a$ of Chemical Formulae 2 and 3.

6. The composition as claimed in claim 5, wherein the second compound is represented by Chemical Formula 2A-2, Chemical Formula 2F-2, or Chemical Formula 2F-4:

[Chemical Formula 2A-2]

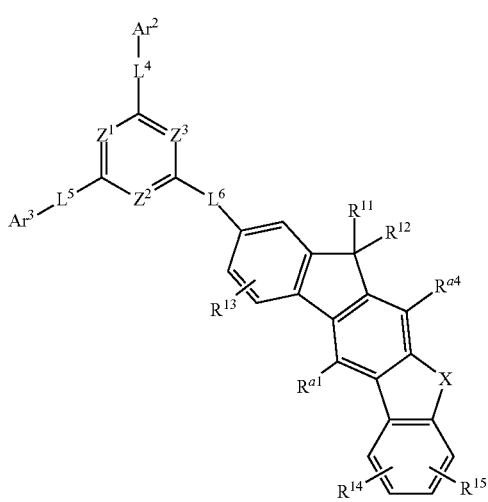

[Chemical Formula 2F-4]

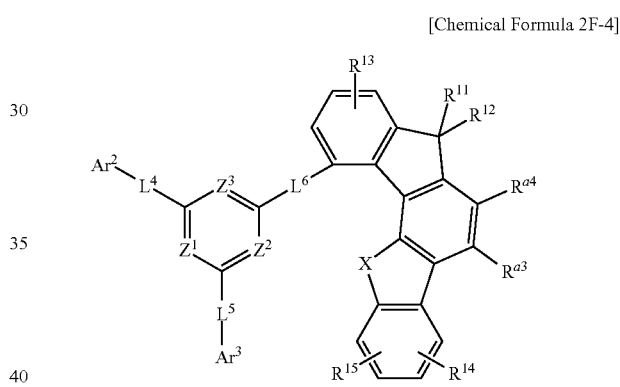

wherein, in Chemical Formula 2A-2, Chemical Formula 2F-2, and Chemical Formula 2F-4, $Z^1$ to $Z^3$, X, $Ar^2$, $Ar^3$, $L^4$ to $L^6$, $R^{11}$ to $R^{15}$ and $R^{a1}$ to $R^{a4}$ are defined the same as those of Chemical Formula 2A and Chemical Formula 2F.

7. The composition as claimed in claim 1, wherein $Ar^2$ and $Ar^3$ of Chemical Formula 2 are each independently a substituted or unsubstituted phenyl group, a substituted or unsubstituted biphenyl group, a substituted or unsubstituted naphthyl group, a substituted or unsubstituted triphenylene group, a substituted or unsubstituted fluorenyl group, a substituted or unsubstituted benzofluorenyl group, a substituted or unsubstituted dibenzofuranyl group, or a substituted or unsubstituted dibenzothiophenyl group.

8. The composition as claimed in claim 1, wherein:

the first compound is represented by Chemical Formula 1-3a, and the second compound is represented by Chemical Formula 2A-2, Chemical Formula 2F-2, or Chemical Formula 2F-4:

[Chemical Formula 1-3a]

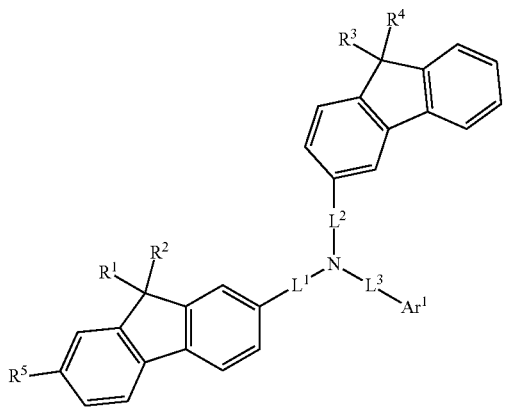

[Chemical Formula 2F-2]

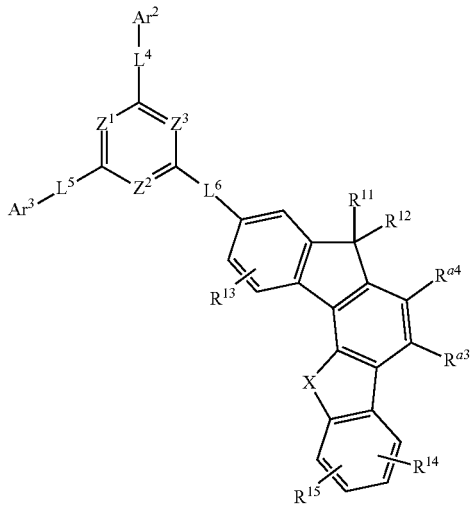

wherein, in Chemical Formula 1-3a, $Ar^1$ is a substituted or unsubstituted C6 to C30 aryl group, a substituted or unsubstituted C2 to C30 heteroaryl group, or a combination thereof, $R^1$ to $R^4$ are each independently a substituted or unsubstituted methyl group or a substituted or unsubstituted phenyl group, $R^5$ is hydrogen or a substituted or unsubstituted phenyl group, and $L^1$ to $L^3$ are each independently a single bond or a substituted or unsubstituted phenylene group;

[Chemical Formula 2F-4]

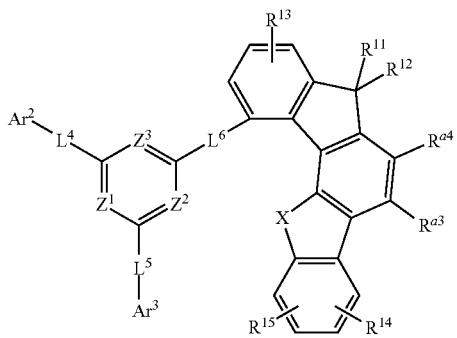

[Chemical Formula 2A-2]

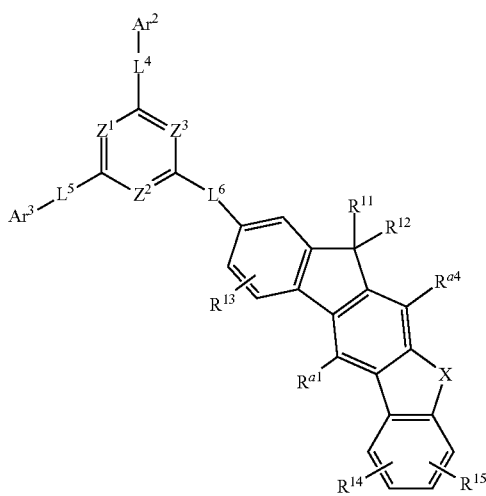

wherein, in Chemical Formula 2A-2, Chemical Formula 2F-2, and Chemical Formula 2F-4, $Z^1$ to $Z^3$ are each independently N or $CR^b$, and at least one of $Z^1$ to $Z^3$ is N, X is O, S, or $CR^cCR^d$, $Ar^2$ and $Ar^3$ are each independently a substituted or unsubstituted phenyl group, a substituted or unsubstituted naphthyl group, or a substituted or unsubstituted fluorenyl group, $R^b$, $R^c$, $R^d$, $R^{11}$, and $R^{12}$ are each independently a substituted or unsubstituted methyl group or a substituted or unsubstituted phenyl group, $L^4$ to $L^6$ are each independently a single bond or a substituted or unsubstituted phenylene group, and $R^{a3}$, $R^{a4}$, and $R^{13}$ to $R^{15}$ are each hydrogen.

9. The composition as claimed in claim 1, wherein the first compound is a compound of the following Group 1:
[Group 1]
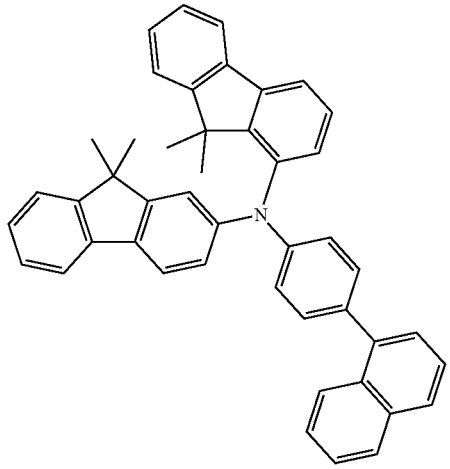
1
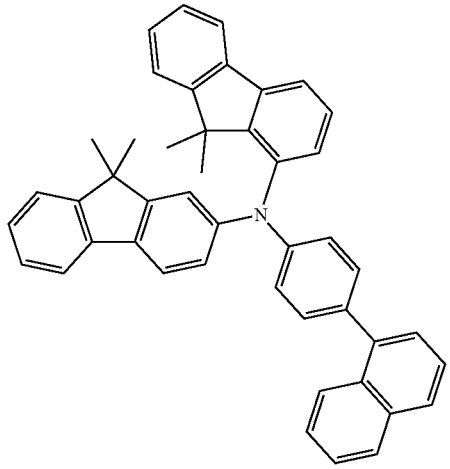
2
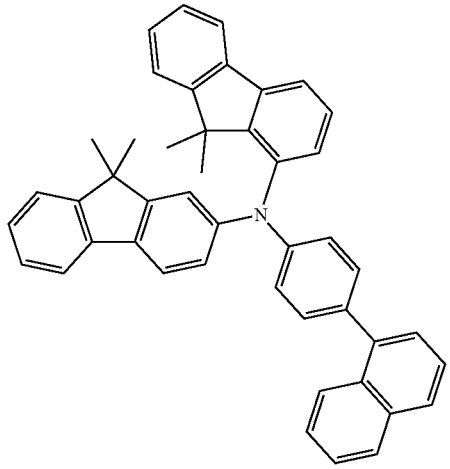
3
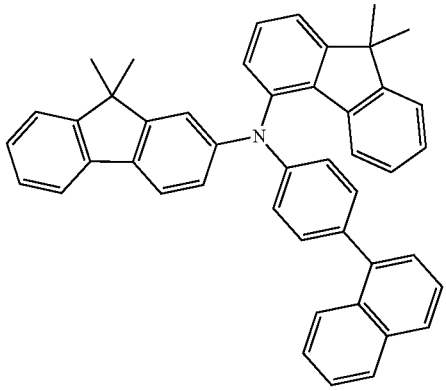
4
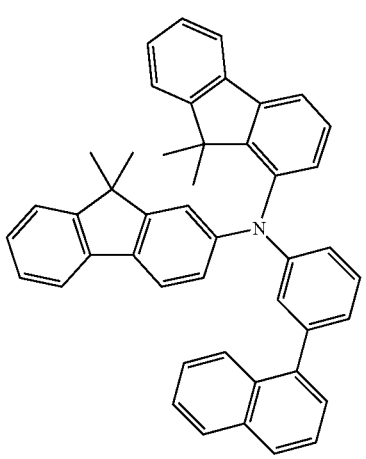
5
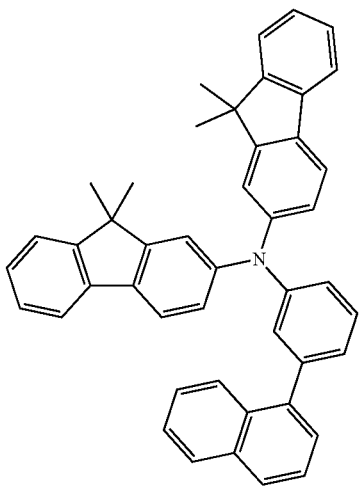
6

-continued
7
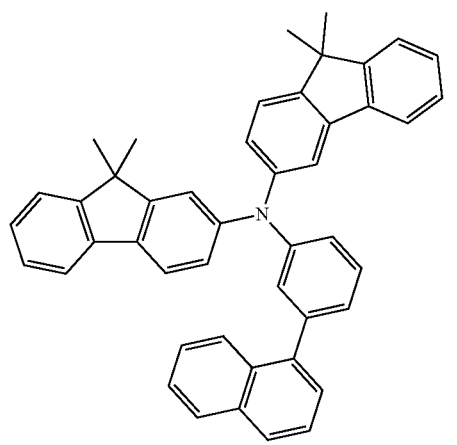
8
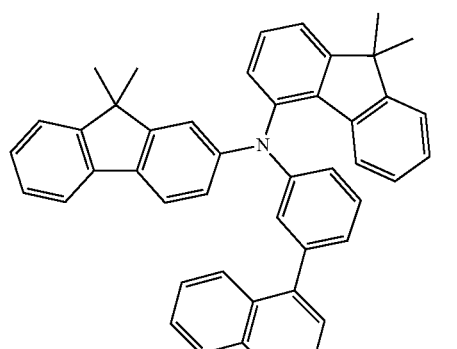
9
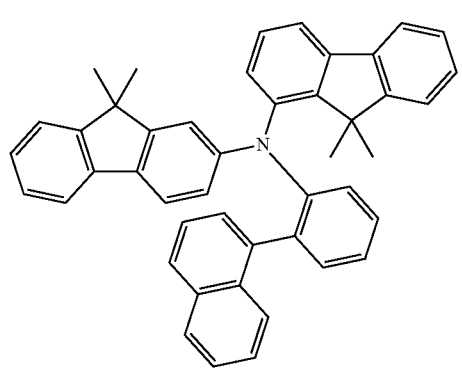
10
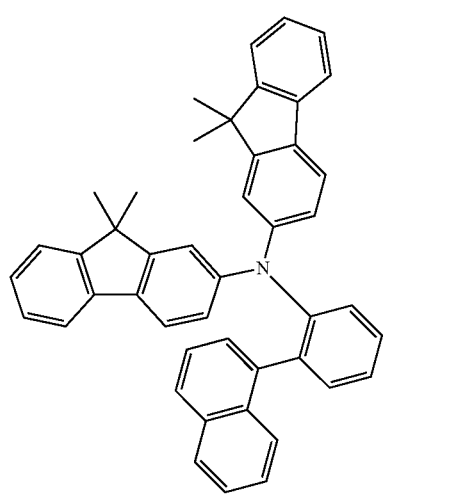
-continued
11
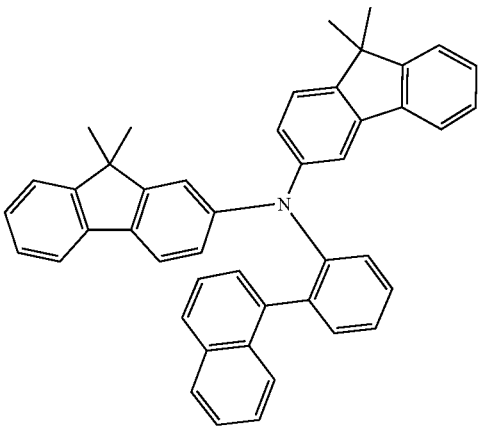
12
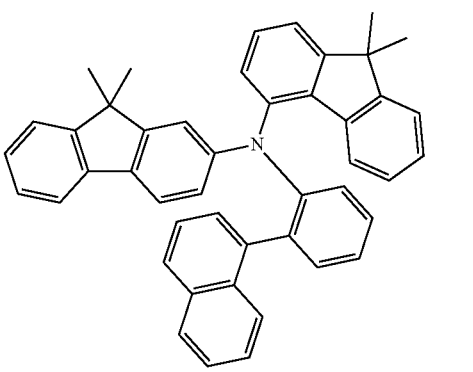
13
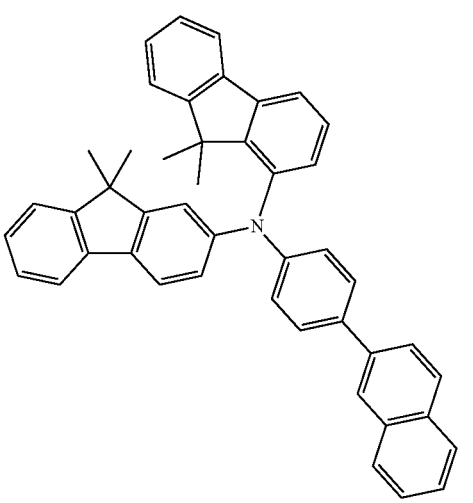

14
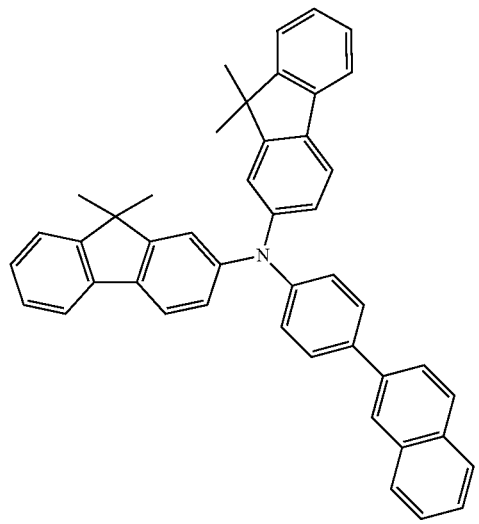
15
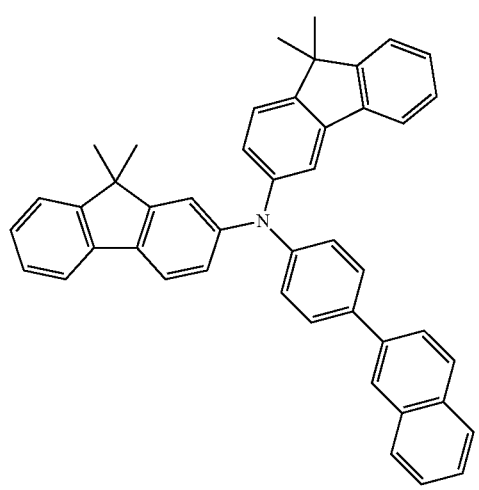
16
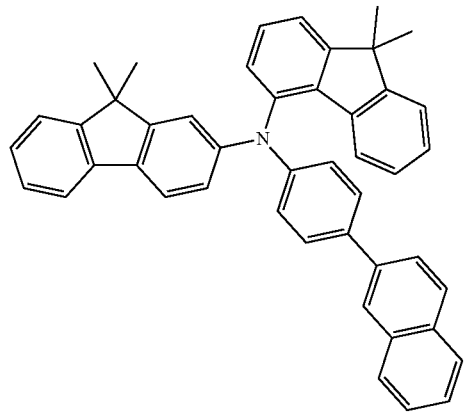
17
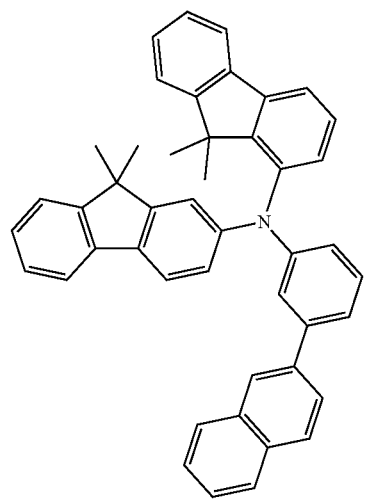
18
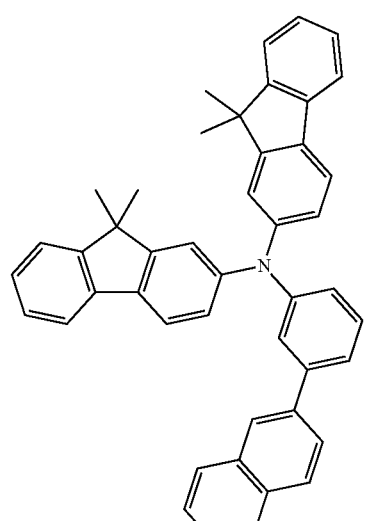
19
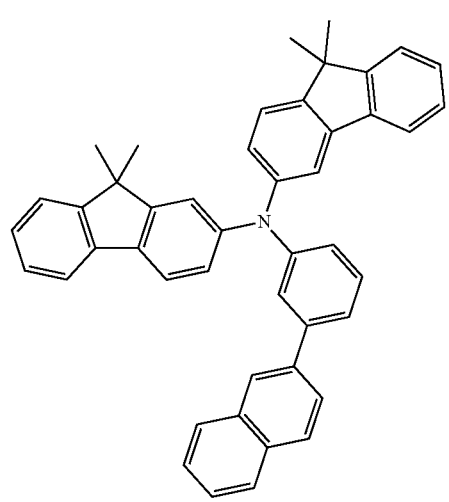

20
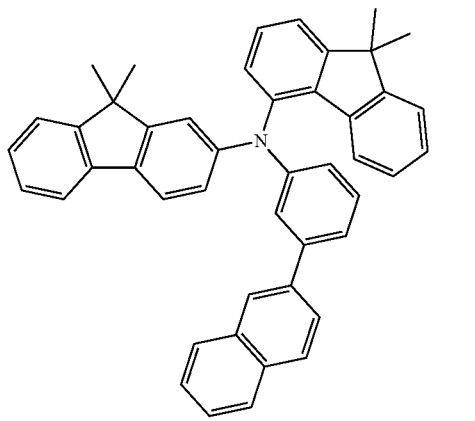
21
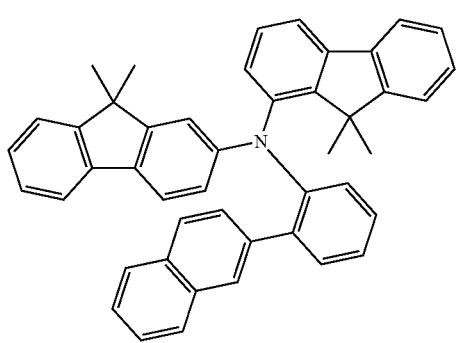
22
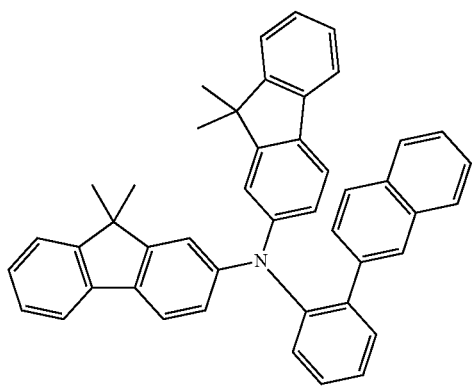
23
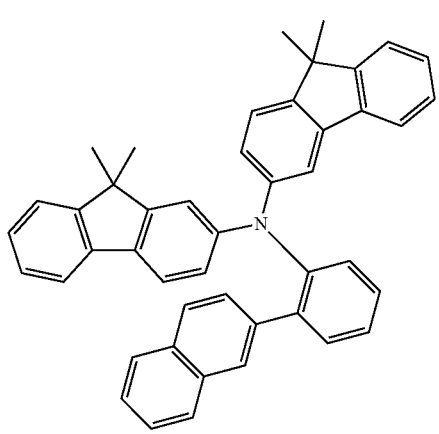
24
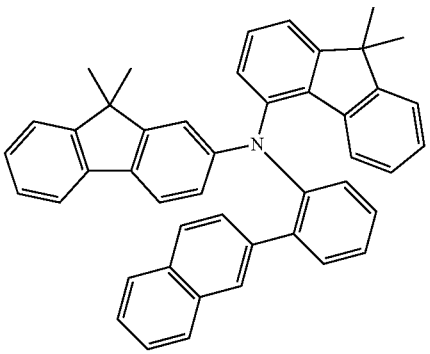
25
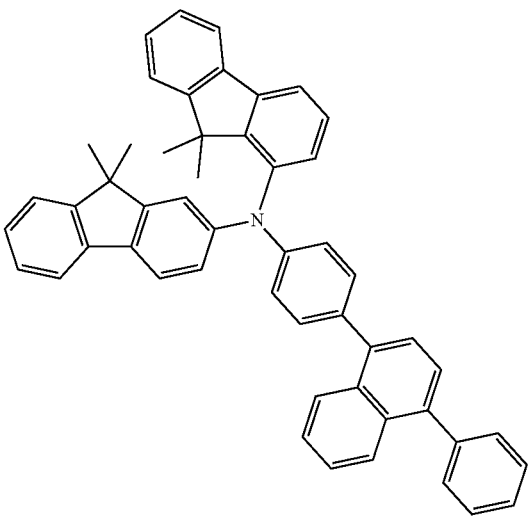
26
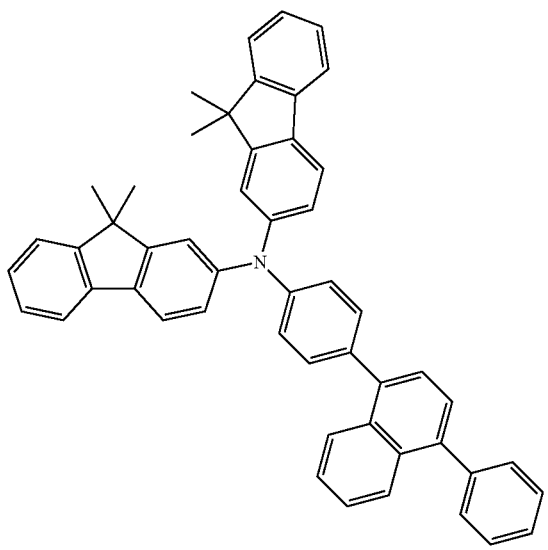

27
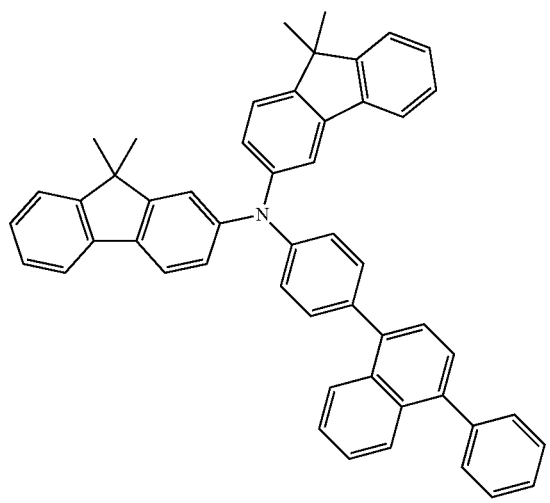
28
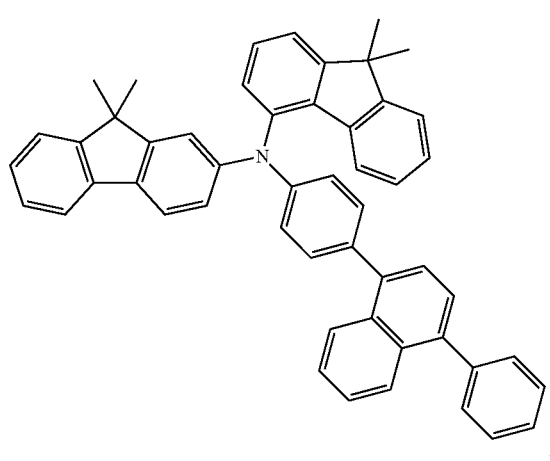
29
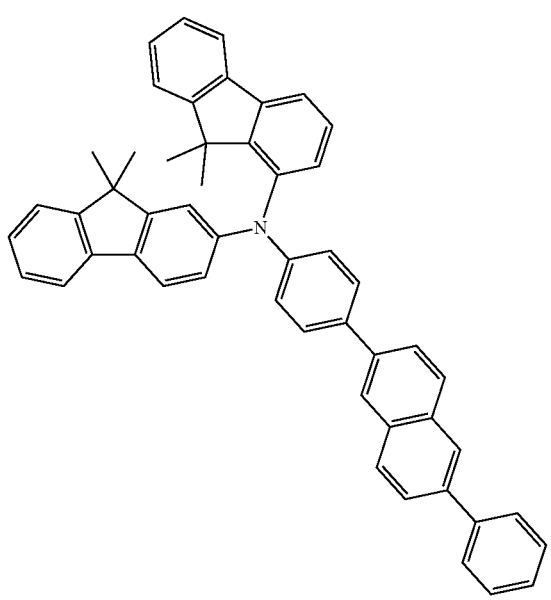
30
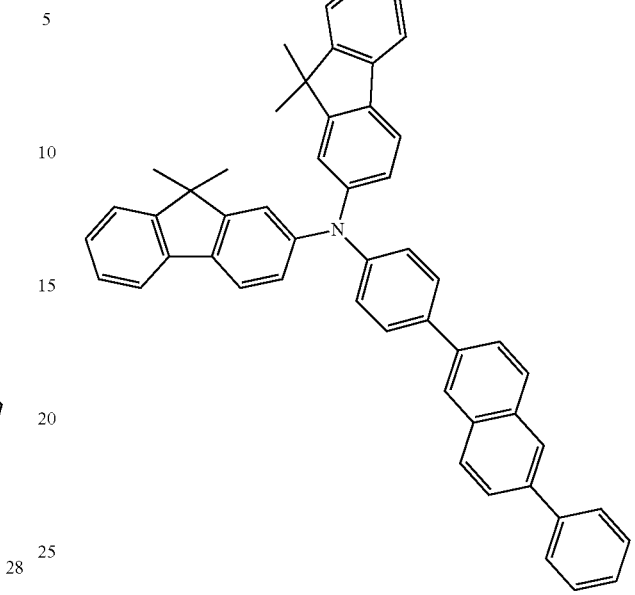
31
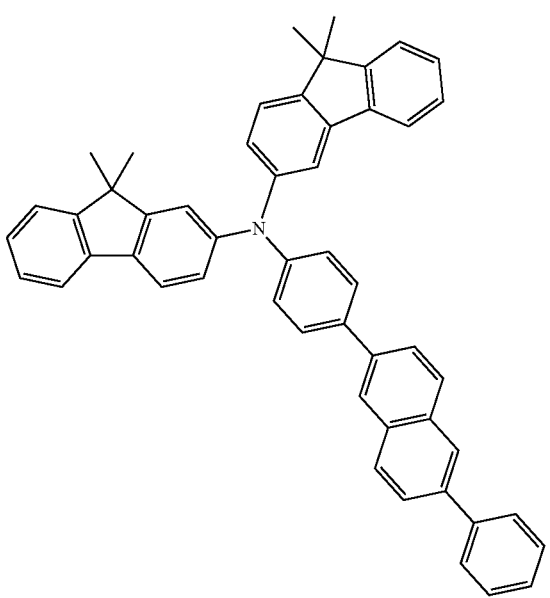

-continued
32
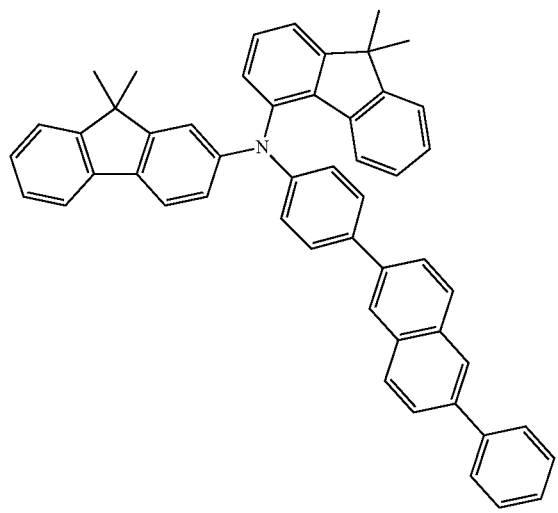
35
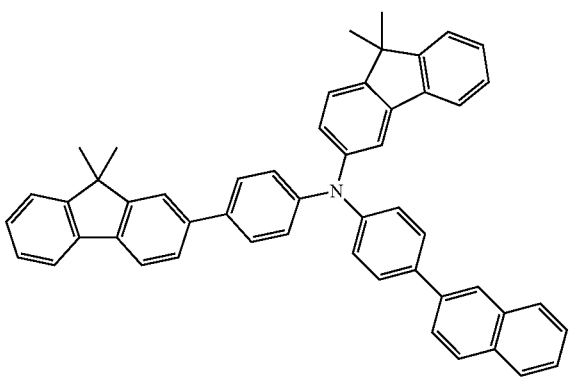
33
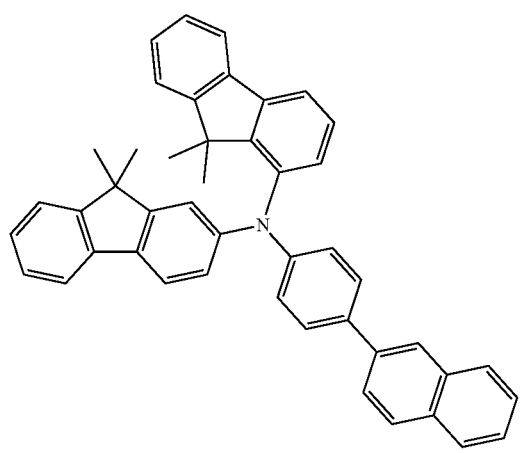
36
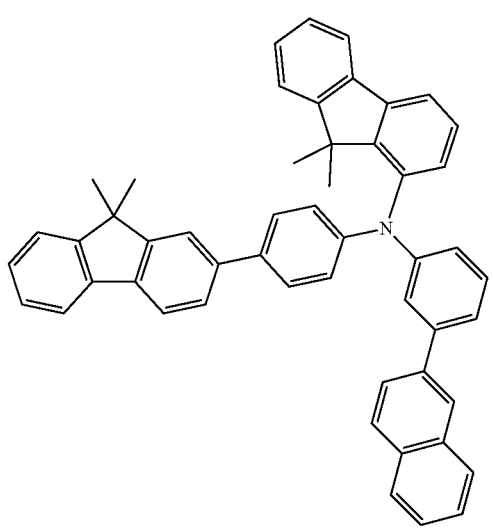
34
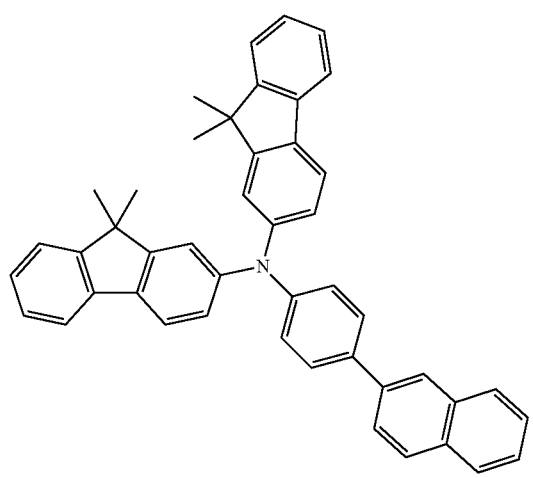
37

38
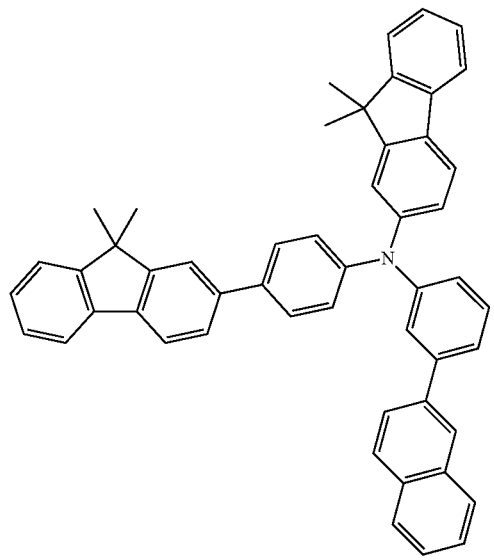
39
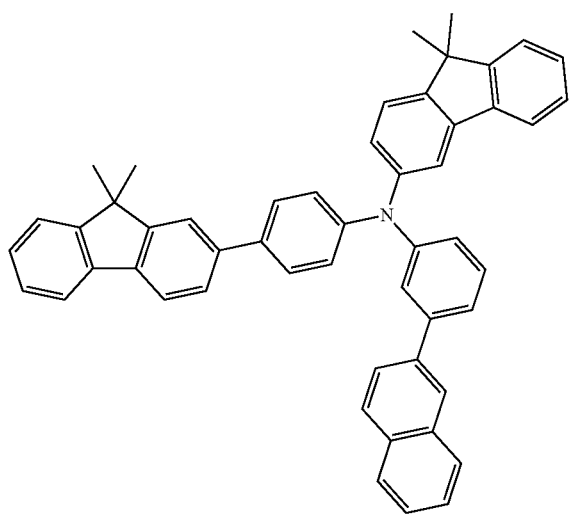
40
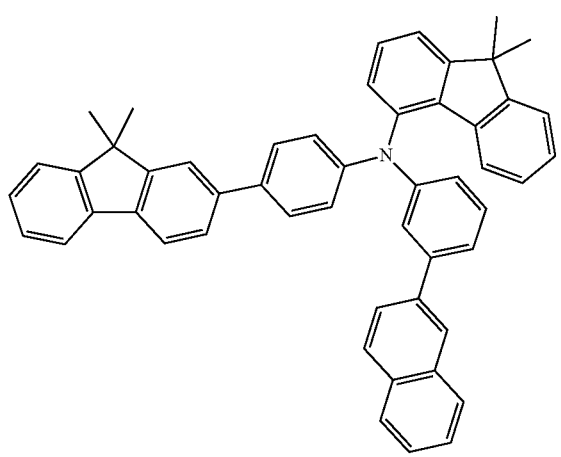
41
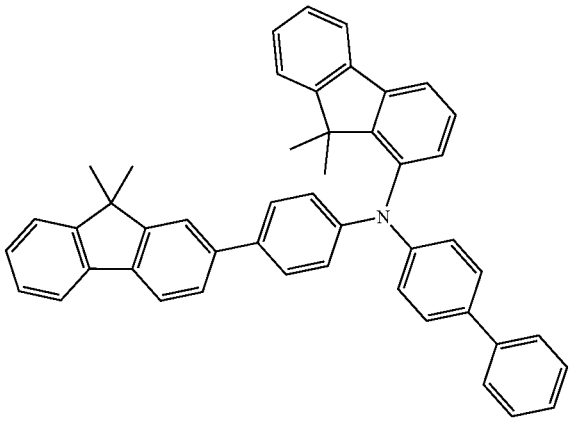
42
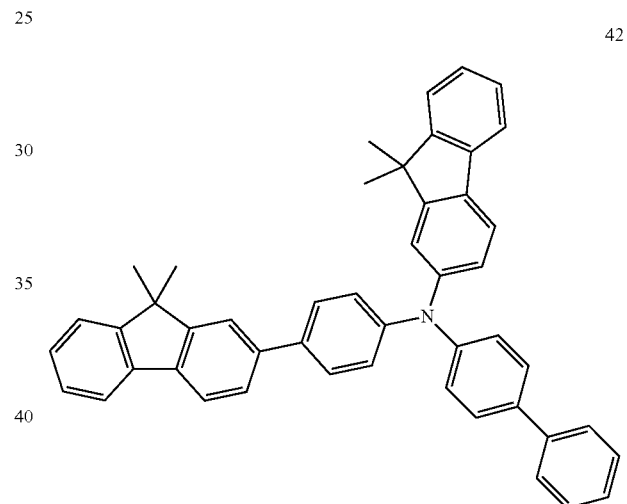
43
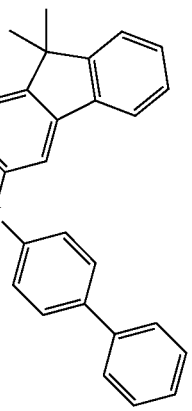

44
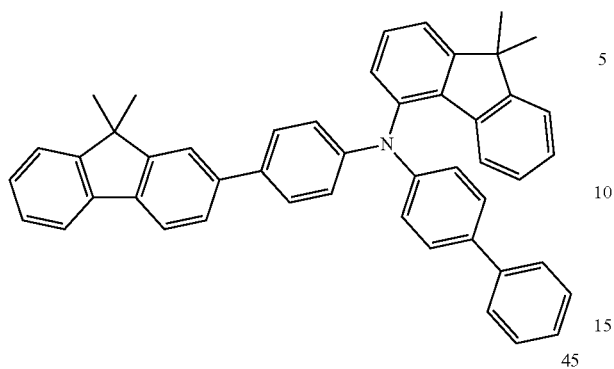
45
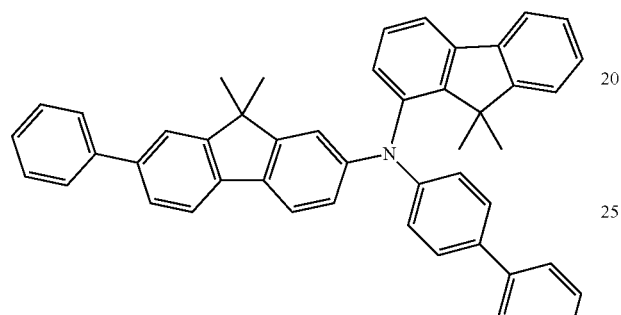
46
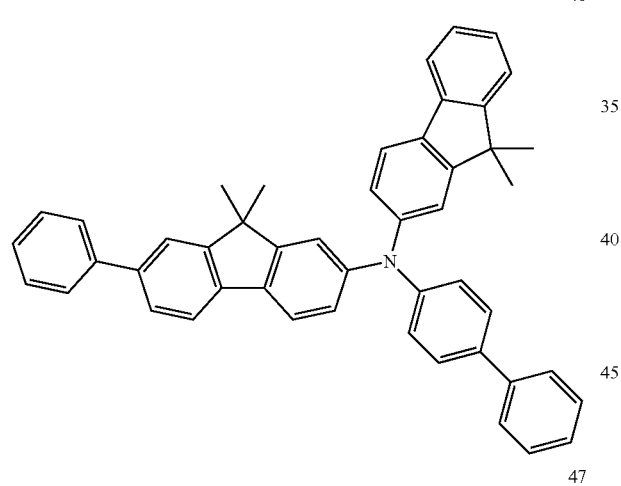
47
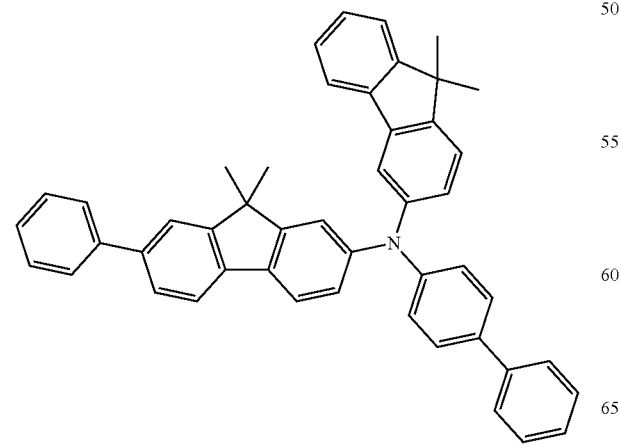
48
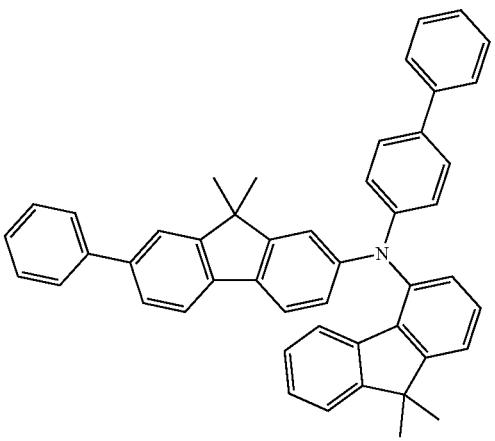
49
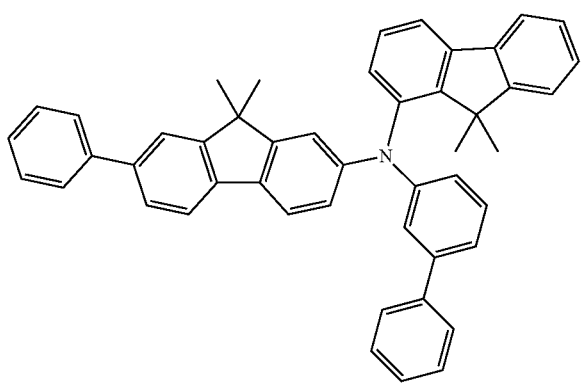
50
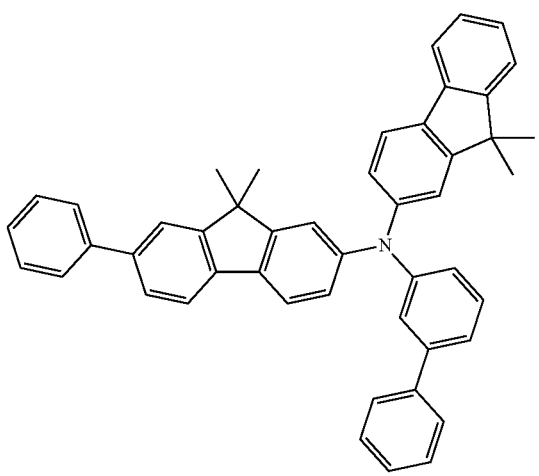

51
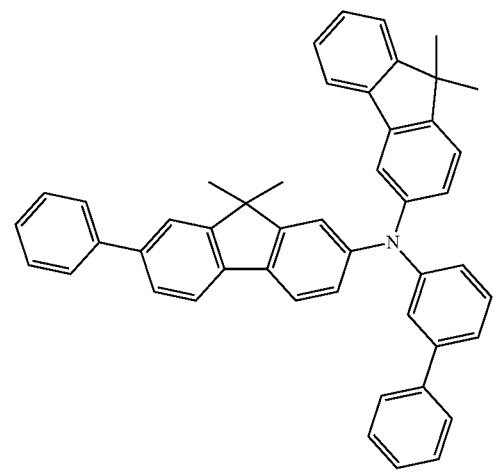
52
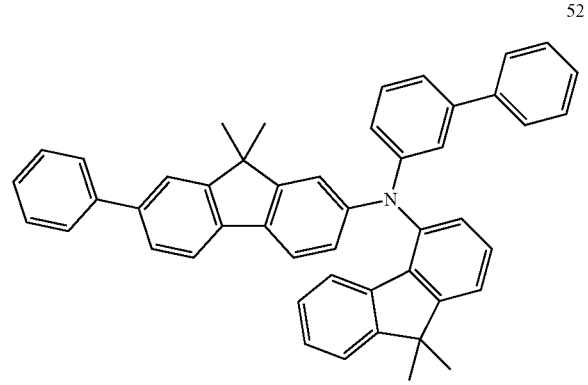
53
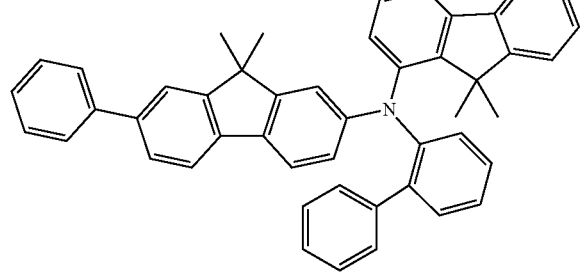
54
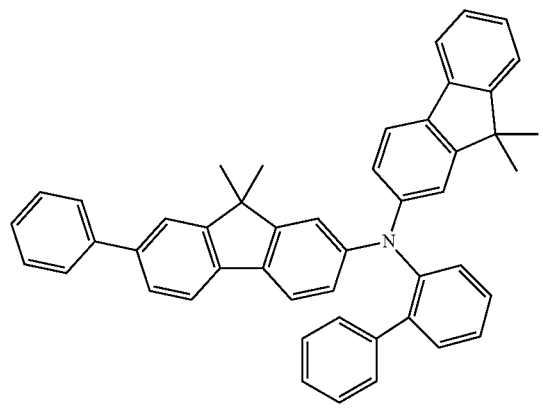
55
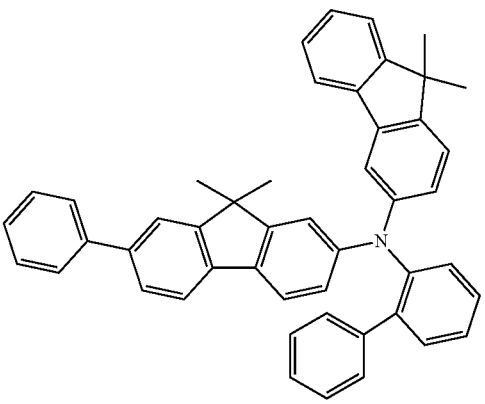
56
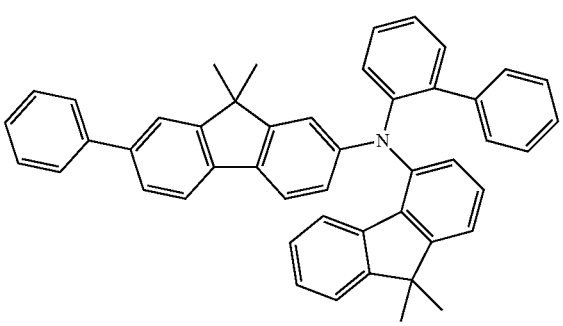
57
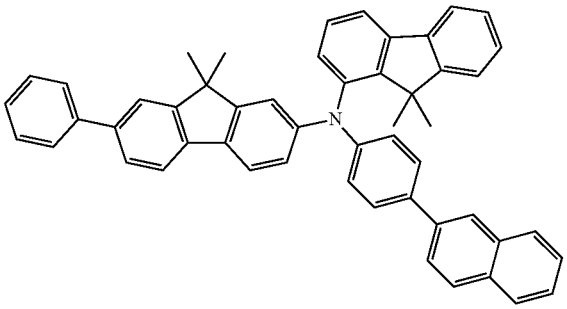
58
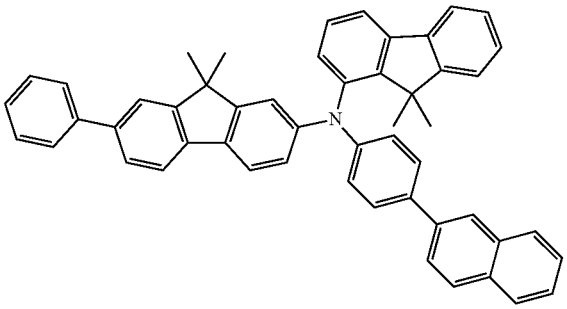

-continued
59
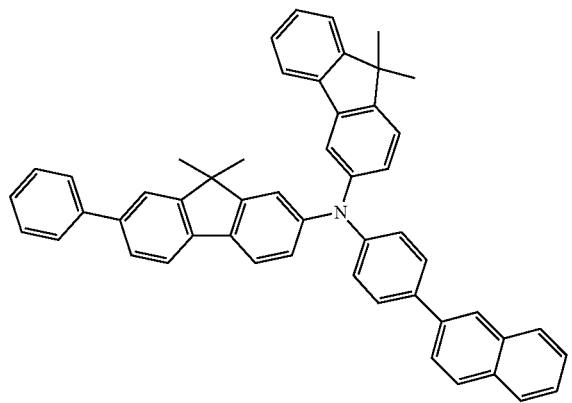
60
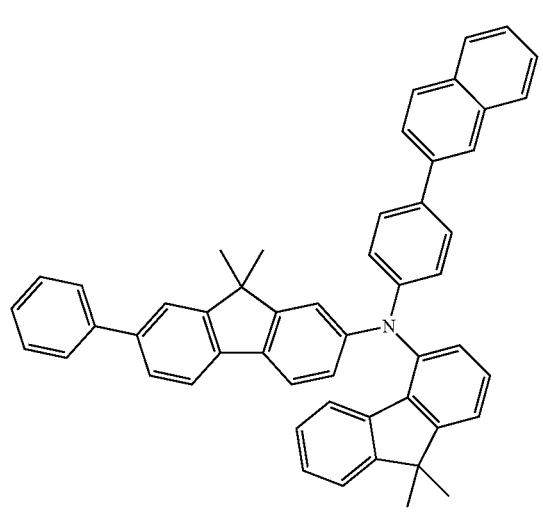
61
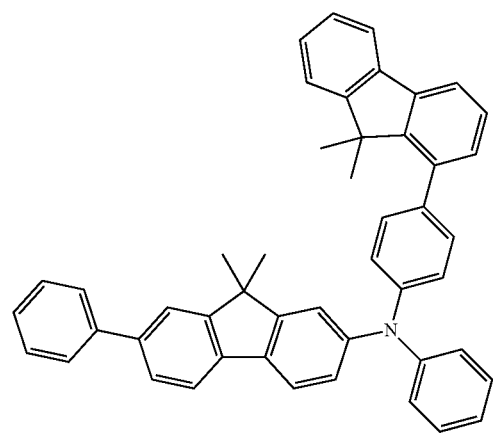
-continued
62
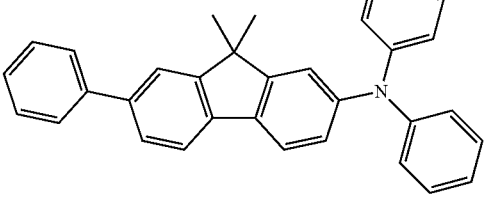
63
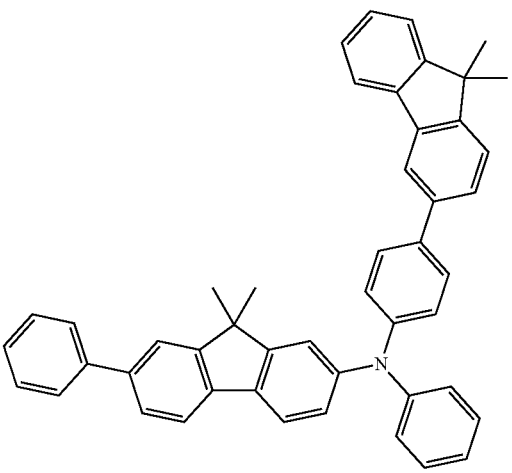
64
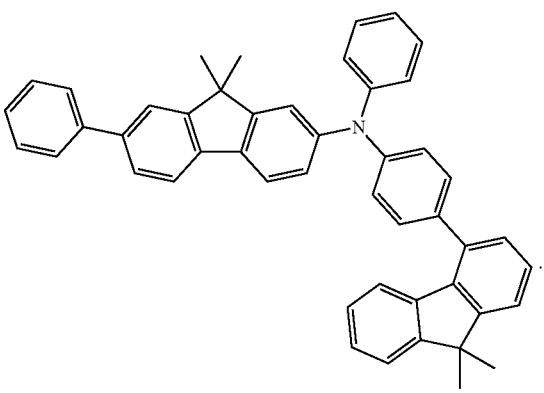

10. The composition as claimed in claim 1, wherein the second compound is a compound of the following Group 2:
[Group 2]
81
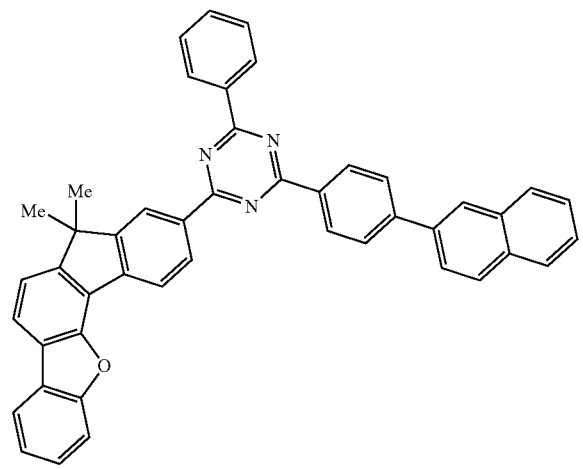
82
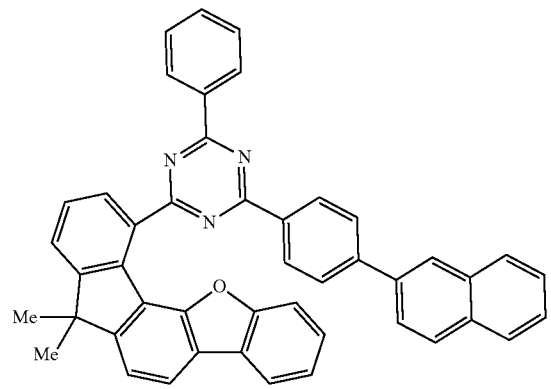
83
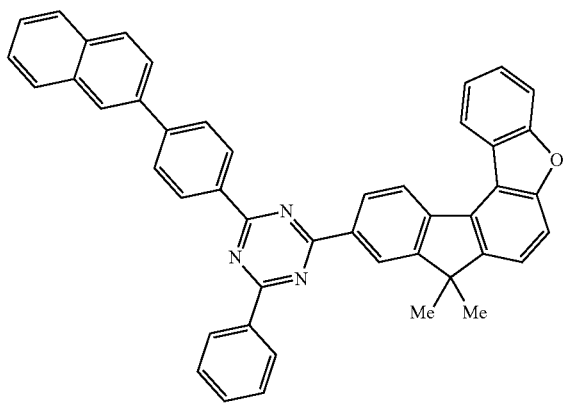
84
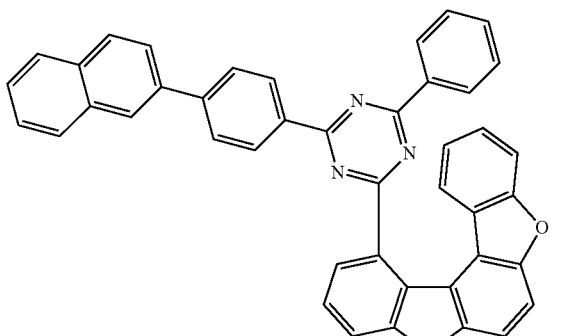
85
86
87
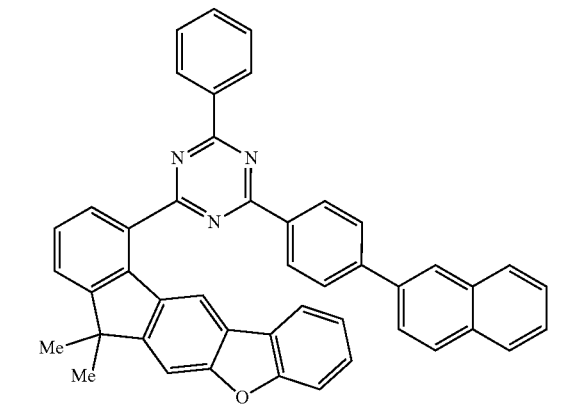

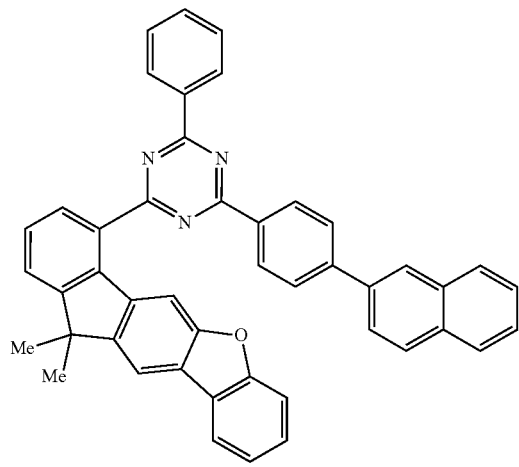
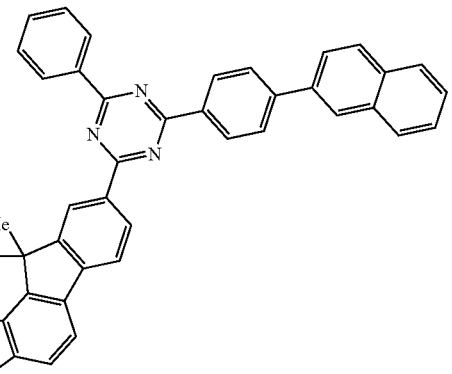
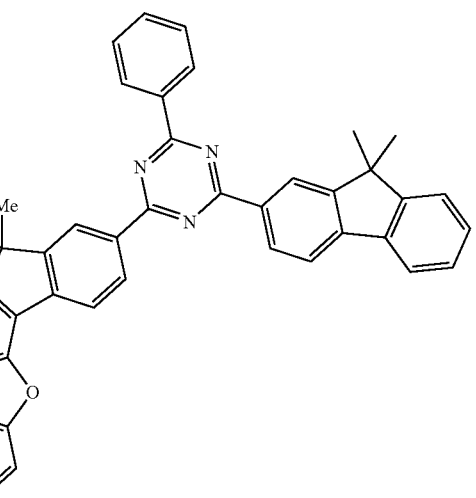

-continued

94
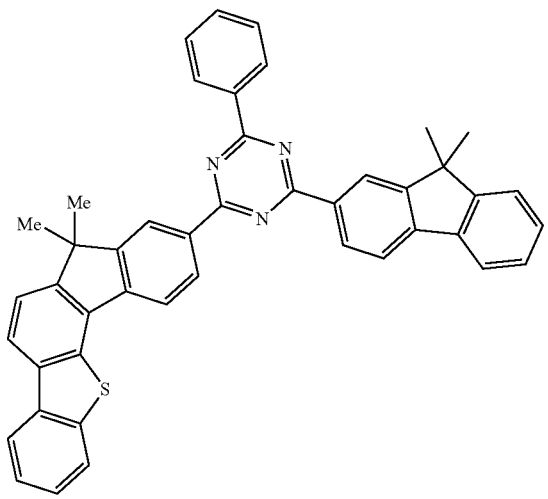

95
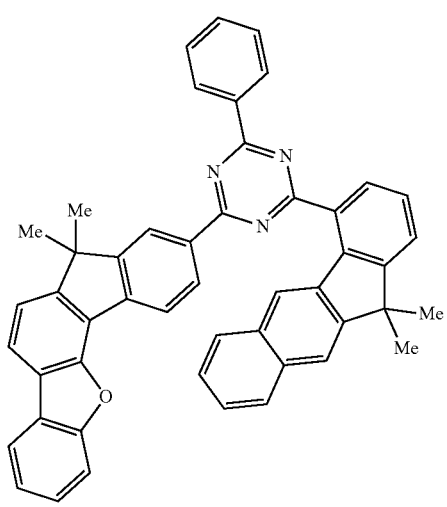

96
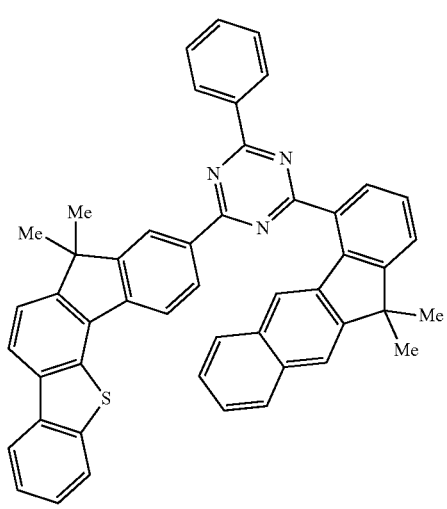

-continued

97
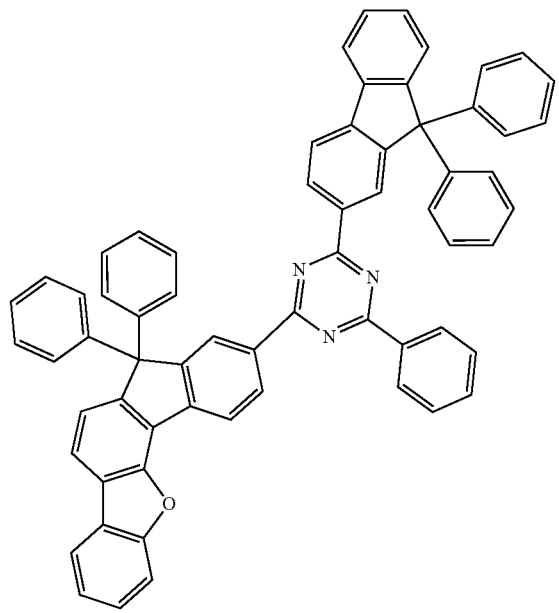

98
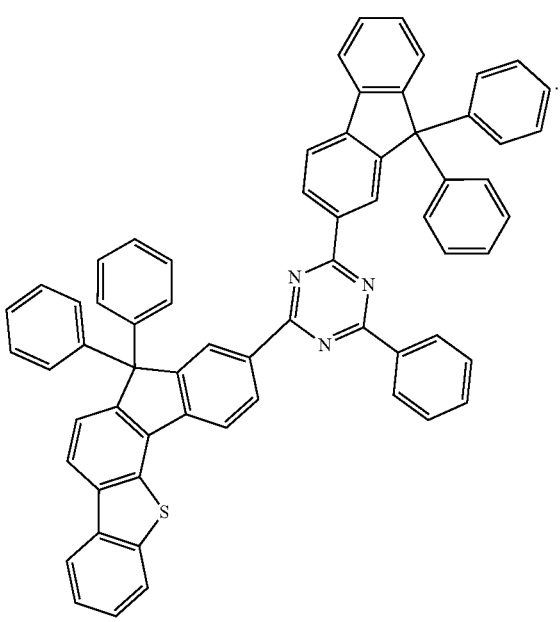

11. An organic optoelectronic device, comprising:
an anode and a cathode facing each other, and
at least one organic layer between the anode and the cathode,
wherein the at least one organic layer includes a light emitting layer, and
the light emitting layer includes the composition for an organic optoelectronic device as claimed in claim 1.

12. The organic optoelectronic device as claimed in claim 11, wherein the composition for an organic optoelectronic device is a host in the light emitting layer.

13. The organic optoelectronic device as claimed in claim 12, wherein the composition for an organic optoelectronic device includes the first compound and the second compound in a weight ratio of about 90:10 to about 40:60.

14. A display device comprising the organic optoelectronic device as claimed in claim 11.

\* \* \* \* \*